(12) United States Patent
Radlauer et al.

US009233996B2

(10) Patent No.: US 9,233,996 B2
(45) Date of Patent: Jan. 12, 2016

(54) MULTI-METALLIC ORGANOMETALLIC COMPLEXES, AND RELATED POLYMERS, COMPOSITIONS, METHODS AND SYSTEMS

(75) Inventors: Madalyn Radlauer, Pasadena, CA (US); Joshua D. Wiensch, Pasadena, CA (US); Aya K. Buckley, West Caldwell, NJ (US); Theodor Agapie, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 13/615,552

(22) Filed: Sep. 13, 2012

(65) Prior Publication Data

US 2013/0066029 A1 Mar. 14, 2013

Related U.S. Application Data

(60) Provisional application No. 61/550,878, filed on Oct. 24, 2011, provisional application No. 61/534,187, filed on Sep. 13, 2011.

(51) Int. Cl.

| C07F 15/04 | (2006.01) |
|---|---|
| C08F 4/70 | (2006.01) |
| C08F 10/00 | (2006.01) |
| C07F 17/00 | (2006.01) |
| C08F 4/60 | (2006.01) |
| C07F 7/00 | (2006.01) |
| C08F 110/02 | (2006.01) |
| C08F 210/14 | (2006.01) |
| C08F 4/619 | (2006.01) |
| C08F 4/6592 | (2006.01) |

(52) U.S. Cl.
CPC ............ *C07F 17/00* (2013.01); *C07F 7/006* (2013.01); *C07F 15/04* (2013.01); *C07F 15/045* (2013.01); *C08F 4/60003* (2013.01); *C08F 4/60189* (2013.01); *C08F 4/619* (2013.01); *C08F 4/6592* (2013.01); *C08F 10/00* (2013.01); *C08F 110/02* (2013.01); *C08F 210/14* (2013.01); *C08F 2410/01* (2013.01); *C08F 2410/03* (2013.01); *C08F 2420/02* (2013.01)

(58) Field of Classification Search
CPC .... C07F 15/04; C07F 15/045; C08F 4/60189; C08F 4/60003; C08F 10/00
USPC ................................................. 556/138, 146
See application file for complete search history.

(56) References Cited

U.S. PATENT DOCUMENTS

| 6,153,776 | A | 11/2000 | Patton et al. |
|---|---|---|---|
| 6,288,254 | B1 | 9/2001 | Chen et al. |
| 2004/0106514 | A1 | 6/2004 | Nagy et al. |
| 2006/0270811 | A1* | 11/2006 | Shen et al. ........... 526/113 |

FOREIGN PATENT DOCUMENTS

KR 10-2004-0076965 9/2004

OTHER PUBLICATIONS

Johnson, L.K. et al "New Pd(II)—and Ni(II)-Based Catalysts for Polymerization of Ethylene and α Olefins", Journal of the American Chemical Society (1995), 117, p. 6414-6415.
Hanaoka. H. et al "Synthesis and characterization of titanium alkyl, oxo, and diene complexes bearing a SiMe2-bridged phenoxy-cyclopentadienyl ligand and their catalytic performance for copolymerization of ethylene and 1-hexene". Journal of Organometallic Chemistry 692 (2007) pp. 4717-4724.
Wehrmann, P. et al. "Copolymerization of Ethylene with 1-Butene and Norbornene to Higher Molecular Weight Copolymers in Aqueous Emulsion" Macromolecules (2006), 39, pp. 5995-6002.
Agapie, T., Bercaw, J., Cyclometalated Tantalum Diphenolate Pincer Complexes: Intramolecular C—H/M—CH₃ σ-Bond Metathesis May Be Faster than O—H/M—CH₃ Protonolysis. 2007. *Organometallics.* 26:2957-2959.
Akama, T., et al., Design and Synthesis of Potent Antitumor 5,4'-Diaminoflavone Derivatives Based on Metabolic Considerations. 1997. *J. Med. Chem.* 40:1894-1900.
Amin, S., Marks, T., Versatile Pathways for In Situ Polyolefin Functionalization with Heteroatoms: Catalytic Chain Transfers. 2008. *Angew. Chem. Int. Ed.* 47:2006-2025.
Anselment, T., et al., Activation of Late Transition Metal Catalysts for Olefin Polymerizations and Olefin/ CO Copolymerizations. 2008. *Dalton Trans.* 4537-4548.
Appiah, W., et al., Linear Trimer Analogues of Calixarene as Chiral Coordinating Ligands: X-ray Crystallographic and NMR Spectroscopic Characterization of Chiral and Achiral Trisphenolates Complexed to Titanium(IV) and Aluminum (III). 2002. *Inorg. Chem.* 41:3656-3667.
Bauers, F., Mecking, S., Aqueous Homo- and Copolymerization of Ethylene by Neutral Nickel (II) Complexes. 2001. *Macromolecules.* 34:1165-1171.
Berkefeld, A., et al., Mechanistic Insights on the Copolymerization of Polar Vinyl Monomers with Neutral Ni(II) Catalysts. 2009. *J Am Chem.* 131:12613-12622.
Bianchini, C., Alternating Copolymerization of Carbon Monoxide and Olefins by Single-Site Metal Catalysis. 2002. *Coordination Chemistry Reviews.* 225:35-66.
Boffa, L., Novak, B., Copolymerization of Polar Monomers with Olefins Using Transition-Metal Complexes. 2000. *Chem Rev.* 100:1479-1493.
Britovsek, G., et al., The Search for New-Generation Olefin Polymerization Catalysts: Life Beyond Metallocenes. 1999. *Angew Chem Int Ed.* 38:428-447.
Chen, E., Coordination Polymerization of Polar Vinyl Monomers by Single-Site Metal Catalysts. 2009. *Chem Rev.* 109:5157-5214.
Chen, Q., Huang, J., Arene-Bridged Salicylaldimine-Based Neutral Nickel(II) Complexes: Synthesis and Ethylene Polymerization Activities. 2007.*Organometallics.* 26:617-625.
Coates, G., Moore, D., Discrete Metal-Based Catalysts for the Copolymerization of CO2 and Epoxides: Discovery, Reactivity, Optimization and Mechanism. 2004. Angew Chem Int Ed. 43:6618-6639.
Coates, G., Heslop, J., Some Co-ordination Complexes of Dimethyl- and Diphenyl-magnesium with Ethers and Amines. 1966. *J Chem Soc. (A)* 26-27.
Cohen, A., et al., Construction of C₁-Symmetric Zirconium Complexes by the Design of New Salan Ligands. Coordination Chemistry and Preliminary Polymerisation Catalysis Studies. 2008. *Chem. Commun.* 2149-2151.
Connor, E., et al., Synthesis of Neutral Nickel Catalysts for Ethylene Polymerization—The Influence of Ligand Size on Catalyst Stability. 2003. *Chem Commun.* 2272-2273.

(Continued)

*Primary Examiner* — Caixia Lu
(74) *Attorney, Agent, or Firm* — Steinfl & Bruno LLP

(57) ABSTRACT

Multi-metallic organometallic complexes that allow performance of olefin based reaction and in particular polymerization of olefins to produce polyolefin polymers, and related methods and systems are described.

32 Claims, 30 Drawing Sheets

(56) References Cited

OTHER PUBLICATIONS

Connor, E., et al., Linear Functionalized Polyethylene Prepared with Highly Active Neutral Ni(II) Complexes. 2002. *Journal of Polymer Science Part A: Polymer Chemistry*. 40:2842-2854.

Cornelissen, J., et al., Chiral Architectures from Macromolecular Building Blocks. 2001. *Chem Rev* 101: 4039-4070.

Covert, K et al., Carbon—Oxygen and Related R—X Bond Cleavages Mediated by (silox)$_3$Ti and Other Group 4 Derivatives (silox=$^t$Bu$_3$SiO). 1997. *Inorganica Chimica Acta*. 263:263-278.

Dahl, O., Four- and Five-Coordinate Nickel(II) Complexes with Trimethylphosphine, *Acta Chemica Scand*. 1969, 23: 2342-2354.

Dechy-Cabaret, O., et al., Controlled Ring-Opening Polymerization of Lactide and Glycolide, Chem. Rev. 2004, 104: 6147-6176.

Delferro, M., et al., Multinuclear Olefin Polymerization Catalysts, Chem. Rev. 2011, 111: 2450-2485.

Deng, L., et al., "A density functional study of Nickel (II) diimide catalyzed polymerization of ethylene." *Journal of the American Chemical Society* 1997 119(5): 1094-1100.

Dong, J.Y., et al., Synthesis of Isotactic Polypropylene Containing a Terminal CI, OH, or NH2 group via Metallocene-Mediated Polymerization/Chain Transfer Reaction, Macromolecules 2002, 35: 9352-9359.

Dong, J.Y., et al., Design and synthesis of structurally well-defined functional polyolefins via transition metal-mediated olefin polymerization chemistry, Coor. Chem. Rev. 2006, 250: 47-65.

Drent, E., et al., Palladium catalysed copolymerisation of ethene with alkylacrylates: polar comonomer built into the linear polymer chain, ChemCommun. 2002, 744-745.

Drent, E., et al. Palladium-Catalyzed Alternating Copolymerization of Alkenes and Carbon Monoxide, Chem. Rev. 1996, 96: 663-681.

Fuhrmann, H., et al., Octahedral Group 4 Metal Complexes That Contain Amine, Amido, and Aminopyridinato Ligands: Synthesis, Structure, and Application in r-Olefin Oligo- and Polymerization, Inorg. Chem. 1996, 35: 6742-6745.

Gates, D.P., Synthesis of Branched Polyethylene Using (R-Diimine)nickel(II) Catalysts: Influence of Temperature, Ethylene Pressure, and Ligand Structure on Polymer Properties, Macromolecules 2000, 33: 2320-2334.

Gottker-Schnetmann, I., et al., Substituent Effects in (K2-*N,O*)-Salicylaldiminato Nickel(II)-Methyl Pyridine Polymerization Catalysts: Terphenyls Controlling Polyethylene Microstructures, Organometallics 2007, 26: 2348-2362.

Guo, N., et al., Bimetallic Catalysis for Styrene Homopolymerization and Ethylene-Styrene Copolymerization. Exceptional Comonomer Selectivity and Insertion Regiochemistry, J. Am. Chem. Soc.. 2004, 126: 6542-6543.

Guo, N., et al., Bimetallic Effects in Homopolymerization of Styrene and Copolymerization of Ethylene and Styrenic Comonomers: Scope, Kinetics, and Mechanism, J. Am. Chem. Soc.2008, 130: 2246-2261.

Gust, D., Restricted Rotation in Hexaarylbenzenes, J. Am. Chem. Soc. 1977, 99: 6980-6982.

Hamaed, A., et al., H2 Storage Materials (22KJ/mol) Using Organometallic Ti Fragments as σ-H2 Binding Sites, J. Am. Chem. Soc. 2008, 130: 6992-6999.

Han, S., et al., "Binuclear Heteroligated Titanium Catalyst Based on Phenoxyimine Ligands: Synthesis, Characterization, and Ethylene (Co)polymerization." *Macromolecules* 2012 45(10): 4054-4059.

Hanaoka, H., et al., Synthesis and characterization of titanium and zirconium complexes with silicone-bridged phenoxycyclopentadienyl ligands, J. Organomet. Chem. 2007, 692: 4059-4066.

Hoogasian, S., et al., Stereodynmics of Acyclic Alchols, Ethers, and N,N-Dimethylurethanes. Potential Barriers to Rotation about Carbon—Carbon and Carbon—Nitrogen Bonds, J. Phy. Chem. 1976, 80: 643-648.

Hu, T., et al., Synthesis and Ethylene Polymerization Activity of a Novel, Highly Active Single-Component Binuclear Neutral Nickel(II) Catalyst, Organometallics 2005, 24: 2628-2632.

Imuta, J., et al., Catalytic Regioselective Introduction of Allyl Alcohol into the Nonpolar Polyolefins: Development of One-Pot Synthesis of Hydroxyl-Capped Polyolefins Mediated by a New Metallocene IF Catalyst, J. Am. Chem. Soc. 2002, 124: 1176-1177.

PCT International Search Report mail on Feb. 7, 2013 for PCT Application No. PCT/US2012/055258 filed on Sep. 13, 2012 in the name of California Institute of Technology et al.

Ittel, S., et al., Late-Metal Catalysts for Ethylene Homo- and Copolymerization, Chem. Rev. 2000, 100: 1169-1203.

Janiak, C., A critical account on π-π stacking in metal complexes with aromatic nitrogen-containing ligands, J. Chem. Soc. Dalton Trans. 2000, 3885-3896.

Jenkins, J., et al., A Mechanistic Investigation of the Polymerization of Ethylene Catalyzed by Neutral Ni(II) Complexes Derived from Bulky Anilinotropone Ligands, J. Am. Chem. Soc. 2004, 126: 5827-5842.

Johnson, L., et al., Copolymerization of Ethylene and Propylene with Functionalized Vinyl Monomers by Palladium(II) Catalysts, J. Am. Chem. Soc. 1996, 118: 267-268.

Kaur, I., et al., Design, Synthesis, and Characterization of a Persistent Nonacene Derivative, J. Am. Chem. Soc. 2010, 132: 1261-1263.

Kiesewetter, E., et al., Stereospecific Octahedral Group 4 Bis(phenolate) Ether Complexes for Olefin Polymerization, J. Am. Chem. Soc. 2010, 132: 5566-5567.

Klabunde, U., et al., Ethylene Homopolymerization with P,O-Chelated Nickel Catalysts, J. Polymer Science Part A: Polymer Chemistry 1987, 25: 1989-2003.

Klien, KF., et al., Methyl(trimethylphosphin)nickel-hydroxid and verwandte Verbindungen, Chem. Ber. 1973, 106: 1433-1452.

Koning, C., et al., Strategies for Compatibilization of Polymer Blends, Prog. Polym. Sci. 1998, 23: 707-757.

Kuran, W. Coordination Polymerization of Hetereocyclic and Heterounsaturated monmers, Prog. Polym. Sci. 1998, 23: 919-992.

Leadbeter, N., et al., Preparation of Polymer-Supported Ligands and Metal Complexes for Use in Catalysis, Chem. Rev. 2002, 102: 3217-3274.

Li, H., et al., Coordination Copolymerization of Severely Encumbered Isoalkenes with Ethylene: Enhanced Enchainment Mediated by Binuclear Catalysts and Cocatalysts, J. Am. Chem. Soc. 2005, 127: 14756-14768.

Li, H., et al., Nuclearity and cooperativity effects in binuclear catalysts and cocatalysts for olefin polymerization, PNAS 2006, 103: 42: 15295-15302.

Lodiero, S., et al., Protostadienol Biosynthesis and Metabolism in the Pathogenic Fungus *Aspergillus fumigates*, Organic Letters 2009, 11: 1241-1244.

Lopez, R., et al., Synthesis of well-defined polymer architectures by successive catalytic olefin polymerization and living/controlled polymerization reactions, Prog. Polym. Sci. 2007, 32: 419-454.

Lunazzi, L., et al., Structure, Conformation, and Dynamic Processes of the Stereolabile Atropisomers of Hindered Terphenyl Hydrocarbons, Organic Letters 2005, 7: 1291-1294.

Makiao, H., et al., FI Catalysts for Olefin Polymerization—A Comprehensive Treatment, Chem. Rev. 2011, 111: 2363-2449.

Manzer, LE., Tetrahydrofuran Complexes of Selected Early Transition Metals, Inorganic Synthesis 1982, pp. 135-140.

Margl, P., et al., "A Unified View of Ethylene Polymerization by d0 and d0f n Transition Metals. 3. Termination of the Growing Polymer Chain." *Journal of the American Chemical Society* 1999 121(1): 154-162.

Maurya, M., et al., Polymer-bound metal complexes as catalysts: Synthesis, characterization, reactivity and catalytic activity in EeH bond activation, J. Organomet. Chem. 2011, 696: 244-254.

Mecking, S., et al., Mechanistic Studies of the Palladium-Catalyzed Copolymerization of Ethylene and R-Olefins with Methyl Acrylate, J. Am. Chem. Soc. 1998, 120: 888-899.

Mitchell, R., et al., An Experimental Estimation of Aromaticity Relative to that of Benzene. The Synthesis and NMR Properties of a Series of Highly Annelated Dimethyldihydropyrenes: Bridge Benzannuylenes, J. Am. Chem. Soc. 1995, 117: 1514-1532.

Na, S., et al., Bimetallic nickel complexes of macrocyclic tetraiminodiphenols and their ethylene polymerization, J. Organomet. Chem. 2006, 691: 611-620.

(56) References Cited

OTHER PUBLICATIONS

Nakamura, A., et al., Coordination-Insertion Copolymerization of Fundamental Polar Monomers, Chem. Rev. 2009, 109: 5215-5244.
Pangborn, A., et al., Safe and Convenient Procedure for Solvent Purification, Organometallics 1996, 15: 1518-1520.
Pennington, D., et al., The synthesis, structure and ethene polymerisation catalysis of mono(salicylaldiminato) titanium and zirconium complexes, Dalton Trans. 2005, 561-571.
Radlauer, M., et al., Dinickel Bisphenoxyiminato Complexes for the Polymerization of Ethylene and α-Olefins, Organometallics 2012, 31: 2231-2243.
Radlauer, M., et al., Bimetallic Effects on Ethylene Polymerization in the Presence of Amines: Inhibition of the Deactivation by Lewis Bases, J. Am. Chem. Soc. 2012, 134: 1478-1481.
Rodriguez, B., et al., Bimetallic Effects for Enhanced Polar Comonomer Enchainment Selectivity in Catalytic Ethylene Polymerization, J. Am. Chem. Soc. 2009, 131: 5902-5919.
Rodriguez, B., et al., Neutral Bimetallic Nickel(II) Phenoxyiminato Catalysts for Highly Branched Polyethylenes and Ethylene-Norbornene Copolymerizations, Organomet. 2008, 27: 2166-2168.
Rodriguez, B., et al., Bimetallic Effects for Enhanced Polar Comonomer Enchainment Selectivity in Catalytic Ethylene Polymerization, J. Am. Chem. Soc 2009, 131: 5902-5919.
Salata, M.R., et al., "Synthesis, characterization, and marked polymerization selectivity characteristics of binuclear phenoxyiminato organozirconium catalysts." *J Am Chem Soc* 2008 130(1): 12-13.
Salata, M.R., et al., "Catalyst Nuclearity Effects in Olefin Polymerization. Enhanced Activity and Comonomer Enchainment in Ethylene+ Olefin Copolymerizations Mediated by Bimetallic Group 4 Phenoxyiminato Catalysts." *Macromolecules* 2009 42(6): 1920-1933.
Schubbe, et al;., Struktur der aktiven Spezies und Erklarung des Wanderungsmechanismus bei der 2,wPolymerisation von a-Olefinen, Macromol. Chem. Phys. 1995, 196: 467-478 (English Abstract only).
Senda, T., et al., Substituent Effects on Silicon of Bridged Tetramethylcyclopentadienyl-Phenoxy Titanium Complexes for Controlling the Regiochemistry and Molecular Weight in 1-Olefin Polymerization, Macromolecules 2009, 42: 8006-8009.
Shaughnessy, K. et al., "Insertion Polymerization and Oligomerization of Alkenes Part 1: Early Transition Metals." The University of Alabama, Tuscaloosa, AL, Spring 2011 (11 pp.).
Stead, D., et al., A New Sparteine Surrogate for Asymmetric Deprotonation of N-Boc Pyrrolidine, Organic Letters 2008, 10: 1409-1412.
Sujith, S., et al., Ethylene/Polar Norbornene Copolymerizations by Bimetallic Salicylaldimine-Nickel Catalysts, Macromolecules 2005, 38: 10027-10033.
Wang, C., et al., Synthesis and Characterization of Titanium(IV) Complexes Bearing Monoanionic [O—NX] (X) O, S, Se) Tridentate Ligands and Their Behaviors in Ethylene Homo- and Copolymerizaton with 1-Hexene, Organometallics 2006, 25: 3529-3266.
Wang, C., et al.,Neutral Nickel(II)-Based Catalysts for Ethylene Polymerization, Organometallics 1998, 17: 3149-3151.
Wang, W., et al., Binuclear neutral nickel complexes bearing bis(bidentate) salicylaldiminato ligands: Synthesis, structure and ethylene polymerization behavior, Inorganic Chem. Comm. 2006, 9: 548-550.
Wehrmann, P., et al., Highly Active Binuclear Neutral Nickel(II) Catalysts Affording High Molecular Weight Polyethylene, Organometallics 2008, 27: 1399-1408.
Wehrmann, P., et al., Aqueous Dispersions of Polypropylene and Poly(1-butene) with Variable Microstructures Formed with Neutral Nickel(II) Complexes, Macromolecules 2006, 39: 5963-5964.
Widger, P., et al., Isospecific polymerization of racemic epoxides: a catalyst system for the synthesis of highly isotactic polyethers, ChemComm. 2010, 46: 2935-2937.
PCT Written Opinion mail on Feb. 7, 2013 for PCT Application No. PCT/US2012/055258 filed on Sep. 13, 2012 in the name of California Institute of Technology et al.
Wu, F., et al., Acrylonitrile Insertion Reactions of Cationic Palladium Alkyl Complexes, J. Am. Chem. Soc. 2005, 127: 1841-1853.
Yan, Y., et al., Helical Organization in Foldable Aromatic Oligoamides by a Continuous Hydrogen-Bonding Network, Organic Letters 2009, 11: 1201-1204.
Younkin, T., et al., Neutral, Single-Component Nickel (II) Polyole Þ n Catalysts That Tolerate Heteroatoms, Science 2000, 287: 460-462.
Zhang, Y., et al., Catalyst-Site-Controlled Coordination Polymerization of Polar Vinyl Monomers to Highly Syndiotactic Polymers, J. Am. Chem. Soc. 2010, 132: 2695-2709.
Zhang, D., et al., Novel, Highly Active Binuclear 2,5-Disubstituted Amino-p-benzoquinone-Nickel(II) Ethylene Polymerization Catalysts, Organometallics 2003, 22: 2851-2854.
Zhang, S., et al., Bimetallic (Iron or Cobalt) Complexes Bearing 2-Methyl-2,4-bis(6-iminopyridin-2-yl)-1H-1,5-benzodiazepines for Ethylene Reactivity, Organometallics 2007, 26: 2456-2460.
Zhang, D., et al., Bimetallic nickel complexes of trimethyl phenyl linked salicylaldimine ligands: Synthesis, structure and their ethylene polymerization behaviors, Inorg. Chem. Comm. 2006, 9: 1322-1325.
Zuideveld, M., et al., Remote Substituents Controlling Catalytic Polymerization by Very Active and Robust Neutral Nickel(ii) Complexes, Angew. Chemie Int. Ed.. 2004, 43: 869-873.
Zysman-Colman, E., et al., Synthesis of arylbromides from arenes and N-bromosuccinimide (NBS) in acetontrile—A convenient method for aromatic bromination, Can. J. Chem. 2009, 87: 440-447.
Yeori, A. et al. *Diastereomerically-Specific Zirconium Complexes of Chiral Satan Ligands: Isospecific Polymerization of 1-Hexene and 4-Methyl-1-pentene and Cyclopolymerization of 1,5-Hexadiene.* J. Am. Chem. Soc., vol. 128, pp. 13062-13063. 2006.
Khylabich, P. P. et al. *Compositional Dependence of the Open-Circuit Voltage in Ternary Blend Bulk Heterojunction Solar Cells Based on Two Donor Polymers.* J. Am. Chem. Soc., vol. 134, pp. 9074-9077. 2012.
Makio, H. et al. FI Catalysts for Olefin Polymerization—A Comprehensive Treatment. *Chemical Reviews.* vol. 111, pp. 2363-2449, 2011.
Strianese, M et al.*A Comparative Study on the Polymerization of α-Olefins Catalyzed by Salen and Salan Zirconium Complexes.* Marcomol. Chem. Phys., vol. 209, pp. 585-502. 2008.
Park, H. et al. *Highly rigid and twisted anthracene derivatives: a strategy for deep blue OLED materials with theoretical limit efficiency.* J. Mater. Chem., vol. 22, pp. 2695-2700. 2012.
Tshuva, Y. et al. *Isospecific Living Polymerization of 1-Hexene by a Readily Available Nonmetallocene C2-Symmetrical Zirconium Catalyst.* J. Am. Chem. Soc., vol. 122, pp. 10706-10707. 2000.
Burkhart, B. et al. Influence of the Acceptor Composition on Physical Properties and Solar Cell Performance in Semi-Random Two-Acceptor Copolymers. *ACS Macro Letters*, vol. 1, pp. 660-666. 2012.
Tshuva, Y. et al. *Isospecific Living Polymerization of 1-Hexene by a Readily Available Nonmetallocene Ci-Symmetrical Zirconium Catalyst.* J. Am. Chem. Soc., 9 pgs. 2000.
Radlauer, M.R. et al. Bimetallic Zirconium Amine Bis(phenolate) Polymerization Catalysts: Enhanced Activity and Tacticity Control for Polyolefin Synthesis. Organomettalics, vol. 33, pp. 3247-3250. 2014.
Thomas R. et al. "Enantioselective Epoxide Polymerization Using a Bimetallic Cobalt Catalyst" J. Am. Chem. Soc., 2010, 132 (46), pp. 16520-16525.
"Polymer" Wikipedia—accessed via WayBackMachine.com, Aug. 16, 2012 https://en.wikipedia.org/wiki/polymer. Retrieved Nov. 12, 2014, pp. 1-16.
"Polystyrene" Wikipedia—accessed via WayBackMachine.com, Aug. 16, 2012 https://en.wikipedia.org/wiki/polystyrene. Retrieved on Nov. 12, 2014, pp. 1-14.
"Tacticity" Wikipedia—accessed via WayBackMachine.com, May 12, 2012. https://en.wikipedia.org/wiki/tacticity. Retrieved on Nov. 12, 2014, pp. 1-7.

\* cited by examiner

M, M' = metal; complex can be neutral or charged
L, $L_n$ = neutral or anionic ligand set
X = neutral or anionic donor
R = anionic donor
▬▬▬▬▬ = rigid, aryl linker M, M' = metal; complex can be neutral or charged
L, L_n = neutral or anionic ligand set
R = hydrocarbyl (polymeryl chain)
R' = hydrocarbyl substituent
▓▓▓▓▓▓▓▓ = rigid, aryl linker M, M' = metal; complex can be neutral or charged
L, L$_n$ = neutral or anionic ligand set
P = polymeryl chain
▬▬▬ = rigid, aryl linker

MULTI-METALLIC ORGANOMETALLIC COMPLEXES, AND RELATED POLYMERS, COMPOSITIONS, METHODS AND SYSTEMS

CROSS REFERENCE TO RELATED APPLICATIONS

The present application claims priority to U.S. Provisional Application No. 61/534,187, entitled "Bimetallic olefin polymerization catalysts with rigid triaryl linkers" filed on Sep. 13, 2011, and to U.S. Provisional Application No. 61/550,878, entitled "Bimetallic olefin polymerization catalysts with rigid triaryl linkers" filed on Oct. 24, 2011, each of which is incorporated herein by reference in its entirety.

FIELD

The present disclosure relates to multi-metallic organometallic complexes, and related polymers, compositions, methods, and systems. In particular, the present disclosure relates to multi-metallic organometallic complexes suitable as catalysts for olefin based reactions.

BACKGROUND

Olefin based reactions are widespread in a variety of research and industrial applications, such as fuels, material science, petrochemicals, and pharmaceuticals wherein performance of efficient olefin based reaction is desired. As a consequence development of metal based catalysts possibly designed for increasing efficiency in rate, yield or other reaction conditions and parameters has been pursued according to various approach.

In particular, development of efficient catalysts has been a challenge in reactions involving olefin polymerization, in particular when aimed at production of functionalized polyolefins.

Functionalized polyolefins have a number of desirable physical properties including greater adhesion to substrates and greater compatibility with other materials for use in polymer blends and composites and additional properties identifiable by a skilled person.

Despite production of several organometallic catalysts, development of functionalized polyolefin has been a challenge in particular when directed at production of functionalized polyolefin with a broad scope, efficient rate and control over various properties of the polyolefins produced.

SUMMARY

Described herein are multi-metallic organometallic complexes that in some embodiments can be used in olefin based reactions, and related compositions, polymers, methods and systems. In particular, in some embodiments, the multi-metallic organometallic complexes herein described allow oligomerization of olefin monomers, and/or polymerization of olefin monomers to provide polyolefin polymers.

According to a first aspect, an multi-metallic organometallic complex is described, the multi-metallic organometallic complex comprising a rigid base linker comprising a central ring attaching two or more exterior rings, each of the two or more exterior rings attaching one metal-presenting arm, thus defining two or more metal-presenting arms in syn position with respect to the rigid base linker, wherein each metal-presenting arm of said two or more metal-presenting arms comprises one or more ancillary ligands presenting said metal, said metal is bound to one or more auxiliary ligands through respective one or more auxiliary ligand metal bonds, each said one or more auxiliary ligand metal bonds is adapted to be represented through corresponding one or more auxiliary ligand metal bond three-dimensional vectors originating at said metal, metals pertaining to different metal-presenting arms are located at a metal-to-metal distance defining an imaginary sphere having said metal-to-metal distance as a diameter, and for each of said metals located at the metal-to-metal distance, a resulting vector corresponding to a sum of said one or more auxiliary ligand metal bond three-dimensional vectors is located inside said imaginary sphere. In some embodiments, the exterior rings are each connected to the central ring through a single bond. In other embodiments the central and exterior rings comprise aromatic, heteroaromatic, aliphatic, or hetero aliphatic rings.

According to a second aspect, a method and system for preparing polyolefins are described. The method comprises contacting an olefin monomer with the multi-metallic organometallic complexes herein described. The system comprises at least two of: a multi-metallic organometallic complex and an olefin monomer herein described which in some embodiments are comprised in the system for simultaneous combined or sequential use in a method to produce polyolefin herein described.

According to a third aspect, a catalytic system for olefin polymerization is described, the system comprising one or more of the multi-metallic organometallic complexes herein described and an olefin monomer. In some embodiments, the system further comprises a suitable activator.

According to a fourth aspect, a method and system for preparing a multi-metallic organometallic complex are described. The method comprises selecting a central ring; selecting two or more exterior rings, the exterior rings; contacting the central ring with the two or more exterior rings to provide a rigid linker; selecting one or more ancillary ligands, one or more metals, and one or more auxiliary ligands; contacting the rigid linker with the one or more ancillary ligands to provide a multi-metallic organometallic complex precursor such as a multidentate organometallic compound; contacting the multi-metallic organometallic complex precursor with the one or more metals and auxiliary metals to provide the organometallic complex. The system can comprise at least two of: one more organometallic complex precursor, one or more metals and one or more ancillary ligands, which in some embodiments are comprised in the system for simultaneous combined or sequential use in a method to produce an organometallic complex herein described.

Multi-metallic organometallic complexes and related polymers, compositions, methods and systems herein described in several embodiments allow polymerization of olefin monomers in the presence of polar impurities and/or polar additives.

Multi-metallic organometallic complexes and related polymers, compositions, methods and systems herein described in several embodiments allow polymerization of functionalized olefin monomers to produce functionalized polyolefins.

Multi-metallic organometallic complexes and related polymers, compositions, methods and systems herein described in several embodiments allow control over the tacticity of the polymer, polymer branching, insertion rate of co-monomers, and/or molecular weight of the resultant polymers.

Multi-metallic organometallic complexes and related polymers methods and systems herein described can be used in connection with applications wherein olefin based reactions, and in particular olefin oligomerization and/or olefin polymerization in particular polymerization in the presence of polar additives or copolymerization of functionalized and non-functionalized monomers is desired. The polymerization of non-olefinic monomers is proposed as well. Exemplary applications comprise 1-olefins and in particular 1-olefins with pendant polar groups such as amines, ethers, and carboxylates.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 30 shows two exterior rings (200), each comprising an ancillary ligand (L) attaching a metal (M), attached to a central ring (201) and having restricted rotation about the central ring (201) to provide a multi-metallic organometallic complex having the metals in a syn orientation.

FIG. 31 shows that the size of the metal-to-metal distance can be selected to be slightly less than 2× the length of the smallest non-hydrogen substituent on the metal-binding heteroatom comprised in functionalized olefin according to some embodiments.

FIG. 34 shows a modified version of the monometallic organometallic complex shown in FIG. 33, modified by linking two individual multi-metallic organometallic complexes by a central ring, thus providing a modified multi-metallic complex.

DETAILED DESCRIPTION

Described herein are multi-metallic organometallic complexes that in some embodiments, allow polymerization of olefins to produce polyolefin polymers, and related methods and systems.

In particular, in some embodiments, the multi-metallic organometallic complexes can be used to restrain two or more metals in close proximity can be used as multi-metallic catalysts in preparing polymeric materials.

The term "organometallic complex" as used herein refers to chemical compounds in which there are one or more metal atoms and/or ions bonded to organic compounds through covalent, ionic, or dative bonds and would be understandable to a skilled person upon a reading of the present disclosure. The bonding can be through direct bonding of the carbon atoms of the organic compounds to metal atoms and/or ions through single and/or multiple bonds, such as for example in the cases of metal-alkyl, metal-carbene, and metal-carbyne compounds; or through indirect bonding of the carbon atoms of the organic compounds, such as for example in the cases of heteroatom-containing organic compounds comprising (e.g. containing O, N, S, and others) bonding to metal atoms and/or ions through metal-heteroatom single and/or multiple bonds.

In particular, the term "multi-metallic organometallic complex" refers to an organometallic complex in which an organic compound is bonded to two or more metal atoms and/or ions.

Figure 4:
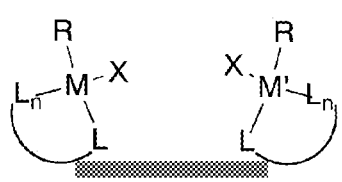
FIG. 4 shows a schematic depiction of the general structure of the multi-metallic polymerization catalysts described herein.

In some embodiments, the multi-metallic organometallic complexes herein described comprise a rigid base linker comprising a central ring attaching two or more exterior rings (See e.g. FIG. 4).

The term "rigid" as used herein refers to a restricted rotation of exterior rings with respect to a central ring in a linker, which can allow the metals of a multi-metallic organometallic complex according to embodiments herein described to be held in a set orientation, and in particular, a syn orientation.

The term "restricted rotation" as used herein refers to rotation about an atom or a bond having a rotational barrier of approximately 25 kcal/mol or higher. Restricted rotation about a bond can detected using approaches such as x-ray crystallography (See e.g. Example 11), NMR (e.g. NOESY and ROESY), an Eyring plot and additional techniques identifiable by a skilled person (See e.g. Example 27). Detection of the rotation barrier of a compound can also be performed by detecting interconversion of the compound following variation of temperature for a desired amount of time, wherein the detection can be performed according to approaches identifiable by a skilled person. In general, compounds having a rotational barrier of approximately 25 kcal/mol or higher are expected not to detectably interconvert up to temperatures of at least 100° C. for a desired duration of time. Exemplary moieties having restricted rotation comprise atropisomers, spirane-type moieties, double bonds, and additional structural moieties identifiable by a skilled person.

The term "linker" as described herein indicates a moiety comprising a central ring attaching to two or more exterior rings. The term "ring" as used herein refers to a cyclic arrangement of atoms. In particular, in some embodiments, the rings can be aromatic (e.g. benzene, naphthalene, anthracene or others identifiable to a skilled person) or aliphatic (e.g. cyclobutane, cyclopentane, cyclohexane, decalin, or others identifiable to a skilled person). The term "attach" or "attached" as used herein, refers to connecting or uniting by a bond, link, force or tie in order to keep two or more components together. Exemplary attachments comprise attachment by bond (e.g. single bond or double bond), by atom (e.g. in spirane-like moieties), fusion (e.g. fused rings) and additional attachment identifiable by a skulled person In some embodiments, the central ring can comprise an aromatic, a heteroaromatic, an aliphatic, or a heteroaliphatic ring. In some embodiments, each of the exterior rings can comprise an aromatic, a heteroaromatic, an aliphatic, or a heteroaliphatic ring. According to some embodiments, each of the exterior rings is connected to the central ring, for example, through a single bond. In particular, in some embodiments, the rigid base linker can comprise a central with the external rings at 1,2-, 1,3-, 1,4-, or 1,3,5 positions around the central substituted benzene ring or a spirane-type moiety.

In particular the central ring and exterior rings can be selected to have a restricted rotation for an amount of time during which the rigid linker is configured to be used. For example, if a linker is part of a complex suitable to catalyze an olefin polymerization the central ring and exterior rings can be selected to have a restricted rotation for an amount of time during which the polymerization occurs. Selection of suitable rings can also be performed so that each exterior ring has a different restricted rotation barrier related to the central ring. For example if a linker is part of a complex suitable to catalyze synthesis of stereoblock copolymers the substitution on the central ring can be selected such that a lower rotational barrier of one exterior ring with respect to another about the central ring is provided so that by varying temperature the configuration of the complex is modified to allow polymerization of the desired block copolymers.

In some embodiments, one or more of the central ring and the exterior rings comprised within the rigid base linker can be substituted with suitable groups to restrict rotation of one or more of the exterior rings with respect to the central ring and control rigidity of the base linker as will be understood by a skilled person. Exemplary position where the groups can be located in each substitute ring are identifiable based on the specific central ring and exterior ring forming the linker and typically comprise ortho positions with respect to the linkage between the central ring and exterior rings.

In some embodiments, the groups substituting one or more position of at least one ring of the rigid linker herein described can comprise steric bulk. Steric bulk in a rigid linker can provide for example by providing groups on the central ring and/or on the exterior rings of the linker to obtain a moiety having restricted rotation. Exemplary groups suitable to provide steric bulk comprise ethers, thioethers, halides, alkyls, aryls, and others identifiable to a skilled person upon a reading of the present disclosure. For example, in embodiments, wherein the central ring is an arene an ortho-substitution (e.g. with alkyl groups), on the exterior rings can provide restricted rotation of the exterior rings about the central ring resulting in distinct atropisomers of the molecule (See e.g. Example 5).

Selection of suitable alkyl groups can be performed based on the restricted rotation desired. For example on ortho substitution with methyl of the arene ring in an exemplary linker comprising two exterior rings, can provide atropisomers which have rotational barriers such that the atropisomers are expected not to detectably interconvert (e.g. having a rotational barrier such that a rate constant for rotation is $k<5\times10^{-6}$ at 373 K) up to temperatures of at least 100° C. (See e.g. Example 5).

A further exemplary rigid linker having a rotational barrier equal to or higher than 25 Kcal/Mol comprises a permethylated central ring. Additional compounds having additional rotation barriers are identifiable by a skilled person In some embodiments, each of the two or more exterior rings attaches a metal-presenting arm. In these embodiments, the two or more exterior rings define two or more metal-presenting arms in a syn position with respect to the rigid base linker.

The term "metal-presenting arm" as used herein refers to a moiety comprising a metal, and an ancillary ligand, and which is capable of binding one or more auxiliary ligands through one or more auxiliary ligand bonds. The term "metal" as used herein refers to atoms and/or ions of elements of the periodic table that are classified as metals and can include, for example, members of groups 1-12, certain members of groups 13-16 (e.g. Al, Ga, In, Sn, and others identifiable to a skilled person), f-block elements such as U, Nd, Lu, Sm, La, Yb, and Er ([Ref 2]) and others identifiable to a skilled person. In particular, in some embodiments, the metals are metal suitable for polymerization of olefins and can include, but are not limited to, nickel (See e.g. Examples 6-7), titanium (See e.g. Examples 8-9), zirconium (See e.g. Example 8), yttrium, hafnium, cobalt, iron, palladium, aluminum, zinc, indium, gallium, and lanthanide metals. In some embodiments, the metals can be different, thus providing a heterometallic system.

The term "ligand" as used herein refers to an ion or molecule that can form covalent and/or dative bonds with metal atoms and/or ions, and in particular with the metal atoms and/or ions of the multi-metallic organometallic complexes herein described. The bonding between metal and ligand generally involves formal donation of one or more of the ligands' electron pairs located on one or more atoms of the ligand. A ligand with only one atom that can form covalent and/or dative bonds with metal atoms and/or ions is a monodentate ligand, and a ligand with more than one atom that can form covalent and/or dative bonds with metal atoms and/or ions is a multidentate ligand.

The term "ancillary ligand" as used herein refers to an anionic or neutral donating ligand attached to rigid base linker and serves to hold the metal atom and/or ion in the metal presenting arms. Such ancillary ligands can include ligands that are known to support monometallic catalysts. Exemplary ancillary ligands can include, but are not limited to, phenoxy-imine, phenoxyimine with a pendant thioether, phenoxy-cyclopentadienyl, diamino-bis(phenolate), amino-bis(phenolate) with a pendant ether donor and others identifiable to a skilled person upon a reading of the present disclosure. In some embodiments, steric and electronic properties of the multi-metallic organometallic complexes herein described can be controlled by changing size and electronic properties of the ancillary ligands.

The term "auxiliary ligand" as used herein refers to additional anionic or neutral ligands that are not attached to the rigid base linker and can stabilize a metal center (e.g. a metal atom or ions) by filling a coordination sphere of the metal atom or ion and/or by balancing the charge depending on the oxidation state of the metal and the type of ancillary ligands bound to the metal. Exemplary auxiliary ligands include, but are not limited to, alkyl, halide, phosphine, N-heterocyclic carbene, amine or alkoxy ligands. In some embodiments, the auxiliary ligands can be methyl, benzyl, chloride, isopropoxide, pyridine, trimethylphosphine, isopropoxide, chloride, oxide ligands, $PF_6^-$, or fluorinated borates.

According to some embodiments, in a metal presenting arm, at least two ancillary ligands are attached to the metal and optionally attached one with the other. In some embodiments the metal presenting arm further comprises one or more auxiliary ligands attached to the metal. In particular, in some embodiments, the metal presenting arms can comprise 2 to 5 ancillary ligands, 1 to 4 auxiliary ligands for each metal comprised in the metal presenting arm. In embodiments herein described the metal presenting arm is attached to an exterior ring of rigid base linker, in particular by attaching at least one ancillary ligand comprised in the arms.

In embodiments of multi-metallic organometallic complexes herein described, each metal-presenting arm of the two or more metal-presenting arms comprise one or more ancillary ligands presenting the metal and the metal is bound to one or more auxiliary ligands through respective one or more auxiliary ligand metal bonds.

In these embodiments each of the one or more auxiliary ligand metal bonds is adapted to be represented through a corresponding one or more auxiliary ligand metal bond three-dimensional vectors which originate at the metal.

In multi-metallic organometallic catalysts according to the present disclosure a rigid base linker and two or more metal presenting arms are selected and configured so that the one or more auxiliary ligand metal bond three-dimensional vectors have a resulting vector located inside an imaginary sphere having a diameter defined by the metal-to-metal distance between metal in the multi-metallic organometallic complex.

Figure 1:
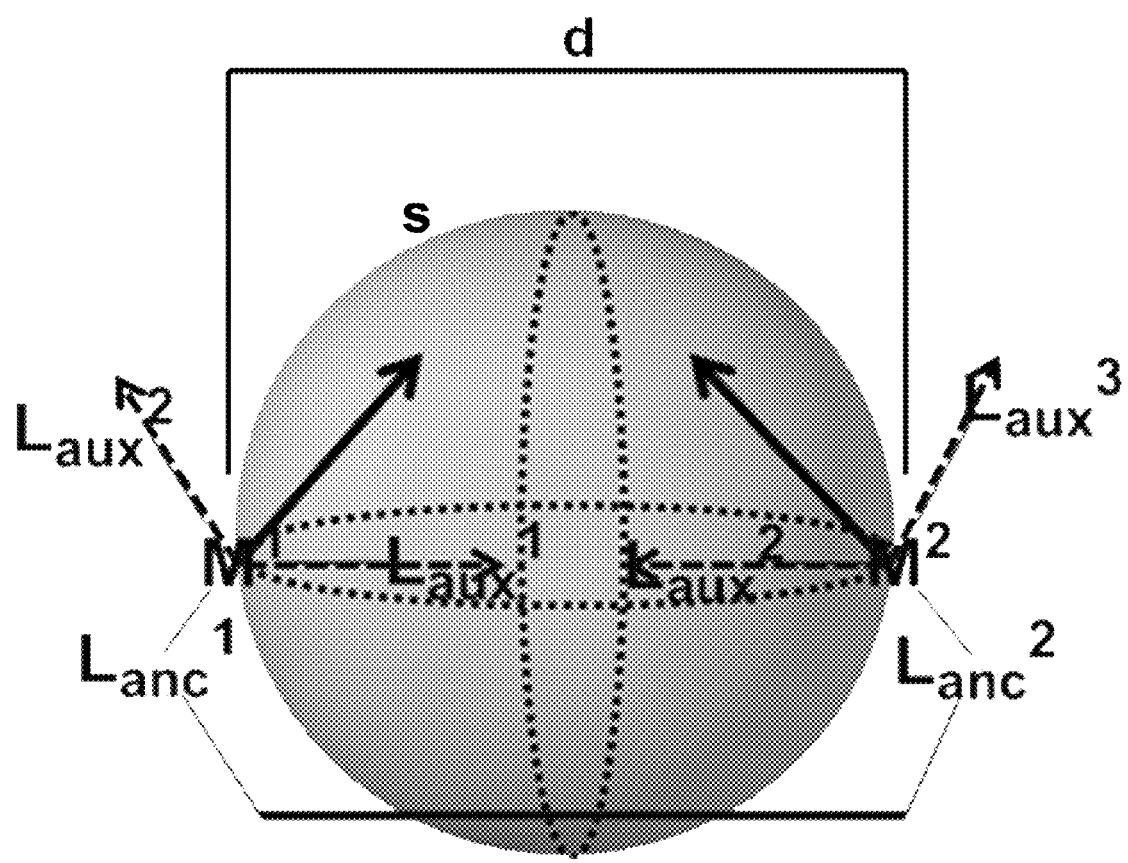
FIG. 1 shows a three-dimensional schematic depiction of a sphere with a diameter defined by metals (grey sphere), and vector sums (solid arrows) of vectors (dotted arrows) defined by auxiliary ligands ($L_{aux}^1$-$L_{aux}^4$) of multi-metallic organometallic complexes herein described.

Reference is made to the schematic illustration of FIG. 1 which shows metals ($M^1$) and ($M^2$) that pertain to different metal-presenting arms which are located at a metal-to-metal distance (d) (See FIG. 1). In the illustration of FIG. 1 the metal-to-metal distance (d) define an imaginary sphere (s) having said metal-to-metal distance (d) as a diameter. For each of the metals located at the metal-to-metal distance, one or more auxiliary ligand metal bond correspond to a vector as schematically shown as dashed arrows in the exemplary illustration of FIG. 1. A resulting vector corresponding to a sum of the one or more auxiliary ligand metal bond three-dimensional vectors is located inside the imaginary sphere (see solid arrows in FIG. 1).

Figure 2:
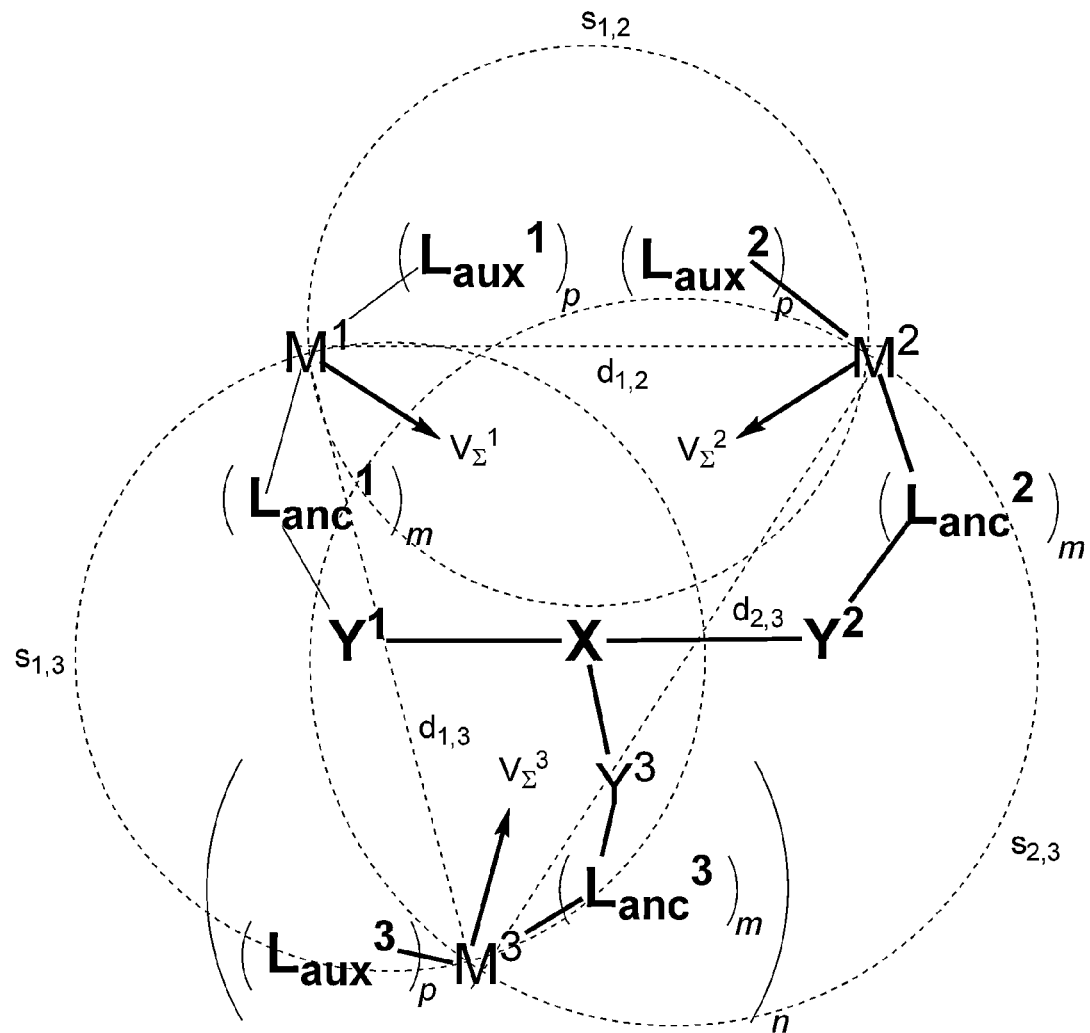
FIG. 2 shows a two-dimensional schematic representation of a multi-metallic organometallic complex as herein described showing the spheres ($s_{1,2}$, $s_{2,3}$, and $s_{1,3}$) with diameters ($d_{1,2}$, $d_{2,3}$, and $d_{1,3}$) defined by the metals, and the vector sums ($V_\Sigma^1$, $V_\Sigma^2$, and $V_\Sigma^3$) of the vectors defined by the auxiliary ligands.

Reference is also made to FIG. 2, wherein the metals $M^1$, $M^2$, and $M^3$ have metal-to-metal distances $d_{1,2}$, $d_{1,3}$ and $d_{2,3}$ defining spheres $s_{1,2}$, $s_{1,3}$, and $s_{2,3}$, and wherein auxiliary ligands $L_{aux}^1$, $L_{aux}^2$ and $L_{aux}^3$ have resulting vectors $V_{\Sigma 1}$, $V_{\Sigma 2}$, and $V_{\Sigma}3$.

A multi-metallic organometallic complex according to the present disclosure can be designed by identifying at least two monometallic complexes each comprising an exterior ring attaching a metal presenting arm (see e.g. the monometallic complexes $(L_{aux}^1)_p$-$M^1$-$(L_{anc}^1)_m$-$Y^1$, $(L_{aux}^2)_p$-$M^2$-$(L_{anc}^2)_m$-$Y^2$, and $(L_{aux}3)_p$-$M^3$-$(L_{anc}^3)_m$-$Y^3$ in FIG. 2), having a resulting vector (e.g. $V_{\Sigma 1}$, $V_{\Sigma 2}$ and $V_{\Sigma 3}$ in the illustration of FIG. 2). A central ring can then be identified (see e.g. (X) in the schematic illustration of FIG. 2) configured to attach the two monometallic complexes with restricted rotation to allow for the resulting vectors to be located within a sphere (see e.g. $s_{1,2}$, $s_{1,3}$ and $s_{2,3}$ of FIG. 2) defined by the metal-to-metal distance of the two monometallic complexes (see e.g. $d_{1,2}$, $d_{1,3}$ and $d_{2,3}$ of FIG. 2).

Figure 37:
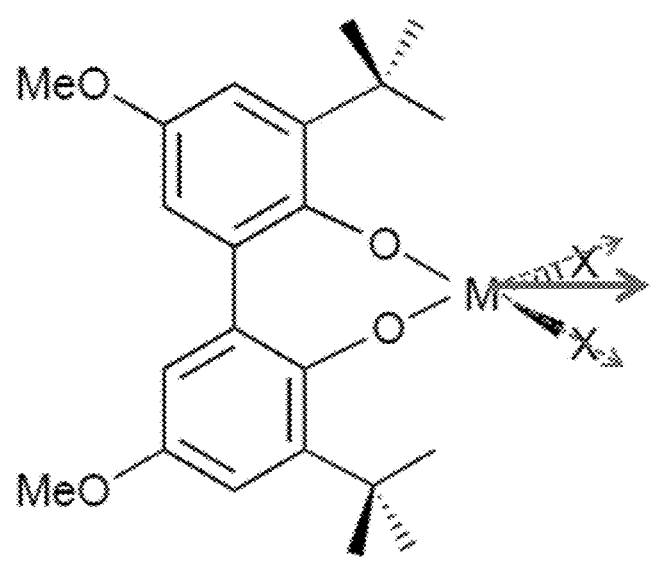
FIG. 37 shows a schematic illustrating auxiliary ligand metal bond three-dimensional vectors of a monometallic organometallic complex and a resulting vector corresponding to a sum of said one or more auxiliary ligand metal bond three-dimensional vector.
Figure 38:
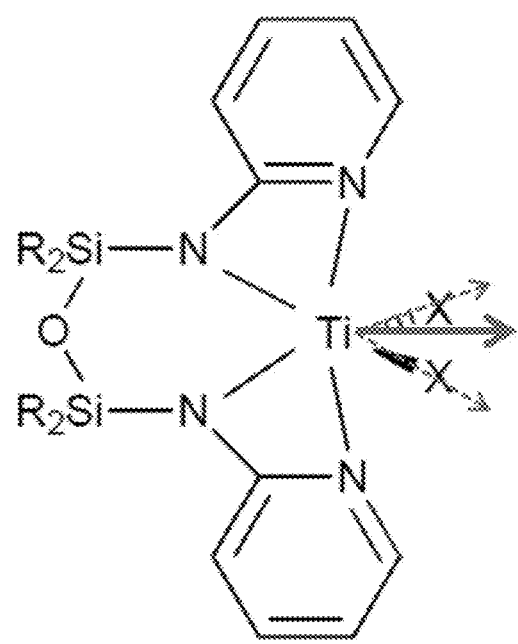
FIG. 38 shows a schematic illustrating auxiliary ligand metal bond three-dimensional vectors and another monometallic organometallic complex resulting vector corresponding to a sum of said one or more auxiliary ligand metal bond three-dimensional vector.

In particular for a given pair of metal presenting arm a central ring can be identified so that a suitable attachment (and optionally substitutions) can be performed at suitable positions in the exterior ring and the central ring to result in the desired restricted rotation. For example for the monometallic complex:

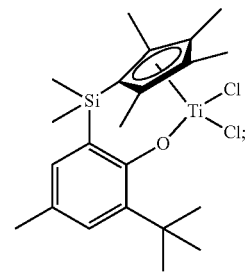

the auxiliary ligand metal bond three dimensional vectors are defined by the Ti—Cl bonds (See e.g. Examples 8-9). (FIG. 37 and FIG. 38 show other exemplary auxiliary ligand metal bond three dimensional vectors of monometallic organometallic complexes defined by metal-auxiliary ligand bonds as well as a the sum of the auxiliary ligand metal bond three-dimensional vectors.) Given two of the titanium based monometallic complex, a suitable central ring can then be selected (e.g. naphatlene) to bind to the phenyl ring of each monometallic complex, at a suitable position of the phenyl ring (e.g. at the ortho position to the oxide ligand). Also possible substitutions of the phenyl ring of each titanium based monometallic complex and/or central ring (e.g. with methyl groups ortho to the bond between the phenyl ring and naphatlene) can be selected to obtain a desired restricted rotation of the phenyl ring relative to the central ring. so that the vectors resulting from the vectors defined by the Ti—Cl bonds are directed towards the center of the imaginary sphere defined by a desired Ti-to-Ti distance.

Figure 33:
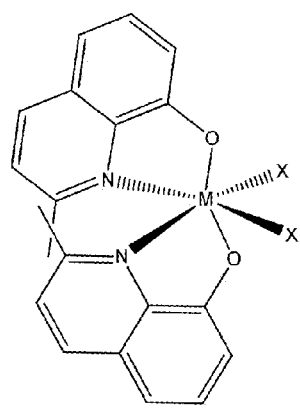
FIG. 33 shows the structure of an exemplary mono-metallic organometallic complex which can be modified to provide a multi-metallic organometallic complex according to some embodiments herein described.
Figure 34:
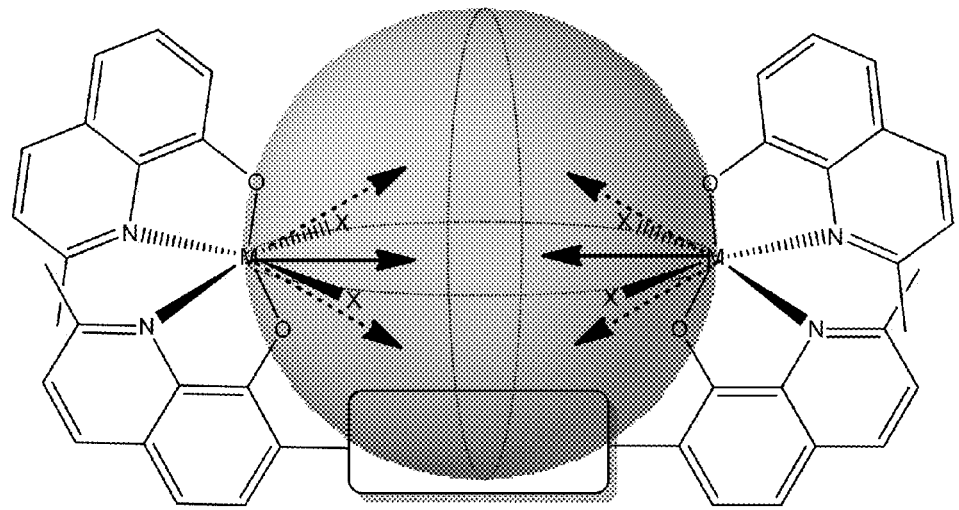
FIG. 34 shows a schematic of multi-metallic organometallic complex according to embodiments herein described. In particular.
Figure 35:
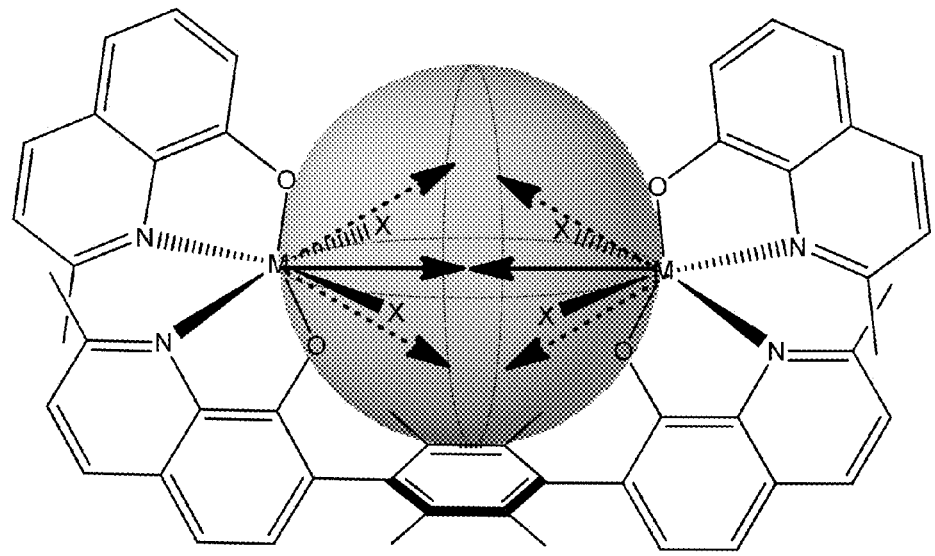
FIG. 35 shows a schematic of the multi-metallic organometallic complex according as shown in FIG. 34 wherein the central ring of the rigid base linker is a permethylated benzene ring.
Figure 36:
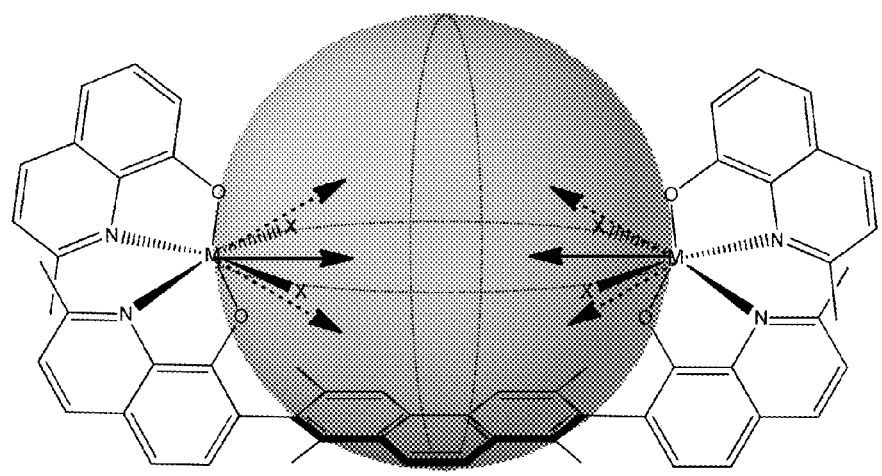
FIG. 36 shows a schematic of the multi-metallic organometallic complex according as shown in FIG. 34 wherein the central ring of the rigid base linker is a substituted phenanthracene ring. Here, the metal-to-metal distance is larger than the metal-to-metal distance of the multi-metallic organometallic complex shown in FIG. 35.

Similarly for a given central ring, suitable metal monometallic complexes (see e.g. FIG. 33) can be identified by selecting monometallic complexes having an exterior ring that when attached to the central ring in at least one position of the monometallic complex and having a restricted rotation of the monometallic complexes about the central ring, provides a desired orientation of the resulting vectors such that vectors are located inside the sphere (See e.g. FIG. 34). For example for a phenyl central ring two monometallic complexes of FIG. 35 can be attached ortho to the oxygen ligand on the aromatic exterior ring of the monometallic complex of FIG. 33 as schematically illustrated in FIG. 35. In the illustration of FIG. 35 the phenyl is permethylated to allow restrict rotation of the monometallic complex about the central phenyl ring. FIG. 36 shows another exemplary embodiment wherein the central ring is a substituted phenanthracene.

Figure 39:
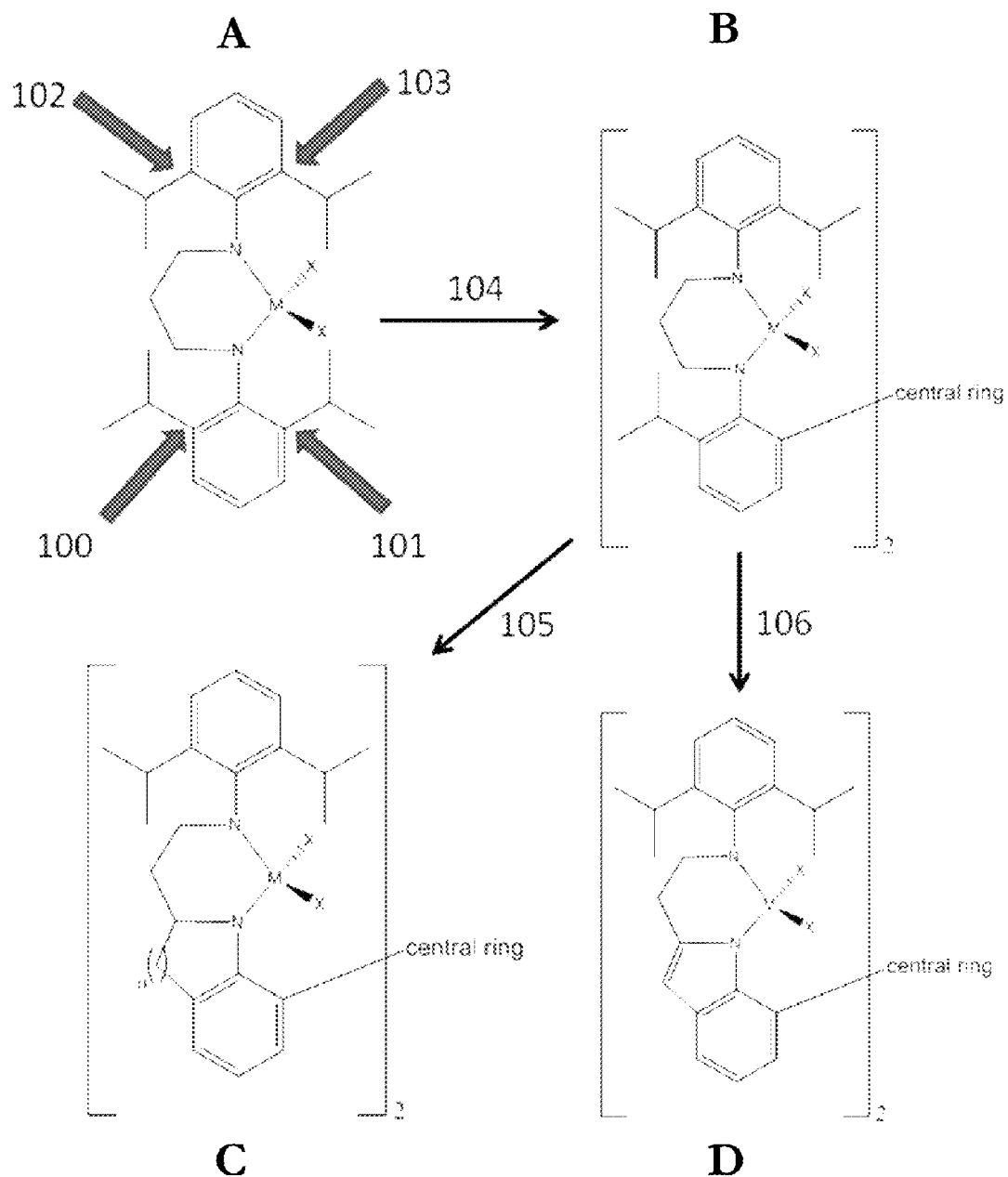
FIG. 39 shows a schematic illustrating modifications of monometallic organometallic complexes as described herein. In particular, Panel A shows positions at which a monometallic organometallic complex can be modified by attaching a central ring according to embodiments herein described. Panel B shows a modified monometallic organometallic complex, modified by attaching a central ring. Panels C-D show exemplary further modifications to provide restricted rotation of the metal comprised in the multi-metallic organometallic complex, thus to providing a multi-metallic organometallic complex according to embodiments of the present disclosure.

FIG. 39 shows a schematic illustrating an exemplary method of selecting modifications of a monometallic organometallic complex according to embodiments herein described. In FIG. 39A a central ring can be substituted in any one of positions (101)-(103) to provide the complex shown in FIG. 39B. The complex shown in FIG. 39B can allow for rotation about the N—C(phenyl) bond and thus can be further modified to restrict rotation and maintain a position of the metal, for example by forming rings according to schematic steps (105) and (106) to provide the complexes in FIG. 39C and FIG. 39D, respectively.

Exemplary multi-metallic organometallic complexes based on monometallic organometallic complexes, include for example, the following:

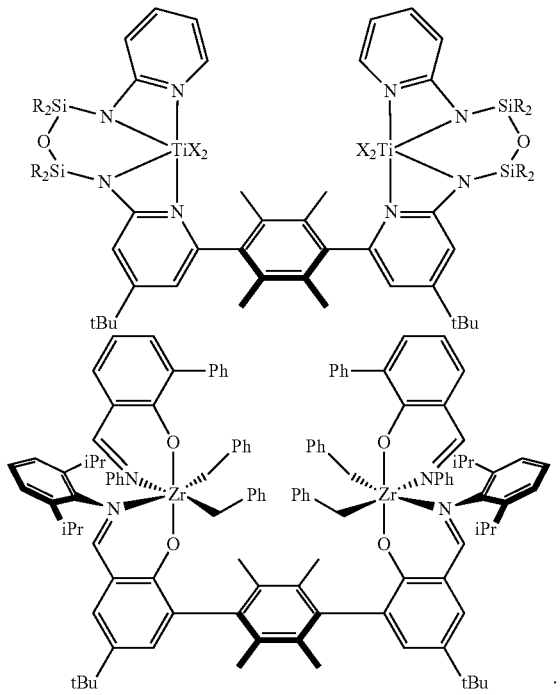

In various embodiments herein described the metal-to-metal distance defining the diameter of the imaginary sphere can be selected based on a desired functionality of the resulting multi-metallic organometallic complex. For example, for a give olefin based reaction, the metal-to-metal distance can be identified to allow coordination of the olefin and/or to allow correct positioning of the metals with respect to the olefin substrate.

In some embodiments, a metal-to-metal distance of the multi-metallic organometallic complex can be set by selecting particular rigid base linker. In particular, a selection of various structural features of the central and/or exterior rings of the rigid base linker can be used to provide a multi-metallic organometallic complex having a particular metal-to-metal distance. In some embodiments metal-to-metal distances according to some embodiments can range from approximately 4 Å to approximately 12 Å.

Metal-to-metal distance according to embodiments herein described can be controlled. For example, a metal-to-metal distance can be increased with increasing size of the central and/or exterior rings. For example, a rigid base linker having a central ring comprising a substituted benzene and two exterior rings each comprising a substituted benzene can provide a shorter metal-to-metal distance than a rigid base linker having a central ring comprising a substituted benzene and two exterior rings each comprising a substituted naphthalene or a rigid base linker having a central ring comprising a substituted naphthalene and two exterior rings each comprising a substituted benzene. Various other central ring structures and exterior ring structures can be independently selected in accordance with a desired metal-to-metal distance as would be understood by a skilled person.

According to further some embodiments, a metal-to-metal distance can be set in connection with a particular substitution pattern of the central ring and/or the exterior rings. For example, for a rigid linker in which the central ring is a substituted benzene ring with exterior rings in para positions, a larger metal-to-metal distance can be provided compared to an analogous rigid linker with exterior rings in ortho or meta positions. For example, the substituted benzene ring with the exterior rings in para positions can provide a metal-to-metal distance which is between approximately 2-4 Å larger than an analogous rigid linker with exterior rings in ortho positions and approximately 1-3 Å larger than an analogous rigid linker with exterior rings in meta positions.

In some embodiments the metal-to-metal distance can be varied by changing the ancillary ligands, for example, from a phenoxyimine to a bulkier phenoxyimine with a pendant donor (see e.g. FIGS. 11(a) and (d), respectively), can change the steric bulk and push the metals farther from one another. For example, providing a methylene between the exterior ring and one or more of the ancillary donors, can allow a change in flexibility and/or geometry that can bring the metals closer together. According to some embodiments herein described, changing one or more of the auxiliary donors can change the metal-to-metal distance of the complex before an activation of the complex while metal-to-metal distances of the active complex can be substantially unaffected by the auxiliary ligands.

In some embodiments, multi-metallic complexes herein described have formula I:

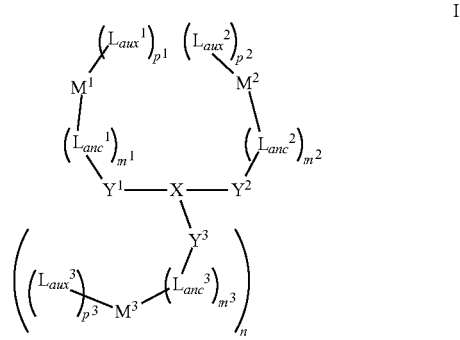

wherein,
n is between 0 and 4;
$m^1$, $m^2$, and $m^3$ are independently between 1 and 4;
$p^1$, $p^2$, and $p^3$ are independently between 1 and 4;
X is the central ring of the rigid base linker herein described;
$Y^1$-$Y^3$ are the exterior rings of the rigid base-linker herein described, $L_{anc}^1$-$L_{anc}^3$ are the ancillary ligands herein described; $M^1$-$M^3$ are the metals herein described; and $L_{aux}^1$-$L_{aux}^3$ are the auxiliary ligands herein described.

In particular, in some embodiments, the central ring has the formula II, III, IV, or V:

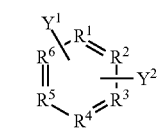

II

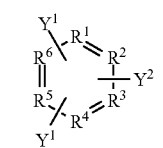

III

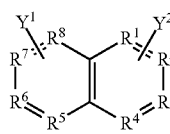

IV

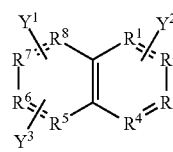

V wherein R1-R8 is independently selected from the group consisting of N, C—H, C-alkyl, C-aryl, C—OMe, C—Y1, C—Y2, and C—Y3 and wherein at least one of R1-R8 in a corresponding ortho position with respect to Y1, and at least one of R1-R8 in a corresponding ortho position with respect to Y2 is not C—H, and at least one of R1-R8 in a corresponding ortho position with respect to Y3 is not C—H or N; and the exterior rings have the formula IX, X, XI, XII, or XIII:

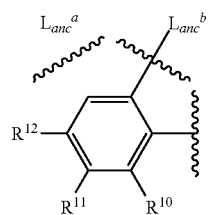

IX

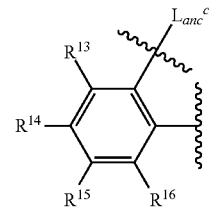

X

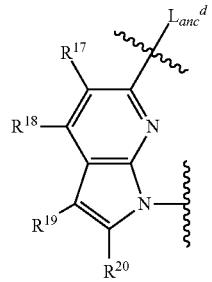

XI

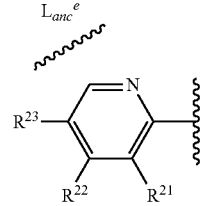

XII

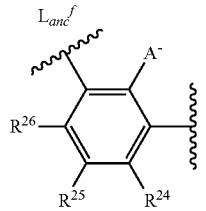

XIII wherein R10-R26 is are selected from the group consisting of H, linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl; and $L_{anc}^a$-$l_{anc}^f$ are the ancillary ligands herein described.

Other central arenes include:

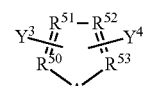

VI

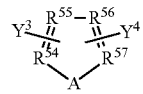

VII

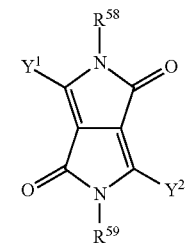

VIII wherein R50-R59 are independently selected from the group consisting of H, N, C—H, C—Y1, C—Y2, C—Y3, C-alkyl, C-aryl, C-alkoxy, and C-aryloxyl; wherein at least one of R1-R8 and R50-57 in a corresponding ortho position with respect to Y1, and at least one of R1-R8 and R50-57 in a corresponding ortho position with respect to Y2 is not C—H, and at least one of R1-R8 and R50-57 in a corresponding ortho position with respect to Y3 is not C—H; A is O, N—H, or S.

In some embodiments, each of the two or more exterior rings are attaching one metal-presenting arm, thus defining two or more metal-presenting arms in syn position with respect to the rigid base linker, wherein each metal-presenting arm of said two or more metal-presenting arms comprises one or more ancillary ligands presenting said metal, said metal is bound to one or more auxiliary ligands through respective one or more auxiliary ligand metal bonds.

In particular, in some embodiments, the ancillary ligands $L_{anc}^1$, $L_{anc}^2$, and $L_{anc}^3$ are independently selected from a monodentate or a multidentate ligand In particular, in some embodiments $L_{anc}^a$ has the formula XIV, XV, XVI, or XVII:

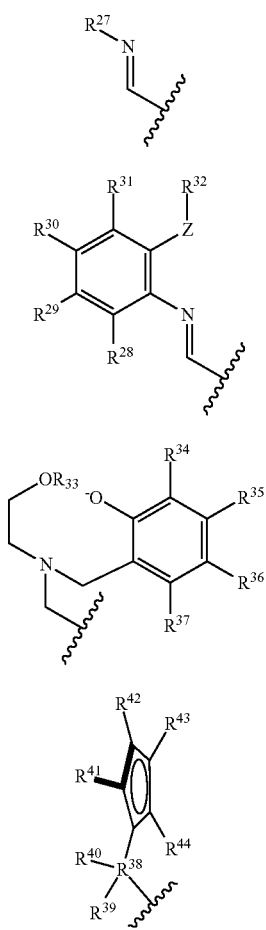

XIV

XV

XVI

XVII wherein
the ligands are attached at the wavy lines to the exterior rings of the rigid base linker herein described.
R27 can be selected from alkyl, aryl, heteroaryl; R28-R37 and R39-44 are selected from the group consisting of H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl, R38 is C or Si. R45 is C, O, N, or a heteroatom; Z=O, S, Se, or N;

$L_{anc}^b$ and $L_{anc}^b$ independently comprise N, O, or C;
$L_{anc}^d$, $L_{anc}^e$, and $L_{anc}^f$ can be, for example:

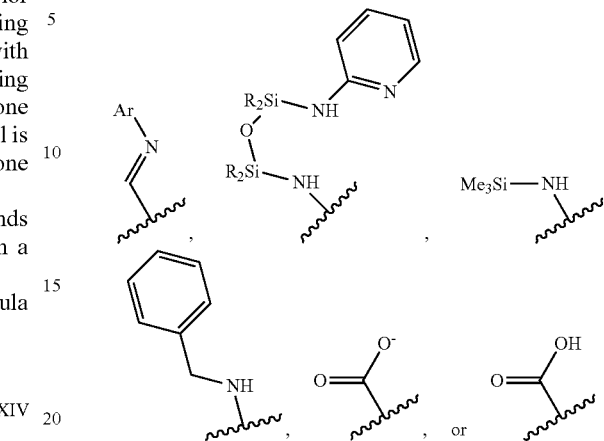

(see, for example, [Ref 3]); and
$L_{aux}$ are the auxiliary ligands herein described and $M^1$, $M^2$, and $M^3$ are independently selected from the group consisting of a main group metal (e.g. indium, gallium, tin, and aluminum), a transition metal (e.g. titanium, zirconium yttrium, hafnium, cobalt, iron, palladium, and zinc), and a lanthanide metal (e.g. U, Nd, Lu, Sm, La, Yb, and Er). In some embodiments, the metals can be a same metal. In other embodiments the metals can be different, thus providing a heterometallic system.

In particular, in some embodiments, the auxiliary ligands are selected from the group consisting of, halides, C1-C2 alkyl, aryl, substituted aryl, phosphines, pyridines, substituted pyridines, amines, imides, hydride, ethers (including THF), benzyl, substituted benzyl, alkoxide.

The term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" can be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "alkoxy" as used herein intends an alkyl group bound through a single, terminal ether linkage; that is, an "alkoxy" group can be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups can contain 5 to 14 carbon atoms. Exemplary aryl groups can contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The terms "cyclic" and "cyclo-" refer to alicyclic or aromatic groups that may or may not be substituted and/or heteroatom containing, and that can be monocyclic, bicyclic, or polycyclic. The term "alicyclic" is used in the conventional sense to refer to an aliphatic cyclic moiety, as opposed to an aromatic cyclic moiety, and can be monocyclic, bicyclic or polycyclic.

The terms "halo", "halogen", and "halide" are used in the conventional sense to refer to a chloro, bromo, fluoro or iodo substituent or ligand.

The term "olefins" as used herein indicates two carbons covalently bound to one another that contain a double bond (sp2-hybridized bond) between them. The other functional groups bound to each of these two carbons can be, for example, additional carbons, hydrogen atoms, or heteroatoms.

The term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO−), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)$_2$), mono-(C5-C24 aryl)-substituted carbamoyl (—(CO)—NH-aryl), di-(C5-C24 aryl)-substituted carbamoyl (—(CO)—N(C5-C24 aryl)$_2$), di-N—(C1-C24 alkyl), N—(C5-C24 aryl)-substituted carbamoyl, thiocarbamoyl (—(CS)—NH2), mono-(C1-C24 alkyl)-substituted thiocarbamoyl (—(CO)—NH(C1-C24 alkyl)), di-(C1-C24 alkyl)-substituted thiocarbamoyl (—(CO)—N(C1-C24 alkyl)$_2$), mono-(C5-C24 aryl)-substituted thiocarbamoyl (—(CO)—NH-aryl), di-(C5-C24 aryl)-substituted thiocarbamoyl (—(CO)—N(C5-C24 aryl)$_2$), di-N—(C1-C24 alkyl), N—(C5-C24 aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, etc.), C2-C20 alkylimino (CR=N(alkyl), where R=hydrogen, C1-C24 alkyl, C5-C24 aryl, C6-C24 alkaryl, C6-C24 aralkyl, etc.), arylimino (—CR=N(aryl), where R=hydrogen, C1-C20 alkyl, C5-C24 aryl, C6-C24 alkaryl, C6-C24 aralkyl, etc.), nitro (—NO2), nitroso (—NO), sulfo (—SO2-OH), sulfonato (—SO2-O−), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)$_2$), boronato (—B(OR)$_2$ where R is alkyl or other hydrocarbyl), phosphono (—P(O)(OH)$_2$), phosphonato (—P(O)(O−)$_2$), phosphinato (—P(O)(O−)), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

In some embodiments, selection of one or more auxiliary ligands in combination with one or more ancillary ligands can be used to provide a particular orientation of the auxiliary ligand metal bond three-dimensional vectors originating at the metal such that the auxiliary ligand metal bond three-dimensional vectors are located inside the imaginary sphere. For example, selection of an oxygen ancillary ligand proximate to the ring in combination with one or more mono- and/or multi-dentate ancillary ligands can provide such an orientation.

In some embodiments, ancillary ligands, auxiliary ligands, and metals comprising the arms can selected from modified monometallic polymerization catalysts. For example, a monometallic organometallic complex can be modified by attaching two or more units of the monometallic organometallic complex to a central ring configured to provide a restricted rotation of the monometallic organometallic units with respect to the central ring, which can allow the metals of a resulting multi-metallic organometallic complex according to embodiments herein described to be held in a set orientation, and in particular, a syn orientation.

For example, a suitable monometallic organometallic catalyst can be selected based on a selected polymerization reaction for which a monometallic organometallic catalyst is configured. For example, a monometallic organometallic complex to be modified in accordance with embodiments herein described can be selected based on attributes associated to the monometallic organometallic complex (e.g. polymerization productivity, compatibility with particular functional groups, length of polymer produced, temperature under which the catalyst can be used, and/or tacticity of structures which can be produced).

For example, according to some embodiments, an multi-metallic organometallic complex has the formula: (modified monometallic organometallic complex)$_2$(central ring).

In particular, in some embodiments, the multi-metallic organometallic complex has the formula: (modified monometallic organometallic complex)$_2$(central ring) wherein the modified monometallic organometallic complex is a polymerization catalyst.

Indicated below is a position (a) on which a monometallic organometallic complex [Ref 4] can be modified (See e.g. Examples 6-7):

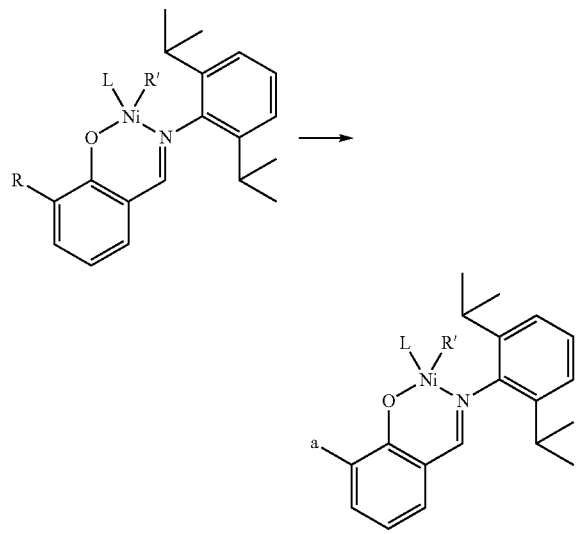

In this example, a is a suitable position of a monometallic organometallic complex on which to attach a central ring of to provide a multi-metallic organometallic complex such that the sum of the auxiliary ligand metal bond three-dimensional vectors can point towards the inside of the sphere of the diameter defined by the metal-to-metal distance in the multi-metallic organometallic complex as the ancillary ligands (O and N) provide a vector sum of the auxiliary ligand metal bond three-dimensional vectors which are located on the inside of the sphere.

According to embodiments herein described, a geometry of the metal center (e.g. if it is tetrahedral, square planar, octahedral) can determine the positions of the auxiliary ligands, and that the number of ancillary ligands can determine the number of auxiliary ligands (e.g. if there are two ancillary ligands and the geometry is square planar, as above, there can be two auxiliary ligands to define the auxiliary ligand metal bond three-dimensional vectors). Therefore, a geometry of the metal center can be used to determine a suitable position of a monometallic organometallic complex on which to attach a central ring of to provide a multi-metallic organometallic complex such that the sum of the auxiliary ligand metal bond three-dimensional vectors can point towards the inside of the sphere of the diameter defined by the metal-to-metal distance in the multi-metallic organometallic complex, In this example, central rings can be, for example, a phenyl or naphthalene ring:

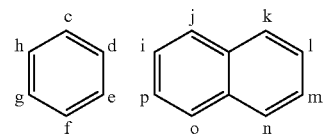

For example for a bimetallic organometallic complex, an attachment of two monometallic organometallic complexes at positions c-h on the phenyl ring and positions i-p can determine the metal-to-metal distance. In some embodiments, one or more of substitutable positions on the central ring can have an alkyl substituent ortho to the position of attachment of the monometallic organometallic complex in order to restrict rotation of the monometallic organometallic complexes with respect to the central ring to maintain the two monometallic organometallic complexes in a syn position and with the sum of the auxiliary ligand metal bond three-dimensional vectors pointing towards the inside of the sphere as exemplified in the following structure:

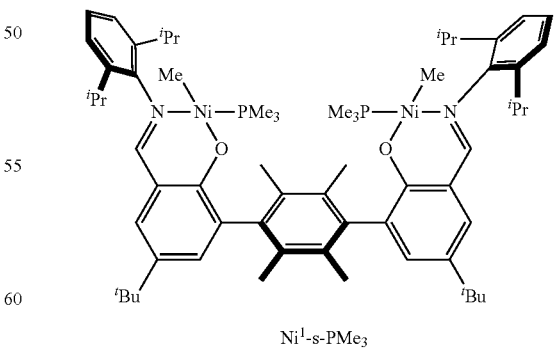

Ni$^1$-s-PMe$_3$

The term "polymerization" as used herein refers to a process in which individual molecules are bonded together to produce larger chains of molecules. The chains or molecules can be linear, or they can be branched three-dimensional networks. The individual molecules to be bonded together are referred to as "monomers," and the larger chain of molecules produced by the polymerization of the monomers is referred to as a "polymer".

In particular, in some embodiments, the monomers used for polymerizations with the multi-metallic organometallic complexes and related methods and systems described herein are olefin monomers and the polymers produced are polyolefin polymers.

The term "olefin" as used herein refers to a chemical compound in which there is at least one carbon-carbon double bond that is not part of an aromatic system. Exemplary olefins include, but are not limited to alkenes such as ethylene, propylene, butylene, isobutylene, styrene, tetrafluoroethylene, and substituted alkenes (e.g. substituted with polar and/or non-polar functional groups, and other alkenes identifiable to a skilled person upon reading the present disclosure; polyenes such as 1,5-hexadiene, and other polyenes identifiable to a skilled person. The olefins can be individual molecules or be part of larger molecules.

The term "polyolefin" as used herein refers to a polymer produced by the polymerization of olefin monomers. Over 100 million tons of polyolefins are produced annually worldwide [Ref 5]. Functionalized polyolefins have a number of desirable physical properties including greater adhesion to substrates and greater compatibility with other materials for use in polymer blends and composites [Ref 5-8]. Industrially, the introduction of polar monomers into polymers can be achieved through radical polymerization or post-polymerization modifications, which in some instances does not allow for a great amount of control over the tacticity of the polymer, polymer branching, insertion rate of co-monomers, or molecular weight of the resultant polymers [Ref 5, 9]. Further, impurities or additives containing functionalities, such as amines, can poison insertion olefin polymerization catalysts.

A metal-to-metal distance of multi-metallic organometallic complexes herein described suitable as olefin polymerization catalyst can be selected based on the distance between the olefinic group and the polar functionality on the desired monomer to be incorporated. The metal-to-metal distance can also be selected based on sterics of the monomer. For example, allyl dipropylamine monomers, a shorter metal-to-metal distance can be used compared to, for example, pentenyl dipropylamine monomers to allow for incorporation of the monomer which is exemplified in the mechanism of FIG. 18.

In particular, in some embodiments the organometallic complexes herein described allow the polymerization of functionalized olefin monomers to produce functionalized polyolefins (See e.g. Examples 21-25, 30-33).

The term "functionalized" with reference to olefins as used herein refers to olefins which are substituted with one or more functional groups (e.g. polar functional groups) such as an oxygen-, nitrogen-, sulfur-, or other heteroatom-containing moieties. Exemplary functionalized olefins include, for example, olefins functionalized with alcohols, ethers, amines, amides, esters, carboxylic acids, acrylate, enones, lactones, lactides, epoxides, aldhyes, ketones, imides, imines, oximes, thiols, thioethers, thiolates and thioesters. In particular, functionalized olefins according to the disclosure can comprise olefins having one or more heteroatoms capable of binding to a metal. With reference to polymerization of olefins, a functionalized olefin is also herein referred to as a "polar mononer". In particular, a polar monomer can comprise a heteroatom such as O, N, S, and/or Cl distal to the olefin (See e.g. Examples 12, 33).

In addition, the aforementioned functional groups can, if a particular group permits, be further substituted with one or more additional functional groups or with one or more hydrocarbyl moieties such as those specifically enumerated above. Analogously, the above-mentioned hydrocarbyl moieties can be further substituted with one or more functional groups or additional hydrocarbyl moieties such as those specifically enumerated.

While many organometallic systems have been developed for polymerization and copolymerization of polar monomers (e.g. functionalized olefins), intolerance to functional groups can limit the scope of functionalized polyolefins that can be produced as well as the rate at which such polymerizations can be catalyzed [Ref 4, 9-14]. For example, an oxophilic nature of early metal catalysts can cause such catalysts to be poisoned by functionalized olefins or other functionalized molecules.

In embodiments wherein catalysts can perform polymerization of polar monomers the metal-to-metal distance can also be selected based on sterics of the monomer. In particular in embodiments where a polar monomer and/or additive has less steric bulk around the polar group was decreased such that the less bulky monomer can bind more easily to a metal center than the more bulky monomer, for example, pentenyl dimethylamine compared to pentenyl dipropylamine, respectively, a shorter metal-to-metal distance in the complex in order to disfavor binding of a polar group to a second metal site and allow polymerization to continue, as exemplified in the mechanism of based of FIG. 18.

For example, in some embodiments, the monometallic organometallic complex [Ref 4] has the structure:

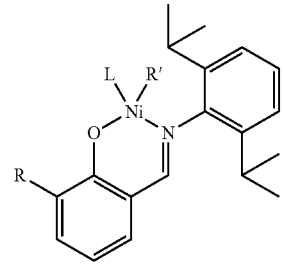

where R=H, tBu, Ph, 9-phenanthroline, 9-anthracene, triphenylmethyl or, terphenyl; R'=Ph or Me; and L=Ph$_3$P or CH$_3$CN (See e.g. Examples 6-7). This monometallic organometallic complex can be selected in embodiments where a high turnover frequencies and/or compatibility with heteroatoms is desired.

In these embodiments, the ancillary ligands, auxiliary ligands, and metals comprising the arms for this type of catalyst are:

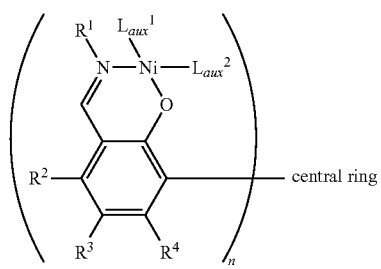

wherein $R^1$-$R^4$=H, alkyl, or aryl group, $L_{aux}^1$ and $L_{aux}^2$ are auxiliary ligands, and n=2-3.

In particular, in these embodiments, the ancillary ligands, auxiliary ligands, and metals comprising the arms for this type of catalyst can be:

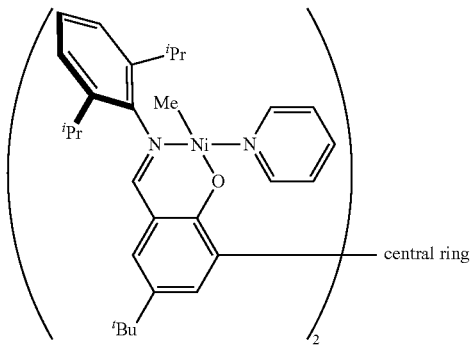

in accordance with the corresponding monometallic organometallic complex (See e.g. Examples 6-7).

In some embodiments, the monometallic organometallic complex [Ref 15] has the structure:

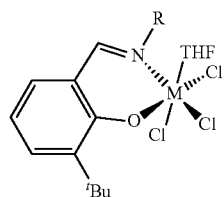

where M=Ti or Zr, and R=phenyl, 2,6-diisopropylphenyl. This monometallic organometallic complex can be selected in embodiments where a high productivity is desired. In these embodiments, the ancillary ligands, auxiliary ligands, and metals comprising the arms can comprise:

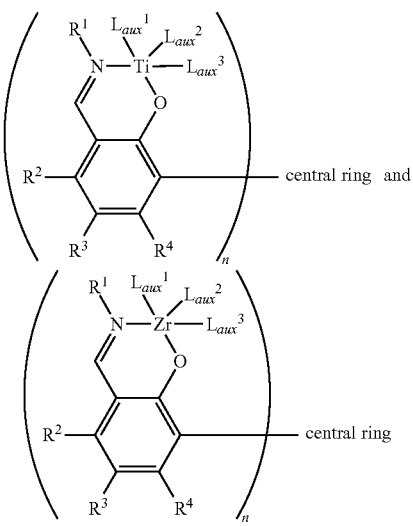

where R1-R4=H, alkyl, or aryl group; $L_{aux}^1$-$L_{aux}^3$ are auxiliary ligands; and n=2-3 (See e.g. Example 8).

In particular, in these embodiments the ancillary ligands, auxiliary ligands, and metals comprising the arms for this type of catalyst can be (See e.g. Example 8):

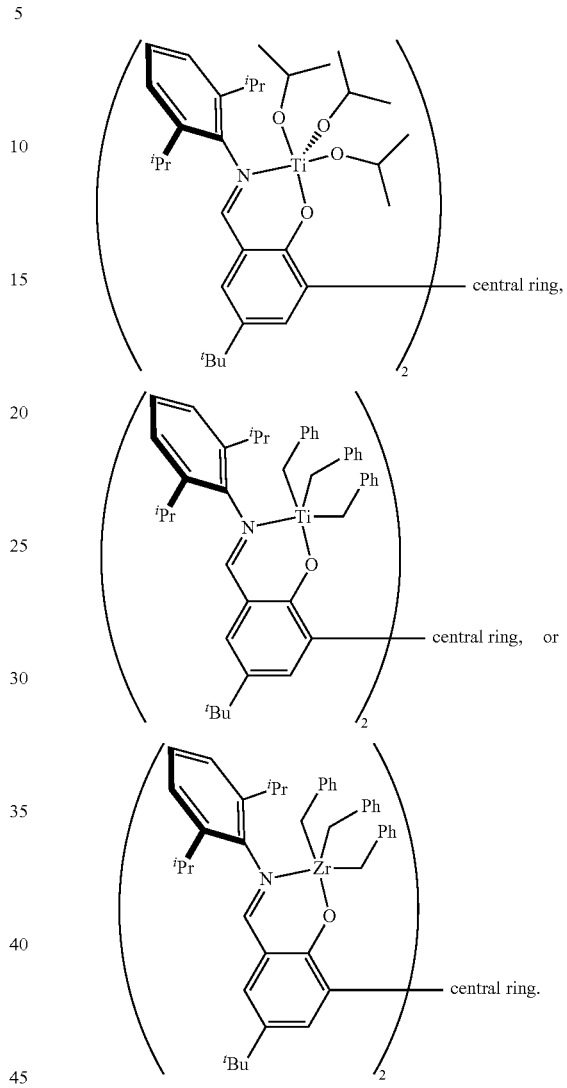

In some embodiments, the monometallic organometallic complex [Ref 16] has the structure:

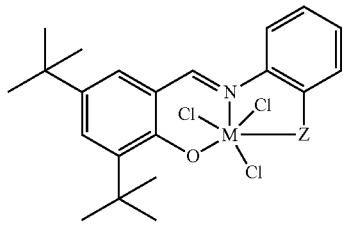

where Z=O, O-alkyl, O-aryl, S, S-alkyl, S-aryl, Se, Se-alkyl, or Se-aryl. This monometallic organometallic complex can be selected in embodiments where high activity in both mono- and copolymerizations is desired. In these embodiments the ancillary ligands, auxiliary ligands, and metals comprising the arms have the structure:

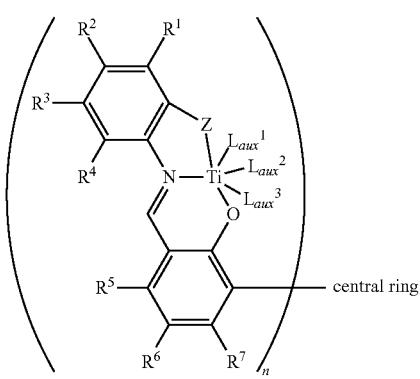

where R1-R7=H, alkyl, or aryl group; $L_{aux}^1$-$L_{aux}^3$ are auxiliary ligands; Z=O, O-alkyl, O-aryl, S, S-alkyl, S-aryl, Se, Se-alkyl, or Se-aryl; and n=2-3 (See e.g. Example 8).

In particular, in these embodiments the ancillary ligands, auxiliary ligands, and metals comprising the arms for this type of catalyst can be (See e.g. Example 8):

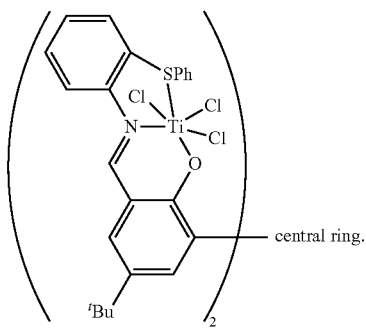

In other embodiments, the monometallic organometallic complex [Ref 17] has the structure (see e.g. Examples 8-9):

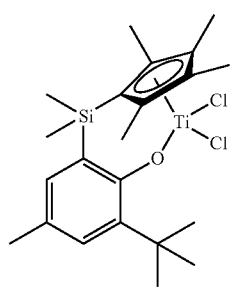

This monometallic organometallic complex can be selected in embodiments where high activity in both mono- and copolymerizations is desired. In these embodiments, the ancillary ligands, auxiliary ligands, and metals comprising the arms have the structure (See e.g. Examples 8-9):

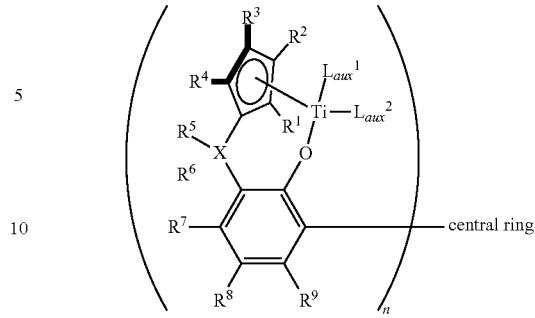

where R1-R9=H, alkyl, or aryl group; $L_{aux}^1$-$L_{aux}^2$ are auxiliary ligands; and n=2-3.

In particular, in these embodiments the ancillary ligands, auxiliary ligands, and metals comprising the arms for this type of catalyst can be (See e.g. Examples 8-9):

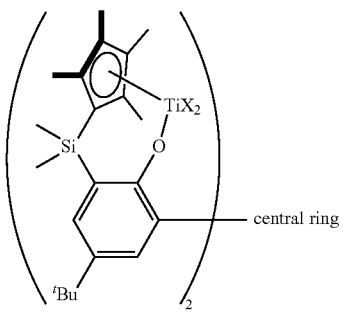

where X=alkyl or halide.

In other embodiments, the monometallic organometallic complex has the structure:

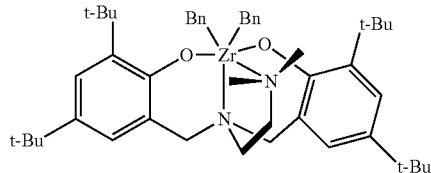

This monometallic organometallic complex can be selected in embodiments where activity in polymerizations of α-olefins is desired. In these embodiments, the ancillary ligands, auxiliary ligands, and metals comprising the arms have the structure (See e.g. Example 10):

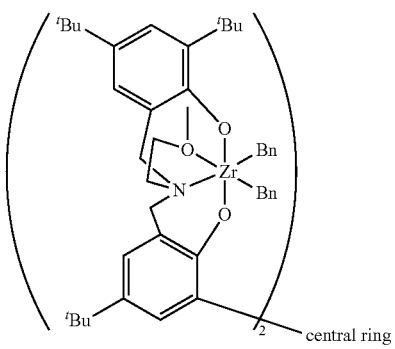

The above examples of using monometallic organometallic complexes modified according to embodiments of the disclosure serve as example embodiments, and other monometallic organometallic complexes having various ancillary ligands, auxiliary ligands, and metals comprising the arms of the multi-metallic organometallic complexes herein described can be used without departing from the scope of the present disclosure and will be apparent to a skilled person.

In some embodiments, the synthesis of the multi-metallic organometallic complexes based on particular monometallic organometallic complexes will be apparent to a skilled person upon a reading of the present disclosure. By way of example, databases (e.g. SCIFINDER® and REAXYS®) can be searched to find commercially available and/or synthesizable starting materials (e.g. aryl boronic acids and/or esters and aryl zinc reagents) for the exterior rings of the multi-metallic organometallic complexes and for the central rings (e.g. aryl halides) as well as appropriate reaction conditions to connect the exterior rings to the interior rings (e.g. Suzuki and Negishi couplings) (see e.g. Examples 1-4, 13-20, 26, and 28).

By way of example, FIG. 2 shows a two-dimensional schematic representation of a multi-metallic organometallic complex as herein described showing the spheres ($s_{1,2}$, $s_{2,3}$, and $s_{1,3}$) with diameters ($d_{1,2}$, $d_{2,3}$, and $d_{1,3}$) defined by the metals, and the vector sums ($V_\Sigma^1$, $V_\Sigma^2$, and $V_\Sigma^3$) of the vectors defined by the auxiliary ligands.

Figure 3:
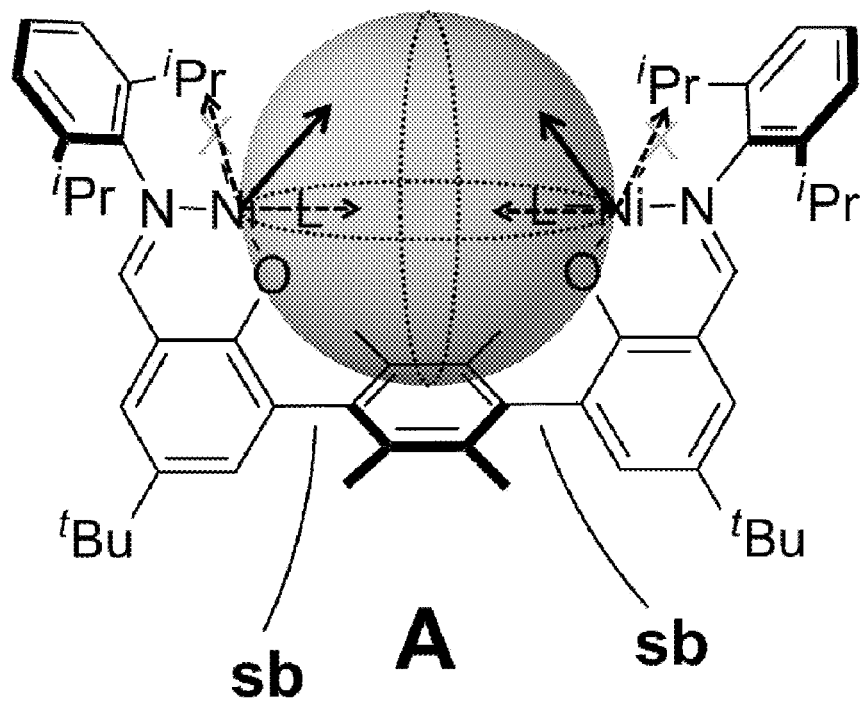
FIG. 3 shows a three-dimensional schematic depiction of an exemplary embodiment of a multi-metallic organometallic complex herein described showing the sphere with diameter defined by the metals (grey sphere), and the vector sums (solid arrows) of the vectors (dotted arrows) defined by the auxiliary ligands (X and L).

By way of example, FIG. 3 shows an exemplary embodiment wherein an oxygen ancillary ligand proximate to the ring in combination with a mono-dentate ancillary ligand comprising an imine which provides an orientation of the auxiliary ligand metal bond three-dimensional vectors in which the sum thereof is located inside the imaginary sphere according to embodiments herein described. In particular, FIG. 3 shows the sphere with diameter defined by the metals (grey sphere), and the vector sums (solid arrows) of the vectors (dotted arrows) defined by the auxiliary ligands (X and L).

In some embodiments, the metal-to-metal distance of the multi-metallic organometallic complexes can be selected based on a particular reaction for which the multi-metallic organometallic complex is to be used (See e.g. Examples 21-25, 30-33).

For example, if the reaction is a polymerization reaction of a polar monomer, the structure of the polar monomer to be polymerized can be used to determine a desired metal-to-metal distance.

In other embodiments, the metal-to-metal distance of the multi-metallic organometallic complexes can be selected based on a particular metal-binding polar additive or a metal-binding polar impurity which is present or formed during a reaction for which the multi-metallic organometallic complex is to be used.

Figure 31:
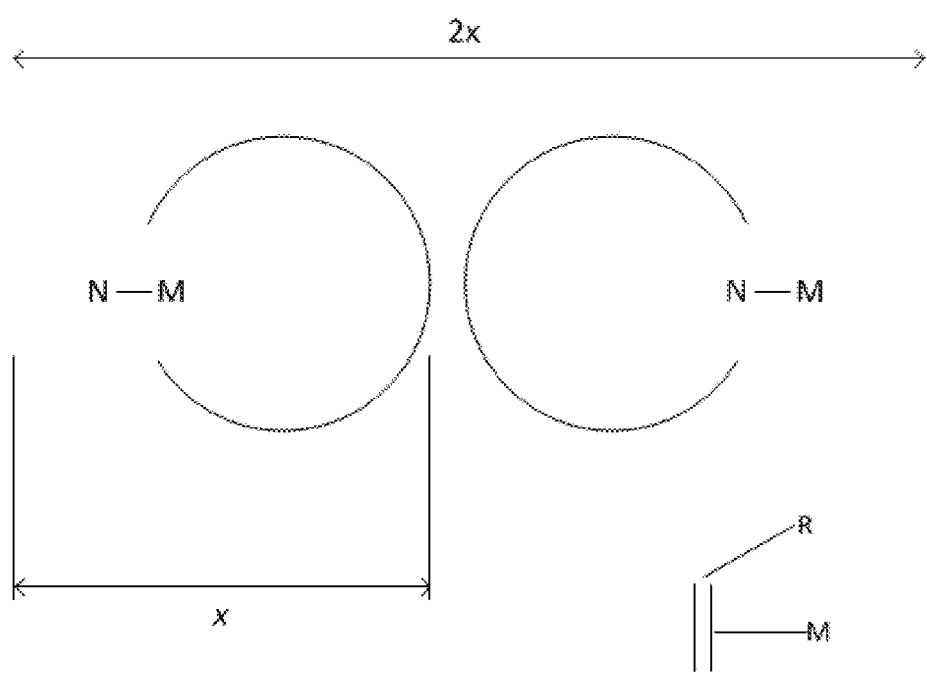
FIG. 31 shows a schematic showing how a metal-to-metal distance can be selected based on the size of a smallest non-hydrogen substituent of a metal-binding heteroatom. In particular.

For example, given a particular functionalized monomer, polar additive, or polar impurity, the metal-to-metal distance of the multi-metallic organometallic complex can be set such that the distance between the metals is approximately two times the distance between a metal-binding heteroatom on the functionalized monomer, the polar additive, or the polar impurity, and a smallest non-hydrogen substituent on the metal-binding heteroatom of the functionalized monomer, the polar additive, or the polar impurity, respectively (see e.g. FIG. 31). In these embodiments, the set metal-to-metal distance is configured to allow binding between the binding moiety of the monomer and a first metal of the multi-metallic organometallic complex and to allow interaction of the olefin comprised in the monomer with a second metal in the same multi-metallic organometallic complex.

In some embodiments, the size of the of the smallest non-hydrogen substituent on the on the metal-binding heteroatom can be determined by calculating a distance between the binding moiety of the functionalized olefin and a most distal atom on the smallest non-hydrogen substituent on the binding moiety. According to some embodiments, such distance can be determined by in connection with bond lengths and bond angles of the functionalized olefin. Bond lengths and bond angles can be determined, for example, by searching the Cambridge Structural Database or other databases identifiable by a skilled person. Other methods for determining a distance between a distance between a binding moiety of the functionalized olefin and a most distal atom on the smallest non-hydrogen substituent on the binding moiety are identifiable by a skilled person and include, for example, molecular modeling (e.g. SPARTAN®, GAUSSIAN®).

Determination of a distance between a distance between the binding moiety of the functionalized olefin and a most distal atom on the smallest non-hydrogen substituent on the binding moiety is now described by way of example, for the following functionalized olefin monomer:

Figure 32:
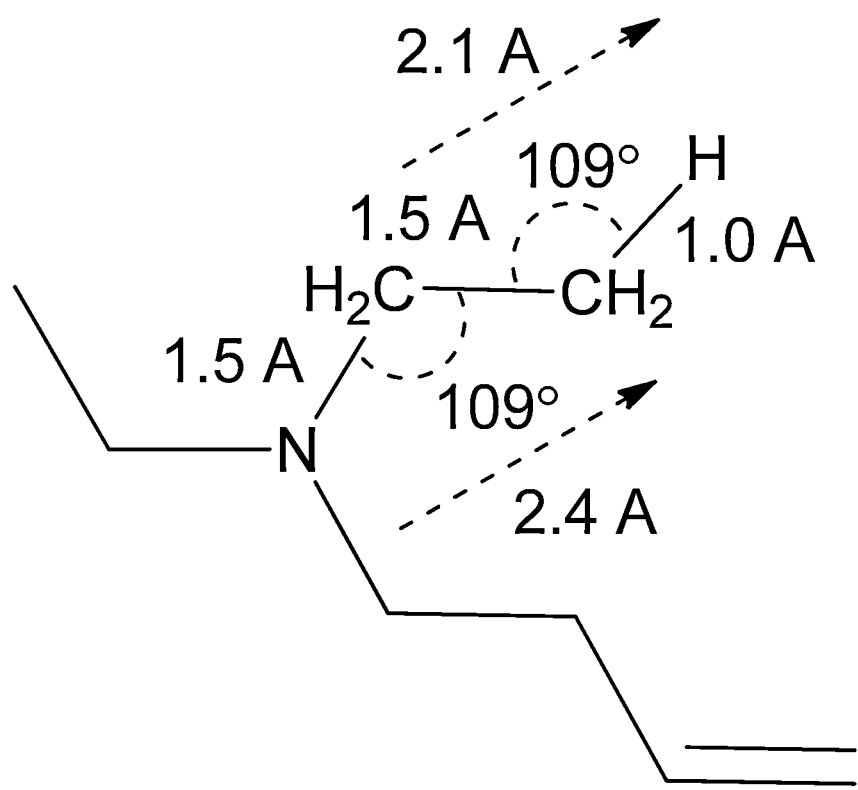
FIG. 32 shows a schematic illustrating calculated distance based on bond lengths and bond angles according some embodiments.

In this example, the distance between the heteroatom and the and the furthest atom on the smallest non-hydrogen substituent on the metal-binding heteroatom can be calculated as approximately 4.5 Å, for example, as calculated based on the law of cosines as exemplified in FIG. 32.

Accordingly, in this example, the metal-to-metal distance can be set at slightly less than 9.0 Å, for example approximately 8-8.9 Å, or another distance less than 9.0 Å which allows for binding of the nitrogen heteroatom at a first metal of the multi-metallic organometallic complex and binding of the olefin at a second metal of the multi-metallic organometallic complex.

An exemplary set of ancillary ligands, auxiliary ligands, and metals comprising the arms of the multi-metallic organometallic, configured to allow such metal-to metal distance comprise:

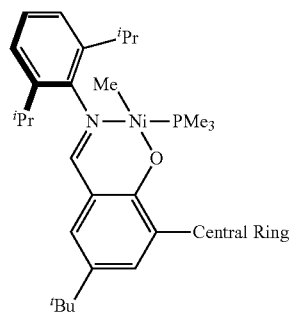

which can provide a multi-metallic organometallic complex having the structure:

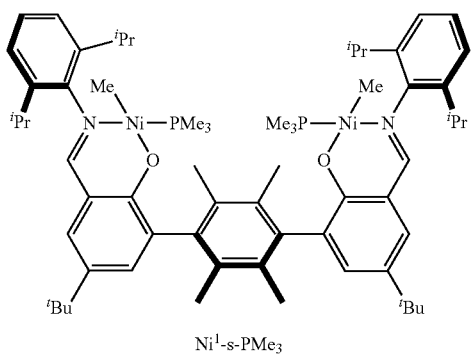

Ni¹-s-PMe₃ thus providing a metal-to-metal distance of approximately 8.9 Å as determined by x-ray crystallography (See e.g. Examples 6-7).

Figure 13:
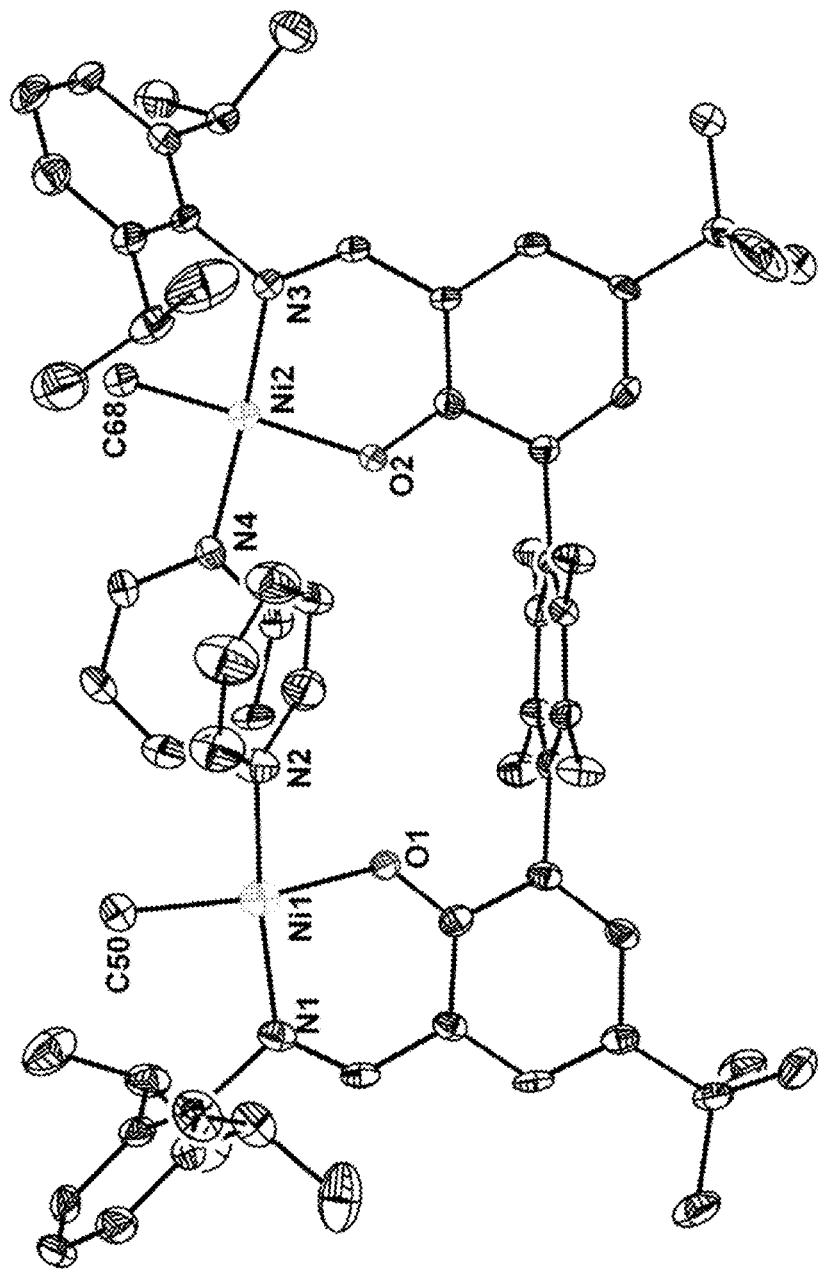
FIG. 13 shows solid-state structures of multi-metallic polymerization catalysts according to an embodiment herein described, and in particular the solid-state structure of $Ni^1$-s-pyridine.

In embodiments herein described, the metal-to-metal distance for a particular multi-metallic organometallic complex can vary based on the structure of the auxiliary ligands. For example, more sterically hindered auxiliary ligands (e.g. PMe₃) can increase the metal-to-metal distance, less sterically hindered auxiliary ligands (e.g. pyridyl) can provide a metal-to-metal distance which is approximately a same metal-to-metal distance as if no auxiliary ligands were present (see e.g. FIG. 13 showing a multi-metallic organometallic complex having a metal-to-metal distance of approximately 7 Å, FIG. 14(b) showing a multi-metallic organometallic complex having a metal-to-metal distance of approximately 7.226 Å, and FIG. 15 showing a multi-metallic organometallic complex having a metal-to-metal distance of approximately 3.68 Å). Therefore, according to embodiments herein described, a desired metal-to-metal distance of the multi-metallic organometallic complex can be selected to account for an increase or decrease of the metal-to-metal distance upon displacement of one or more auxiliary ligands (e.g. during polymerization of a functionalized olefin).

In embodiments herein described, the metal-to-metal distance for a particular multi-metallic organometallic complex can vary based on the structure and/or substitution pattern of the central ring. For example, in the Ni-s-PMe₃ structure, the metal-to-metal distance of the can be increased, for example, by using a methylated naphthalene ring for the center ring or can be decreased, for example, by placing the exterior rings at meta or ortho positions on the center ring.

Other structural variations to increase or decrease the metal-to-metal distance of a particular multi-metallic organometallic complex of the disclosure are identifiable by a skilled person and can allow controlled variation of the metal-to-metal distance.

According to further embodiments, a monometallic organometallic complex can be selected in accordance with a desired reactivity of the monometallic organometallic complex (e.g. a monometallic organometallic complex which provides a desired type of polymerization).

According to further embodiments a metal-to metal distance of a particular multi-metallic organometallic complex selected by preparing one or more multi-metallic organometallic complexes, each having a different metal-to-metal distance (e.g. by varying size and/or substitution pattern of the central ring) and performing a selected polymerization with each multi-metallic organometallic complex. Based on a desired outcome of each polymerization reaction (e.g. a desired reaction yield, turnover frequency, polymer length) a metal-to-metal distance can be selected in connection with the multi-metallic organometallic complex providing the desired outcome of the polymerization reaction.

According to some embodiments, a metal-to-metal distance of a multi-metallic organometallic complex can be determined, for example, by X-ray crystallography (See e.g. Example 29).

In some embodiments the multi-metallic organometallic complex has a formula according to formula shown in FIG. 4.

Also provided herein, a method for preparing polyolefins is described, the method comprising contacting an olefin monomer with the organometallic complexes herein described. In some embodiments, the olefin monomer contacted with the organometallic complexes herein described is a polar olefin monomer. In other embodiments, the polyolefin produced is a polyolefin copolymer. In other embodiments, the polyolefin produced is a block copolymer.

In some embodiments, the olefin monomer contacted with the organometallic complexes herein described is a polar olefin monomer. In other embodiments, the polyolefin produced is a polyolefin copolymer. In other embodiments, the polyolefin produced is a block copolymer.

In some embodiments, the method for preparing polyolefins can be performed in the presence of polar additives with the syn atropisomer of the multi-metallic organometallic complexes herein described because of the multi-metallic effects observed when the metals are in proximity to one another. These polar additives would normally act as inhibitors to polymerization such that the catalysts included herein would be able to do polymerization under less restrictive conditions with respect to purity and functionality of monomer feedstock.

In particular, in some embodiments, the method for preparing polyolefins can be performed for the copolymerizing of polar olefin monomers with ethylene. Exemplary co-polymers can include, but are not limited to, copolymers with tertiary amines including N,N-di-n-propyl-pentenylamine and N,N-diethyl-pentenylamine. Additional functionalized monomers can include olefins with amine, amide, imide, alcohol, acrylate, ether, ester, carboxylate, thiolate, or thioether moieties or non-olefinic monomers such as epoxides, carbon monoxide, carbon dioxide, lactones and lactides [Ref 6, 18]. Additional functionalized monomers can include metal-binding monomers (such as, for example, olefins with a bipyridine moiety) for the synthesis of metal containing polymers,[Ref 19, 20] or chiral monomers (for example, olefins containing amino acids, peptides, or sugars) for the synthesis of chiral polymers [Ref 21]. Other monomers included vinyl and ally monomers.

Also provided herein, a catalytic system for olefin polymerization is described, the system comprising one or more of the mono-metallic organometallic complexes herein described and an olefin monomer. In some embodiments, the system further comprises a suitable activator.

In some embodiments, the catalytic system can include an activator or scavenger. Ni(COD)₂ can be used in cases where M=Ni and X=PMe₃ as a phosphine scavenger. In some embodiments, for example where M is an early transition metal, methylaluminoxane (MAO), a modified MAO, borates (e.g. trityl borate ([Ph₃C][B(C₆H₃(CF₃)₂)₄]) anilinium borate ([PhNHMe₂][B(C₆F₅)₄])), boranes (e.g. fluorinated boranes (B(C₆F₅)₃)), and non-coordinating anions can be used as activators. Chain transfer agents such as Al(ⁱBu)₃ can also be used. In other embodiments the multi-metallic organometallic complex comprised in the catalytic system can also be self-initiating, not requiring the addition of an activator.

Also provided herein, a method for preparing an organometallic complex is described, the method comprising selecting a central ring; selecting two or more exterior rings, the exterior rings; contacting the central ring with the two or more exterior rings to provide a rigid linker; selecting one or more ancillary ligands, one or more metals, and one or more auxiliary ligands; contacting the rigid linker with the one or more ancillary ligands to provide an organometallic complex precursor; contacting the organometallic complex precursor with the one or more metals and auxiliary metals to provide the organometallic complex.

Also described herein are functionalized polyolefins. According to some embodiments, multi-metallic organometallic complex of the disclosure can be used to polymerize functionalized olefin monomers to obtain such functionalized polyolefins.

In some embodiments, the functionalized monomers have the structure:

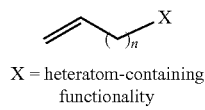

X = heteroatom-containing functionality

In particular, in some embodiments, the functionalized monomers have the structure:

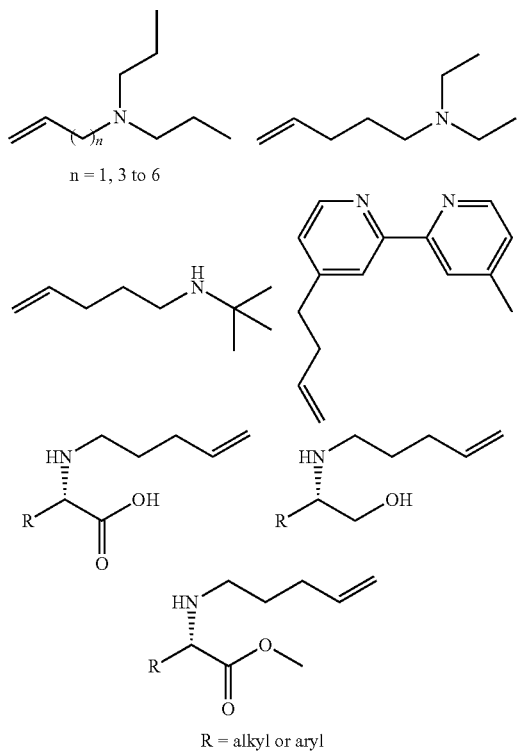

R = alkyl or aryl

In some embodiments, the functionalized polyolefins have the structure:

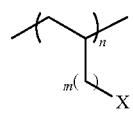

where m=1 or 3-6 and n=150-500 and X comprises a polar functional group such as alcohol, ether, amine, amide, ester, carboxylic acid, acrylate, enone, lactone, lactides, epoxide, aldhye, ketones, imide, imine, oxime, thiol, thioether, thiolate and thioester or other moiety comprising a nitrogen, oxygen, or sufur, for example.

In particular, in some embodiments, the functionalized polyolefins comprise:

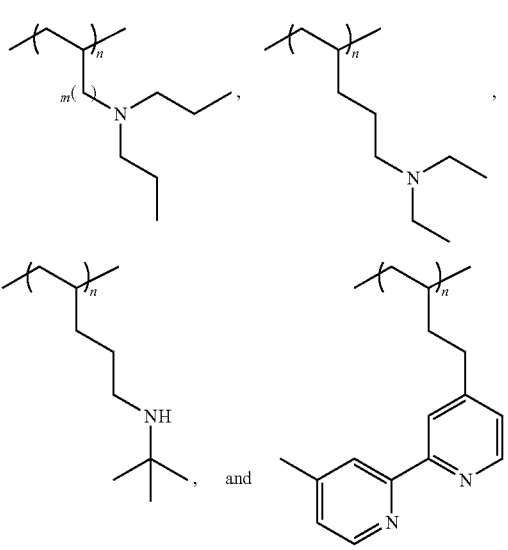

where n=150-500.

Additional exemplary functionalized polyolefins comprise:

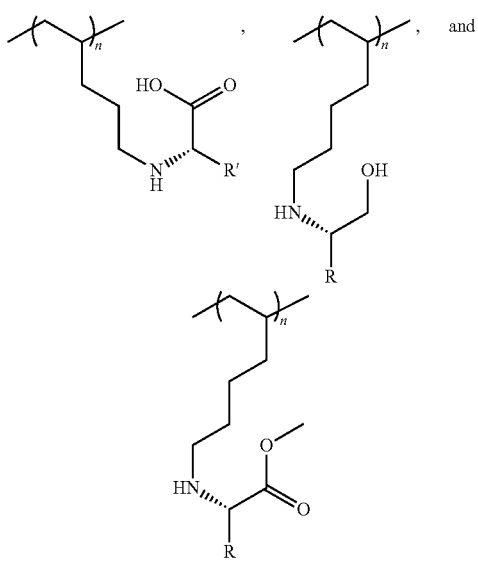

where R'=an amino acid side group, an alkyl group, or an aryl group and n=150-500.

In some embodiments, the functionalized olefin monomers can be co-polymerized with non-functionalized olefin monomers (e.g. ethylene) to functionalized co-polymers:

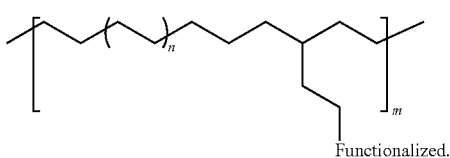
Functionalized.

Amino acids according to the disclosure can include both natural and non-natural amino acids.

According to some embodiments, multi-metallic organometallic complexes herein described can be used as catalysts for polymerization of olefins,[Ref 6, 22, 23] epoxides[Ref 24], lactones or lactides; [Ref 24, 25] copolymerization of carbon monoxide and olefins[Ref 26-28]; and copolymerization of carbon dioxide and epoxides [Ref 29] are described. In these embodiments, the multi-metallic organometallic catalysts can be used in connection with providing polyolefins and other polymeric materials. In particular, according to some embodiments, the multi-metallic organometallic complexes herein described organize the metal centers in a well-defined relative orientation for bimetallic reactivity when compared to other multi-metallic catalysts [Ref 23]. Because of the multi-metallic effects observed with the syn atropisomers of these catalysts the co-monomer scope has been expanded to polar olefins.

In some embodiments, the multi-ligand capture agents herein described are comprised in a composition together with a suitable vehicle. The term "vehicle" as used herein indicates any of various media acting usually as solvents, carriers, binders or diluents for the multi-metallic organometallic complexes that are comprised in the composition as an active ingredient. In particular, the composition including the multi-metallic organometallic complexes can be used in one of the methods or systems herein described.

Multi-metallic organometallic complexes described herein can be provided as a part of systems to perform olefin based reactions such as polymerization, oligomerization and additional reactions, identifiable by a skilled person upon reading of the present disclosure.

In some embodiments, the systems to perform olefin based reactions herein described can be provided in the form of combinations of compounds and/or related compositions, in which the compounds can comprise one or more multi-metallic organometallic complexes, as well as additional compounds such as monomers, activators, chemical scavengers, solvents, solid supports and additional elements identifiable by a skilled person.

In some embodiments, the systems to perform one or more olefin based reactions herein described can be provided in the form of kits of parts. In a kit of parts, the multi-metallic organometallic complexes, suitable substrates such as olefin monomers and other reagents to perform the reactions can be comprised in the kit independently. The multi-metallic organometallic complexes can be included in one or more compositions, and each complex can be in a composition together with a suitable vehicle.

In some embodiments, the multidentate organometallic compound described herein can be provided as a part of systems to make multi-metallic organometallic complexes described herein. In particular, systems to produce a multi-metallic organometallic complexes described herein, can comprise at least two of one or more multidentate organometallic compounds, one or more metals, and/or one or more ligands and in particular any auxiliary ligands herein described and/or identifiable by a skilled person upon reading of the present disclosure.

In some embodiments, systems to make one or more multi-metallic organometallic complexes can provided in the form of combinations of compounds and/or related compositions, in which the compound can comprise the at least two multidentate organometallic compounds, metals and/or one or more ligands possibly together with solvents, solid supports and additional elements identifiable by a skilled person.

In some embodiments, the systems to make one or more metallic organometallic complexes herein described can be provided in the form of kits of parts In a kit of parts, one or more multidentate organometallic compounds, metals, ligands and other reagents to perform the reactions can be comprised in the kit independently. The multidentate organometallic compound can be included in one or more compositions, and each compound can be in a composition together with a suitable vehicle.

EXAMPLES

The following examples are disclosed for further illustration of the embodiments and are not intended to be limiting in any way.

General Conditions and Instrumentation

All air- and/or water-sensitive compounds were manipulated using standard vacuum or Schlenk line techniques or in an inert atmosphere glove box. The solvents for air- and moisture-sensitive reactions were dried over sodium benzophenone ketyl, calcium hydride, or by the method of Grubbs [Ref 30]. All NMR solvents were purchased from Cambridge Isotopes Laboratories, Inc. Benzene-$d_6$ was dried over sodium benzophenone ketyl and vacuum transferred prior to use. Pyridine and all monomers and amines were dried over calcium hydride and vacuum transferred prior to use. Trimethylphosphine was dried over 4 Å molecular sieves prior to use. Ethylene was purchased from Matheson and equipped with a PUR-Gas in line trap to remove oxygen and moisture before use. All $^1$H, $^{13}$C, $^{31}$P, and 2D NMR spectra of small organic and organometallic compounds were recorded on Varian Mercury 300 MHz, Varian 400 MHz, or Varian INOVA-500 or 600 MHz spectrometers at room temperature. All $^1$H and $^{13}$C NMR spectra of polymers were recorded on the Varian INOVA-500 MHz spectrometer at 130° C. in tetrachloroethane-$d_2$. Chemical shifts are reported with respect to residual internal protio solvent: 7.16 and 128.06 (t) ppm ($C_6D_6$); 7.26 and 77.16 (t) ppm ($CDCl_3$); 5.32 and 53.84 (q) ppm ($CD_2Cl_2$); for $^1$H and $^{13}$C data.

Example 1

A First Step in Preparing Dinucleating Ligand Sets

The present dinucleating compounds have been prepared using well-precedented procedures. Commercially available and inexpensive 4-tert-butylphenol and mesitylene or 1,2,4,5-tetramethylbenzene are employed as the starting materials for the tri- or tetra-aryl backbone. Dibromination of mesitylene leads to 1,3-aryl-substituted complexes while dibromination of 1,2,4,5-tetramethylbenzene leads to 1,4-aryl-substituted complexes. Bromination ortho to the phenol and protection of the phenol moiety of 4-tert-butylphenol with methyl or methoxymethyl (MOM) protecting groups followed by lithium halogen exchange and reaction with $ZnCl_2$ generates the aryl-zinc reagents suitable for Negishi cross-coupling in situ (FIG. 5 through FIG. 8). 1,3-dibromomesitylene and 1,4-dibromo-2,3,5,6-tetramethylbenzene have been used as coupling partners with $Pd(PPh_3)_4$ as the catalyst.

Aqueous workup, followed in some cases by column chromatography, provides the terphenyl diphenols as white powders or colorless sticky oils.

Example 2

Synthesis of Bisphenoxyiminato Compounds

To synthesize bisphenoxyiminato compounds (FIG. 5 and FIG. 6), directed lithiation with $^n$BuLi and tetramethylethylenediamine followed by the in situ reaction with dimethylformamide yields the bisaldehydes. The phenol moieties are subsequently deprotected using refluxing acidic methanol (to remove the MOM protecting group) and combined with excess 2,6-diisopropylaniline or 2-aminophenyl phenyl sulfide to afford the bisphenoxyimines, $L^1$, $L^2$ and $L^3$, which precipitate as light yellow powders from methanol.

Example 3

Synthesis of Bisphenoxycyclopentadienyl Compounds

To synthesize the bisphenoxycyclopentadienyl compounds (FIG. 7 and FIG. 8), the methyl protecting groups are removed with excess BBr$_3$ at 0° C. in dichloromethane. These bisphenols are brominated in the positions ortho to the phenols using bromine in DCM starting cold (−78° C.) and allowing the reactions to warm to room temperature over several hours. The phenol moieties of the dibromides are reprotected with allyl bromide. Lithium halogen exchange with $^n$BuLi and in situ reaction with dichlorodimethylsilane provides the disilanes, which are then combined with mono-lithiated pentamethylcyclopentadiene to yield the ligand precursors, $L^4$ and $L^5$.

Example 4

Synthesis of Bis-Salan Compounds

The synthesize the bis-salan compounds (FIG. 9), the methyl protecting groups are removed with excess BBr$_3$ at 0° C. in dichloromethane. The benzylbrominated compounds are synthsized from the bisphenols in the positions ortho to the phenols by mixing with paraformaldehyde in glacial acetic acid and bubbling HBr (g) through the reaction mixture. The other portion of these compounds is synthesized starting with commercially available starting materials 2,4-di-tert-butylphenol or 3,5-ditertbutyl-2-hydroxybenzaldehyde. 2,4-di-tert-butylphenol can be benzylbrominated ortho to the phenol utilizing the same procedure as the bis-phenol. This benzylbromide is combined with (1R,2R)—$N^1$,$N^2$-dimethyl-cyclohexane-1,2-diamine (synthesized according to literature procedures) in THF with Hünig's base to quench the acid formed in the reaction to form one amine precursor. Another varient of the ligand can be accessed by synthesizeing an amine starting from the imine condensation of 3,5-ditertbutyl-2-hydroxybenzaldehyde with 2-methoxy ethylamine. The imine is reduced to the desired amine with NaBH$_4$. The bis-salan ligand precursors are synthesized by the combining the desired amine in slight excess (2.2 equiv) with the bis-benzylbromide in THF with Hünig's base to quench the acid formed in the reaction. The bis-salans, $L^6$ and $L^7$, are isolated via column chromatography as pale solids.

Example 5

Separation of Syn and Anti Atropisomers

The syn and anti atropisomers of each of the present ligand precursors, $L^1$, $L^2$, $L^3$, $L^4$, $L^5$, $L^6$, and $L^7$, are separated in the course of the synthesis via column chromatography. For $L^1$ and $L^2$, the atropisomers are separated after removal of the MOM groups. For $L^3$, the atropisomers are separated after the Negishi coupling. For $L^4$, $L^5$, $L^6$, and $L^7$, the atropisomers are separated after removal of the methyl protecting groups. No interconversion has been noted in further reactivity or in synthesis of any of the metal complexes.

Example 6

Preparation of Dinickel Methylpyridine Complexes

Figure 10:
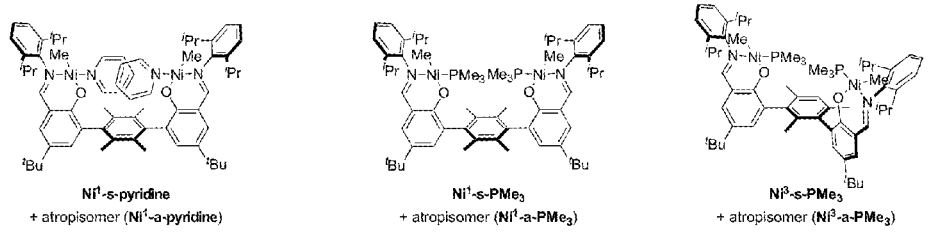
FIG. 10 shows the structures of multi-metallic polymerization catalysts according to embodiments herein described, and in particular multi-metallic polymerization catalysts with group 10 metals. Panel A shows the structure of the syn atropisomer of bimetallic polymerization catalyst $Ni^1$-s-pyridine. Panel B shows the structure of the syn atropisomer of bimetallic polymerization catalyst $Ni^1$-s-$PMe_3$. Panel C shows the structure of the syn atropisomer of bimetallic polymerization catalyst $Ni^3$-s-$PMe_3$.

Dinickel methylpyridine complexes have been prepared by alkane elimination between the Ni(Me)$_2$(tmeda) and bisphenoxyimines $L^1$ (FIG. 10). These reactions have been performed in diethyl ether. The nickel complexes are obtained as orange solids (Ni$^1$-a-pyridine and Ni$^1$-s-pyridine) $^1$H NMR spectra of the dinickel complexes show a single peak around −0.5 ppm, diagnostic of the N$_1$—CH$_3$ moiety. (See also Example 28).

Example 7

Preparation of Dinickel Methyl Triphenylphosphine

Dinickel methyl triphenylphosphine complexes have been prepared by deprotonation of the ligand precursors $L^1$ or $L^3$ with NaHMDS (for $L^1$-a) or KH (for $L^1$-s, $L^3$-s, $L^3$-a,) and salt metathesis with NiClMe(PMe$_3$)$_2$ to yield the bright orange dinickel complexes with methyl and phosphine donors (Ni$^1$-a-PMe$_3$, Ni$^1$-s-PMe$_3$, Ni$^3$-a-PMe$_3$ and Ni$^3$-s-PMe$_3$) (FIG. 10). $^1$H NMR spectra of the dinickel complexes show a single peak around −1.1 ppm, diagnostic of the N$_1$—CH$_3$ moiety. $^{31}$P NMR spectra of the dinickel complexes show a single peak around −9 ppm, corresponding to the Ni—PMe$_3$ moiety.

Example 8

Preparation of Titanium and Zirconium Bisphenoxyiminato Complexes

Di(titanium tris-isopropoxide) complexes have been prepared by isopropanol elimination between Ti(O$^i$Pr)$_4$ and bisphenoxyimines $L^1$ (FIG. 11A). The dititanium complexes are obtained as pale yellow solids (Ti$^1$-a-O$^i$Pr and Ti$^1$-s-O$^i$Pr). The $^1$H NMR spectra of these complexes display only one septet and one double for the isoproxide groups indicating fast interchange of these ligands.

Dititanium and dizirconium benzyl complexes have been prepared by toluene elimination between Ti(Bn)$_4$ or Zr(Bn)$_4$ and bisphenoxyimines $L^1$ (FIG. 11B and FIG. 11C). The dititanium complexes are obtained as deep red solids (Ti$^1$-a-Bn and Ti$^1$-s-Bn). The dizirconium complexes are obtained as orange solids (Zr$^1$-a-Bn and Zr$^1$-s-Bn). The $^1$H NMR spectra of both of these complexes display only one broad singlet indicative of the benzylic protons indicating fast interchange and rotation of these ligands.

Di(titanium dichloride) complexes have been synthesized by deprotonation of the ligand precursors $L^2$ with KH and salt metathesis with TiCl$_4$ to yield the red dititanium complexes with chloride ligands (Ti$^2$-a-Cl and Ti$^2$-s-Cl) (FIG. 11D). Due to the thioether moiety pendant to each of the bisphenoxyimines, it is assumed that 3 chlorides are present on each titanium making up a pseudo-octahedral geometry around the metal centers.

Example 9

Preparation of Titanium Bisphenoxycyclopentadienyl Complexes

Dititanium bisphenoxycyclopentadienyl complexes with chloride ligands have been synthesized by deprotonation of the cyclopentadienyl moieties of ligand precursor $L^4$-s with "BuLi followed by allyl group cleavage and phenoxide coordination upon treatment with $TiCl_4(THF)_2$ to form $Ti^4$-s-Cl (FIG. 11E) as a yellow solid. Further reaction of the titanium dichloride complex $Ti^4$-s-Cl with 2 equivalents of $Me_2Mg$ (tmeda) in diethyl ether at −35° C. provides the tetramethyl dititanium complex, $Ti^4$-s-Me, as a colorless oil (FIG. 11E).

Example 10

Preparation of Zirconium Bis-Salan Complexes

Dizirconium benzyl complexes have been prepared by toluene elimination between $Zr(Bn)_4$ and bis-salan $L^7$ (FIG. 11F). The zirconium complexes are obtained as pale yellow solids ($Zr^7$-a-Bn and $Zr^7$-s-Bn). Only a single isomer of $Zr^7$-a-Bn and $Zr^7$-s-Bn is evidenced by $^1H$ NMR spectroscopy indicating that the orientation of the benzyl ligands on one arm of the complex is affected by the presence of the opposite arm.

Example 11

Structural Characterization of Nickel and Titanium Complexes

Single-crystal X-ray diffraction (XRD) studies have been instrumental in confirming the assignment of atropisomers and determining the geometry around the metal centers in the solid state. Attempts to grow crystals suitable for XRD were successful for $Ni^1$-a-pyridine, $Ni^1$-s-pyridine, $Ti^1$-a-O$^i$Pr, $Ti^1$-s-O$^i$Pr, and $Ti^4$-s-Cl.

Figure 12:
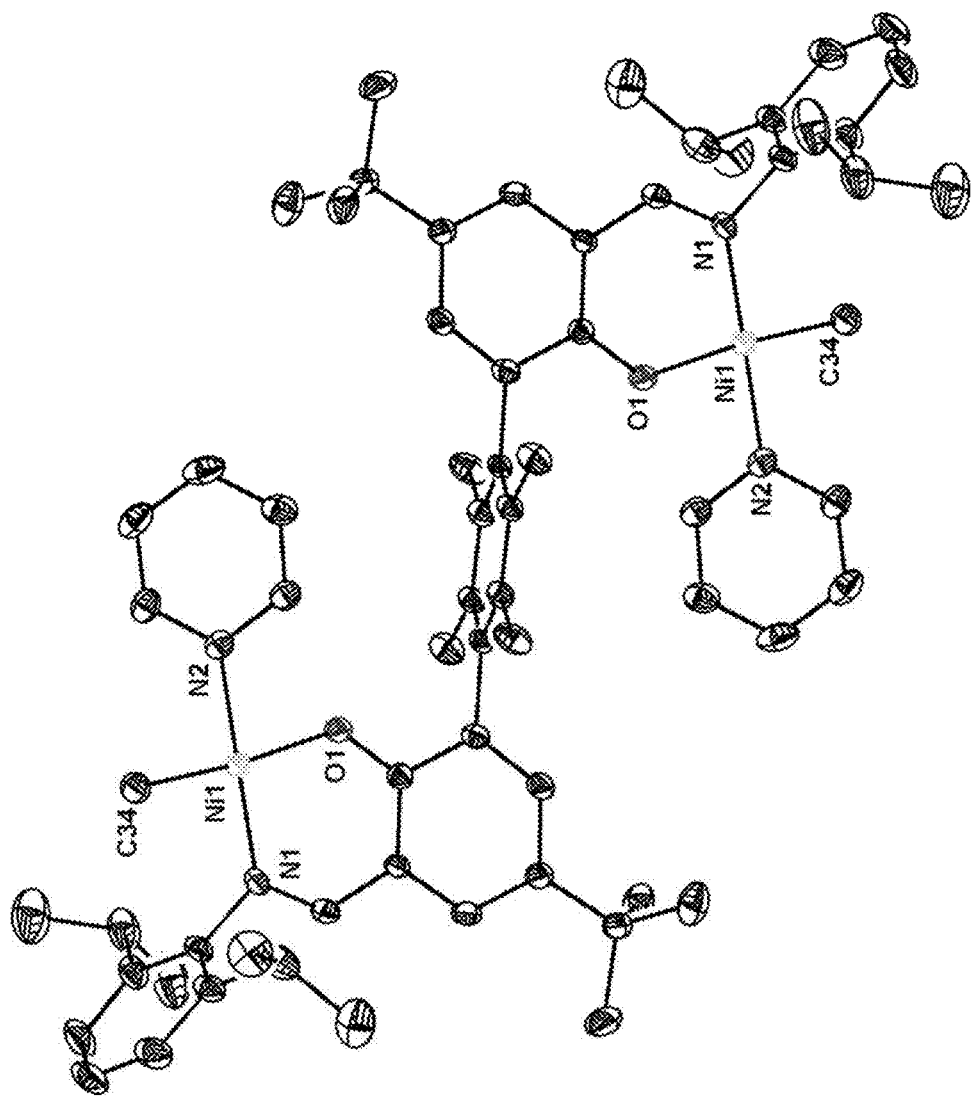
FIG. 12 shows solid-state structures of multi-metallic polymerization catalysts according to an embodiment herein described, and in particular the solid-state structure of $Ni^1$-a-pyridine.

Structural characterization of $Ni^1$-a-pyridine and $Ni^1$-s-pyridine confirmed a square planar geometry about all of the four-coordinate nickel centers with the methyl groups trans to the phenoxides and the pyridines trans to the imines (FIG. 12 and FIG. 13). The XRD study of $Ni^1$-s-pyridine indicated a Ni—Ni distance of 7.1 Å (average for the two molecules in the asymmetric unit), while the XRD study of $Ni^1$-a-pyridine indicated a Ni—Ni distance of 11.1 Å. Furthermore, there exists a slight distortion from square planar geometry about the nickel centers in $Ni^1$-s-pyridine probably due to steric interaction of the pyridine ligands indicating that substrates extending off of the metal centers for the syn atropisomer can cooperatively interact whereas the greater distance and the presence of the central arene prevents such interactions for the anti atropisomer.

Figure 14:
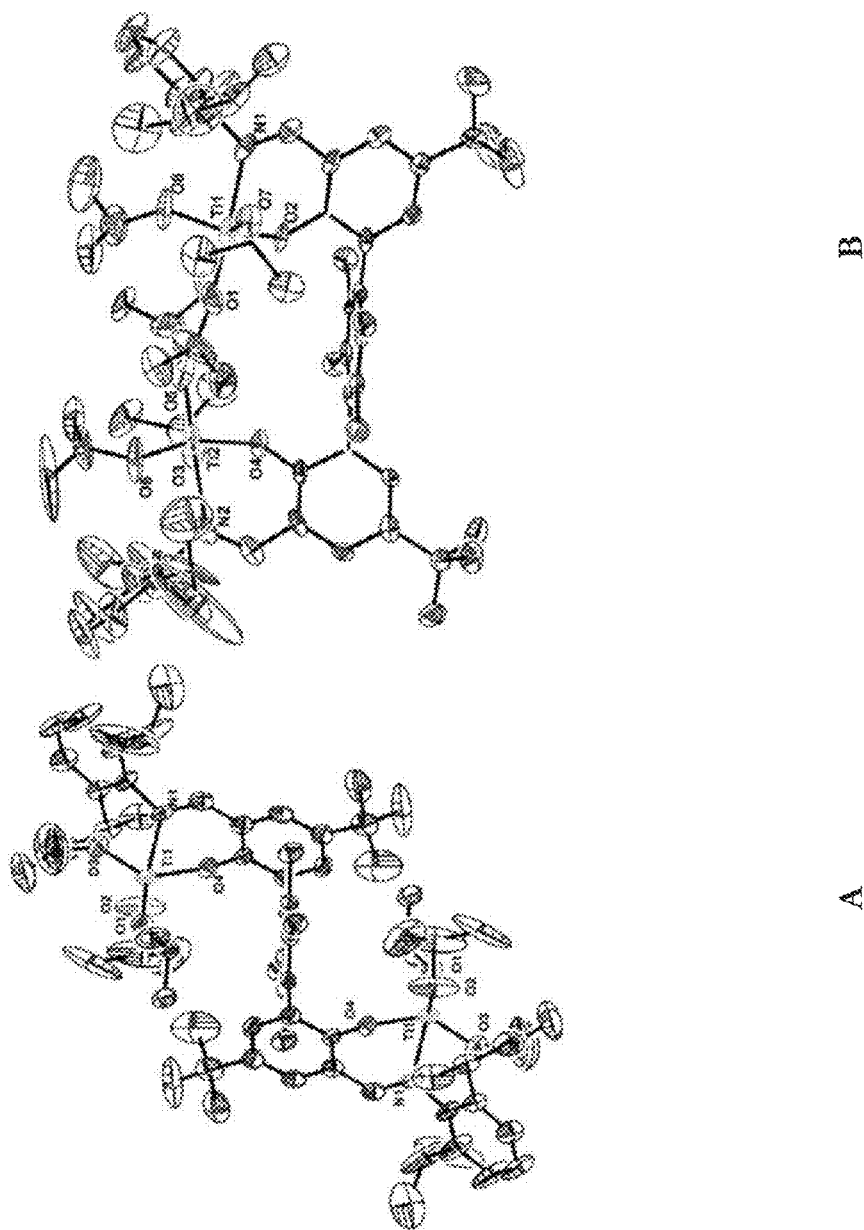
FIG. 14 shows solid-state structures of multi-metallic polymerization catalysts according to embodiments herein described. Panel A shows the solid-state structure of $Ti^1$-a-$O^iPr$. Panel B shows the solid-state structure of $Ti^1$-s-$O^iPr$.
Figure 15:
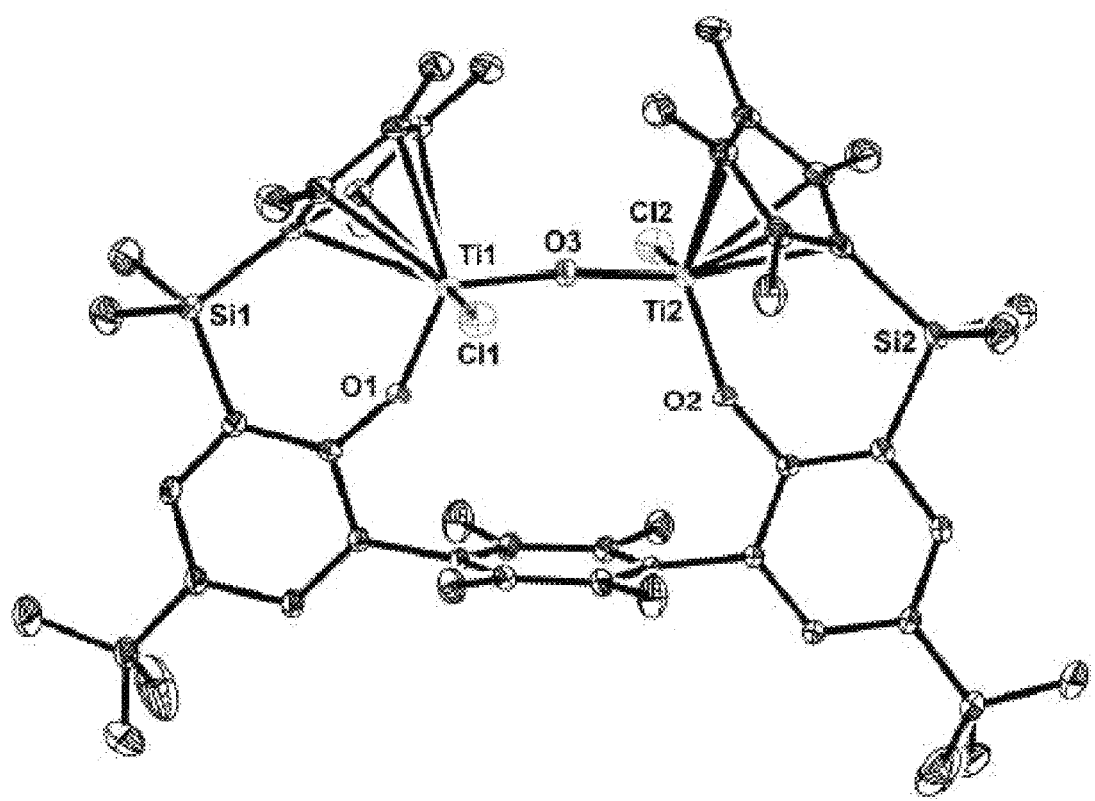
FIG. 15 shows a solid-state structure of a multi-metallic polymerization catalyst according to an embodiment herein described, and in particular the solid-state structure of the syn atropisomer of multi-metallic polymerization catalyst $Ti^4$-s-Cl with a bridging oxo ligand.

The titanium centers in $Ti^1$-a-O$^i$Pr and $Ti^1$-s-O$^i$Pr were found to be five-coordinate in the solid state, with distorted square pyramidal geometry (FIG. 14). As with the nickel complexes greater distortion was observed with $Ti^1$-s-O$^i$Pr where the isopropoxide ligands could interact sterically.

The titanium centers of $Ti^4$-s-Cl were found to be pseudo-tetrahedral with a bridging oxo ligand in the solid state (FIG. 15). The $^1H$ NMR data for this complex is consistent with both the desired tetrachloro complex and the dichloro(μ²-oxo) complex observed in the XRD study. (See also Example 29).

Example 12

Polymerizations with Nickel Bisphenoxyiminato Complexes

Ethylene homo- and copolymerization trials have been performed with $Ni^1$-a-pyridine and $Ni^1$-s-pyridine at 25° C. as single component catalysts in toluene or THF with and without alpha olefins and with and without polar additives (Table 1 to Table 3). Ethylene copolymerization trials have been performed with $Ni^1$-a-PMe$_3$ and $Ni^1$-s-PMe$_3$ at 25° C. with 2 equivalents of $Ni(COD)_2$ per nickel center in toluene with and without alpha olefins, polar additives, and polar monomers (Table 4 and Table 5). The nickel species generate white powdery polymers, which are separated from the quenched (with methanol/hydrochloric acid) reaction mixture by filtration. These materials are rinsed with methanol and volatiles are removed under vacuum at ambient temperature over at least 8 h. The materials are then massed and analyzed by various techniques including $^1H$, $^{13}C$, $^1H$, $^{13}C$ HSQCAD, and DOSY NMR spectroscopy, DSC and GPC. The activities of the nickels complexes with no polar additives or monomers present are comparable to monometallic analogues in the literature.[Ref 4, 31-33] With polar additives or monomers, which generally inhibit polymerization of the monometallic analogues, the syn atropisomers can still polymerize ethylene and have been shown to incorporate some polar monomers.

Ethylene homopolymerizations with $Ni^1$-a-pyridine and $Ni^1$-s-pyridine in toluene or THF suggests that the ether-containing solvent does not affect the polymerization activity of these complexes (Table 1). $^1H$ and $^{13}C$ NMR spectra shows only methyl branches in these polymers. Polymers made with $Ni^1$-s-pyridine displaying higher branch density than polymers made with $Ni^1$-a-pyridine, pointing to a higher relative rate of β-H elimination and isomerization versus olefin insertion for $Ni^1$-s-pyridine than for $Ni^1$-a-pyridine The higher degree of branching for $Ni^1$-s-pyridine relative to $Ni^1$-a-pyridine is also observed in copolymerizations of ethylene and alpha-olefins (Table 2). While the syn atropisomer produces more methyl branches the comonomer incorporation rates for the two atropisomers are similar. In these copolymerizations only methyl branches and branches the length of the comonomer chain are incorporated into the polymers indicating that no chain isomerization takes place after the insertion of a comonomer. GPC analysis has been performed on many of these polymers and in all cases the molecular weights of the polymers produced by $Ni^1$-a-pyridine are higher than those produced by $Ni^1$-s-pyridine suggesting that the polymerization activity of $Ni^1$-s-pyridine is limited by sterics.

TABLE 1

Ethylene Homopolymerizations with nickel precatalysts.[a]

| Entry | Complex | Solvent | Yield | TOF[b] | Branching[c] |
|---|---|---|---|---|---|
| 1 | Ni[1]-a-pyridine | toluene | 0.118 | 280 | |
| 2 | Ni[1]-a-pyridine | THF | 0.101 | 150 | 18.8 |
| 3 | Ni[1]-a-pyridine | THF | 0.224 | 333 | 17.3 |
| 4 | Ni[1]-s-pyridine | toluene | 0.047 | 69 | |
| 5 | Ni[1]-s-pyridine | toluene | 0.036 | 53 | |
| 6 | Ni[1]-s-pyridine | THF | 0.041 | 60 | 70.3 |
| 7 | Ni[1]-s-pyridine | THF | 0.043 | 64 | 67.5 |

[a]All polymerizations were run in a glass reactor under 100 psig of ethylene at 25° C. with 0.0080 mmol of Ni, 5 mL total volume for 3 h.
[b]TOF = turnover frequency in (mol $C_2H_4$) × (mol Ni)$^{-1}$ × h$^{-1}$.
[c]Branching was determined from $^1$H NMR spectroscopy and is reported as the number of branches per 1000 carbons.

TABLE 2

Ethylene/α-olefin copolymerization trials with nickel precatalysts (See also Table 8).

| Entry | Complex | Comonomer | Yield (g) | Branching[b] | Branch type[c] | Branch ratio[c] | % inc[d] | TOF e[e] | TOF co[e] | $M_w$[f] | $M_n$[f] | PDI[f] |
|---|---|---|---|---|---|---|---|---|---|---|---|---|
| 1 | Ni[1]-a-pyr | | 0.101 | 17.3 | m | | | 150 | | | | |
| 2 | Ni[1]-a-pyr | | 0.224 | 18.8 | m | | | 333 | | 47591 | 6309 | 7.54 |
| 3 | Ni[1]-s-pyr | | 0.041 | 70.3 | m | | | 60 | | | | |
| 4 | Ni[1]-s-pyr | | 0.043 | 67.5 | m | | | 64 | | 8114 | 2697 | 3.01 |
| 5 | Ni[1]-a-pyr | 1-pentene | 0.087 | 33.4 | m + p | 1:1.2 | 3.9 | 124 | 2.0 | 15238 | 4271 | 3.57 |
| 6 | Ni[1]-a-pyr | 1-pentene | 0.086 | 31.3 | m + p | 1:1.3 | 3.7 | 123 | 1.9 | | | |
| 7 | Ni[1]-s-pyr | 1-pentene | 0.044 | 70.2 | m + p | 1:0.3 | 3.4 | 64 | 0.9 | 7707 | 2583 | 2.98 |
| 8 | Ni[1]-s-pyr | 1-pentene | 0.028 | 76.1 | m + p | 1:0.3 | 3.7 | 39 | 0.6 | | | |
| 9 | Ni[1]-a-pyr | 1-hexene | 0.112 | 31.1 | m + b | 1:2.1 | 4.6 | 159 | 2.6 | 14088 | 3712 | 3.80 |
| 10 | Ni[1]-a-pyr | 1-hexene | 0.080 | 31.6 | m + b | 1:2.3 | 4.8 | 112 | 1.9 | | | |
| 11 | Ni[1]-s-pyr | 1-hexene | 0.018 | 63.7 | m + b | 1:0.4 | 3.9 | 25 | 0.3 | | | |
| 12 | Ni[1]-s-pyr | 1-hexene | 0.016 | 62.9 | m + b | 1:0.3 | 3.1 | 22 | 0.2 | 2759 | 893 | 3.09 |
| 13 | Ni[1]-a-pyr | 1-heptene | 0.053 | 36.0 | m + pn | 1:2.7 | 6.0 | 74 | 1.4 | 9097 | 3037 | 3.00 |
| 14 | Ni[1]-a-pyr | 1-heptene | 0.045 | 40.7 | m + pn | 1:3.2 | 7.3 | 61 | 1.4 | | | |
| 15 | Ni[1]-s-pyr | 1-heptene | 0.022 | 68.0 | m + pn | 1:0.5 | 5.1 | 31 | 0.5 | 3619 | 1196 | 3.03 |
| 16 | Ni[1]-s-pyr | 1-heptene | 0.006 | 61.3 | | | | | | | | |
| 17 | Ni[1]-a-pyr | 1-octene | 0.017 | 49.4 | m + h | 1:4.1 | 10.4 | 22 | 0.7 | 4472 | 1068 | 4.19 |
| 18 | Ni[1]-a-pyr | 1-octene | 0.017 | 49.5 | m + h | 1:6.2 | 11.5 | 22 | 0.7 | | | |
| 19 | Ni[1]-s-pyr | 1-octene | 0.012 | 61.0 | m + h | 1:0.6 | 5.3 | 17 | 0.2 | 2030 | 559 | 3.63 |
| 20 | Ni[1]-s-pyr | 1-octene | 0.009 | 51.1 | | | | | | | | |

[a]All polymerizations were run for 3 h in a glass reactor with 0.0080 mmol of nickel in THF under 100 psig of ethylene with 3200 equivalents of comonomer per nickel at 25° C. The total reaction volume was 5 mL.
[b]Branching was determined from $^1$H NMR spectroscopy and is reported as the number of branches per 1000 carbons.
[c]Determined from $^{13}$C NMR spectroscopy: m = methyl, p = propyl, b = butyl, pn = pentyl, h = hexyl.
[d]% incorporation was calculated from the overall branching and the branch ratio.
[e]TOF = turnover frequency in (mol monomer) × (mol Ni)$^{-1}$ × h$^{-1}$. "e" = ethylene, "co" = comonomer. Calculated from the yield and the % incoporation of comonomer.
[f]Calculated from GPC results.

Figure 17:
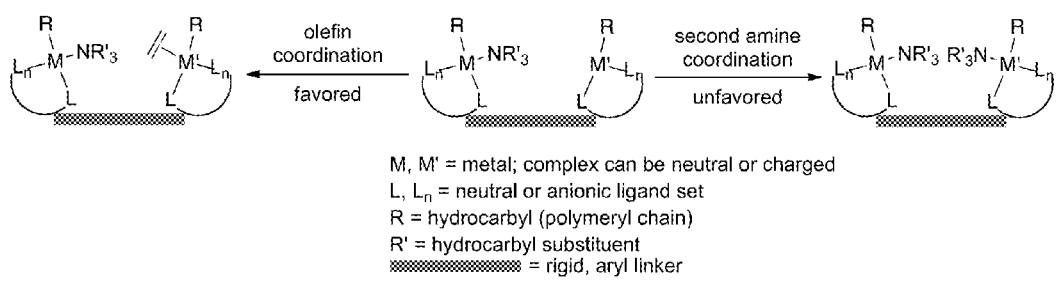
FIG. 17 shows a schematic illustration of possible effects occurring in the multi-metallic polymerization catalysts according to embodiments herein described when in the presence of amines.

In the presence of polar additives, Ni[1]-s-pyridine can be more active than Ni[1]-a-pyridine (Table 3). By examining the ratios of deactivation (R, Table 4), inhibition trends can be observed. Polymerizations with primary, secondary, and tertiary amines show decreased inhibition of the syn atropisomer especially with amines large enough to, when bound to one nickel center affect substituents on the other nickel center by, for example, disfavoring the binding of a second, bulky amine relative to coordination of the smaller ethylene molecule (FIG. 17). The authors expected that this effect could be capitalized upon to achieve the incorporation of polar monomers, but a more active polymerization catalyst was required.

TABLE 3

Ethylene Homopolymerizations with nickel precatalysts in the presence of polar additives.[a]

| | Additive | Equiv | Yield (g) | | TOF[b] | | R[c] |
|---|---|---|---|---|---|---|---|
| | | | Ni[1]-s-pyridine | Ni[1]-a-pyridine | Ni[1]-s-pyridine | Ni[1]-a-pyridine | |
| 1 | none | n/a | 0.574 | 3.415 | 341 | 2029 | — |
| 2 | none | n/a | 0.894 | 1.893[d] | 531 | 2250[d] | — |

TABLE 3-continued

Ethylene Homopolymerizations with nickel precatalysts in the presence of polar additives.[a]

| | | Yield (g) | | TOF[b] | | |
|---|---|---|---|---|---|---|
| Additive | Equiv | Ni[1]-s-pyridine | Ni[1]-a-pyridine | Ni[1]-s-pyridine | Ni[1]-a-pyridine | R[c] |
| 3 NMe$_2$Et | 500 | 0.150 | 1.440 | 89 | 856 | 0.5 |
| 4 NMe$_2$Et | 500 | 0.148 | 1.032 | 88 | 613 | 0.7 |
| 5 NMe$_2$Et | 5000 | 0.068 | 0.103 | 41 | 61 | 3.3 |
| 6 NMeEt$_2$ | 500 | 0.128 | 0.181 | 76 | 108 | 3.5 |
| 7 NEt$_3$ | 500 | 0.039 | 0.016 | 23 | 9 | 12.2 |
| 8 NMe$_2$R[1e,f] | 225 | 0.058 | 0.071 | 103 | 126 | 4.0 |
| 9 NMe$_2$R[1e] | 500 | 0.062 | 0.111 | 36 | 66 | 2.7 |
| 10 NMe$_2$$^n$Pr | 500 | 0.036 | 0.025 | 21 | 15 | 7.2 |
| 11 NMe$^n$Pr$_2$ | 500 | 0.070 | 0.019 | 41 | 11 | 18.4 |
| 12 N$^n$Pr$_3$ | 500 | 0.055 | 0.001 | 33 | 1 | 269 |
| 13 NMe$_2$$^n$Bu | 500 | 0.047 | 0.019 | 25 | 10 | 12.1 |
| 14 NMe$_2$$^n$Bu | 500 | 0.066 | 0.028 | 39 | 17 | 11.6 |
| 15 NMe$^n$Bu$_2$ | 500 | 0.012 | 0.009 | 7 | 5 | 6.3 |
| 16 N$^n$Bu$_3$ | 500 | 0.003 | —[i] | 2 | —[i] | — |
| 17 NMe$_2$Ph | 500 | 0.619 | 2.867 | 367 | 1703 | 1.1 |
| 18 NMe$_2$Bz | 500 | 0.252 | 1.330 | 150 | 790 | 0.9 |
| 19 HN$^n$Pr | 20 | —[i] | —[i] | —[i] | —[i] | — |
| 20 HNMe$^n$Bu | 20 | —[i] | —[i] | —[i] | —[i] | — |
| 21 HN$^n$Bu$_2$ | 20 | —[i] | —[i] | —[i] | —[i] | — |
| 22 HN$^i$Pr | 20 | 0.299 | 0.149 | 178 | 88 | 9.9 |
| 23 H$_2$N$^n$Bu | 5 | —[i] | —[i] | —[i] | —[i] | — |
| 24 H$_2$NR[2g] | 50 | 0.011 | —[i] | 7 | —[i] | — |
| 25 H$_2$NR[2g] | 20 | 0.022 | —[i] | 13 | —[i] | — |
| 26 H$_2$NR[2g] | 5 | 0.080 | 0.003 | 48 | 2 | 136 |
| 27 H$_2$NR[3h] | 5 | 0.086 | 0.006 | 51 | 4 | 69.4 |
| 28 Pyridine | 10 | —[i] | —[i] | —[i] | —[i] | — |

[a]All polymerizations were run for 3 hours at 25° C. under 100 psig of ethylene in 25 ml of toluene with 10 μmol of dinickel complex. The number of equivalents of base listed is the number of equivalents per nickel.
[b]TOF = turnover frequency = (mol C$_2$H$_4$) · (mol Ni)$^{-1}$ · h$^{-1}$.
[c]R = ([TOF for Ni[1]-a-pyr with no additive]/[TOF for Ni[1]-a-pyr with additive])/([TOF for Ni[1]-s-pyr with no additive]/[TOF for Ni[1]-s-pyr with additive]).
[e]R[1] = allyl.
[f]Polymerization was run for 1 hour.
[g]R[2] = 1,1-dimethylpropyl.
[h]R[3] = 1,1,3,3-tetramethylbutyl.
[i]Insufficient product to accurately mass (<1 mg). (See also Table 9).

Copolymerizations of ethylene and 1-hexene with Ni[1]-a-PMe$_3$ and Ni[1]-s-PMe$_3$ at 25° C. in toluene using 2 equivalents of Ni(COD)$_2$ per nickel center as phosphine scavengers have been completed and demonstrate that Ni[1]-a-PMe$_3$ and Ni[1]-s-PMe$_3$ with 2 equivalents of Ni(COD)$_2$ per nickel center are significantly more active for polymerization than single component catalysts Ni[1]-a-pyridine and Ni[1]-s-pyridine under the same conditions (Table 4). Ethylene/1-hexene copolymerizations by Ni[1]-a-PMe$_3$ and Ni[1]-s-PMe$_3$ with only 500 equivalents of 1-hexene per nickel exhibit about 1% comonomer incorporation, an amount easily evidenced by $^1$H and $^{13}$C NMR spectroscopy. When 500 equivalents of dipropylmethylamine is added to these polymerizations, Ni[1]-s-PMe$_3$ still produces polymer, encouraging attempts for copolymerizations with polar monomers.

TABLE 4

Ethylene/1-hexene polymerizations with nickel precatalysts.[a]

| Entry | Complex | 1-hexene equivalents[b] | Time (minutes) | Yield (g) | TOF[c] | % inc[d] |
|---|---|---|---|---|---|---|
| 1 | Ni[1]-s-PMe$_3$ | 3200 | 30 | 0.734 | 184 | 5.2 |
| 2 | Ni[1]-s-PMe$_3$ | 500 | 30 | 0.849 | 212 | 1.2 |
| 3 | Ni[1]-s-PMe$_3$ | 500 | 30 | 1.165 | 291 | 1.2 |
| 4 | Ni[1]-s-PMe$_3$ | 500 | 15 | 0.399 | 193 | 1.8 |
| 5 | Ni[1]-a-PMe$_3$ | 500 | 30 | 1.180 | 295 | 1.0 |
| 6 | Ni[1]-a-PMe$_3$ | 500 | 30 | 1.430 | 357 | —[f] |
| 7 | Ni[1]-a-PMe$_3$ | 500 | 15 | 0.492 | 246 | —[f] |
| 8[e] | Ni[1]-s-PMe$_3$ | 500 | 30 | 0.014 | 4 | —[f] |
| 9[e] | Ni[1]-a-PMe$_3$ | 500 | 30 | —[g] | —[g] | —[f] |

[a]All polymerizations were run in a glass reactor with 0.0080 mmol of nickel in toluene under 100 psig of ethylene with 2 equivalents of Ni(COD)$_2$ per Ni at 25° C. The total reaction volume was 5 mL.
[b]The number of equivalents of base listed is the number of equivalents per nickel.
[c]TOF = turnover frequency in (g polymer) × (mol Ni)$^{-1}$ × h$^{-1}$.
[d]% incorporation was calculated from the $^1$H and $^{13}$C NMR spectra.
[e]500 equivalents of dipropylmethylamine per nickel were added to these polymerizations.
[f]No NMR spectra or insufficient signal to noise to determine % inc.
[g]Insufficient product to accurately mass (<1 mg).

Figure 18:
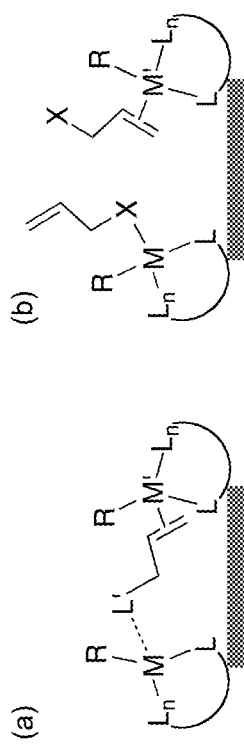
FIG. 18 shows a schematic illustration of possible modes of metal-metal cooperativity for the incorporation of polar monomers occurring in the multi-metallic polymerization catalysts according to embodiments herein described.
Figure 19:
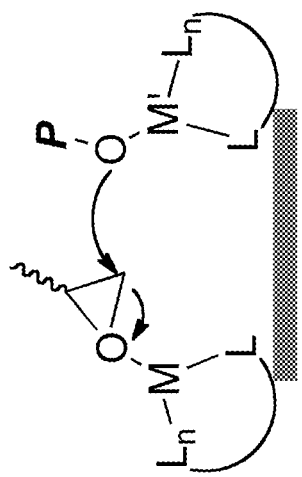
FIG. 19 shows a schematic illustration of possible bimetallic activation in ring-opening polymerization of epoxides occurring in the multi-metallic polymerization catalysts according to embodiments herein described [Ref 1].

Copolymerization attempts of ethylene or ethylene and 1-hexene with polar comonomers indicate that only Ni[1]-s-PMe$_3$ can produce polymers under these conditions implying that the proximity of the metal centers is responsible for these results (Table 5). DOSY and $^1$H-$^{13}$C HSQCAD NMR spectra confirm that the amine-containing olefins are incorporated into the polymer chains. Two potential modes of the bimetallic effect are illustrated in FIG. 18. One is directly related to the steric effect hypothesized for the inhibition trends wherein a bulky polar moiety on one monomer binds to one of the nickel centers disfavoring the binding of an amine to the other nickel center over coordination of the more sterically open olefin moiety; sterically favored olefin coordination allows for insertion and propagation to generate a polyolefin.

A second potential mechanism involves binding of the polar moiety of a monomer to one metal center leading to increased binding of the olefinic moiety of that same monomer to the second metal center; this facilitates insertion and propagation to form a polyolefin incorporating the polar monomer.

TABLE 5

Ethylene/polar olefin copolymerization trials with nickel precatalysts.[a]

| Entry | Complex | Comonomer(s) | Yield (g) | % inc (polar monomer)[b] | TOF[c] |
|---|---|---|---|---|---|
| 1 | Ni[1]-s-PMe$_3$ | N(allyl)[n]Pr$_2$ | 0.022 | none | 5.5 |
| 2 | Ni[1]-a-PMe$_3$ | N(pentenyl)[n]Pr$_2$ | —[d] | — | —[d] |
| 3 | Ni[1]-s-PMe$_3$ | N(pentenyl)[n]Pr$_2$ | 0.049 | 0.5 | 12.3 |
| 4 | Ni[1]-s-PMe$_3$ | N(pentenyl)[n]Pr$_2$, 1-hexene | 0.061 | 0.5 | 15.3 |
| 5 | Ni[1]-s-PMe$_3$ | N(pentenyl)Et$_2$ | 0.027 | 0.8 | 6.8 |
| 6 | Ni[1]-s-PMe$_3$ | N(pentenyl)Et$_2$, 1-hexene | 0.032 | 0.7 | 8.0 |

[a]All polymerizations were run for 30 minutes in a glass reactor with 0.0080 mmol of nickel in toluene under 100 psig of ethylene with 2 equivalents of Ni(COD)$_2$ per Ni with 500 equivalents of (each) comonomer at 25° C. The total reaction volume was 5 mL.
[b]% incorporation of the polar monomer was calculated from the $^1$H NMR spectrum.
[c]TOF = turnover frequency in (g polymer) × (mol Ni)$^{-1}$ × h$^{-1}$.
[d]Insufficient product to accurately mass (<1 mg).

Figure 16:
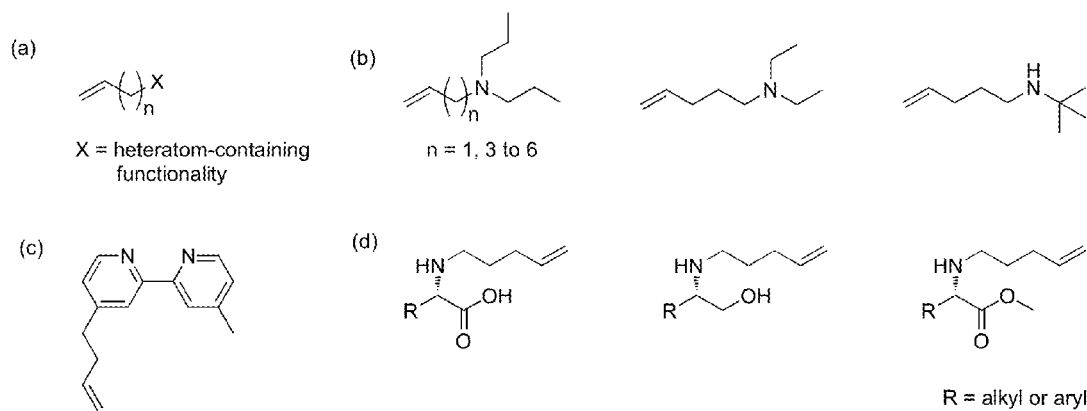
FIG. 16 shows monomers for use in polymerization reactions with multi-metallic polymerization catalysts according to embodiments herein described. Panel A shows a general structure of polar olefin monomers according to embodiments herein described. Panel B shows exemplary embodiments of polar olefin monomers. Panel C shows an exemplary embodiment of a metal-binding olefin monomer. Panel D shows exemplary embodiments of chiral olefin monomers.

The scope of polar monomers that can be utilized in these copolymerizations has yet to be expanded on and FIG. 16 exemplifies a few targets expected to incorporate. The authors anticipate that other olefins of the form in FIG. 16A, as well as tertiary and secondary amine-containing olefins (FIG. 16B), olefins which could subsequently bind metals (FIG. 16C) to form metal containing polymers, and olefins with chiral centers (FIG. 16D) to form chiral polymers. (See Also Example 30).

Example 13

Figure 5:
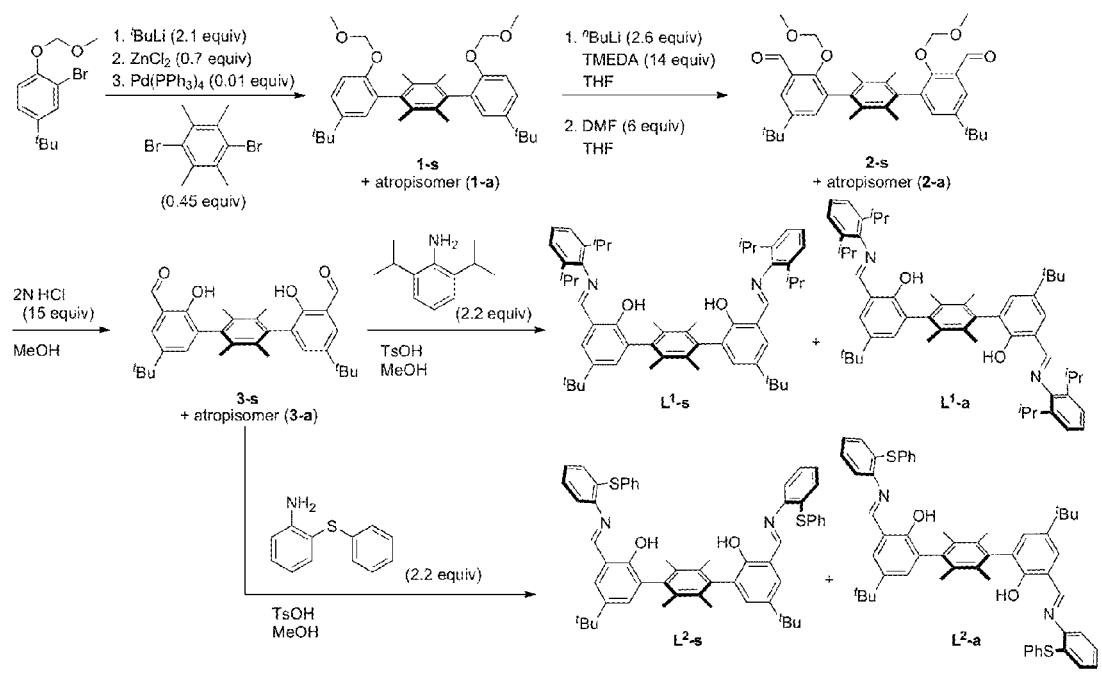
FIG. 5 shows a schematic illustration of an exemplary reaction scheme for the preparation of atropisomers of a p-terphenyl bisphenoxyimine ligands according to an embodiment herein described and a variant with pendant donors according to an embodiment herein described, and in particular the synthesis of p-terphenyl bisphenoxyimine ligands $L^1$-s and $L^1$-a and variants with pendant donors $L^2$-s and $L^2$-a.

Preparation of Ligand Subunits (FIG. 5)

2-bromo-4-tert-butylphenol [Ref 34] and 1,4-dibromo-2,3,5,6-tetramethylbenzene [Ref 35] were synthesized according to literature procedures.

2-bromo-4-tert-butylmethoxymethylphenol was synthesized from 2-bromo-4-tert-butylphenol according an analogous literature synthesis.[Ref 36] $^1$H NMR (400 MHz, CDCl$_3$): δ 7.30 (d, J=2.4 Hz, 1H, ArH), 7.00 (dd, J=8.7, 2.4 Hz, 1H, ArH), 6.83 (d, J=8.6 Hz, 1H, ArH), 4.97 (s, 2H, OCH$_2$OCH$_3$), 3.27 (s, 3H, OCH$_2$OCH$_3$), 1.04 (s, 9H, C(CH$_3$)$_3$) ppm. $^{13}$C NMR (101 MHz, CDCl$_3$): δ 151.49 (Ar), 146.47 (Ar), 130.45 (Ar), 125.41 (Ar), 115.95 (Ar), 112.63 (Ar), 95.27 (OCH$_2$OCH$_3$), 56.37 (OCH$_2$OCH$_3$), 34.30 (ArC(CH$_3$)$_3$), 31.42 (ArC(CH$_3$)$_3$) ppm. HRMS (FAB+) Calcd. for C$_{12}$H$_{17}$BrO$_2$: 272.0412. Found: 272.0411.

1-a and 1-s. Synthesis of the biphenyl compounds 1 was accomplished via the Negishi coupling of 1,4-dibromo-2,3,5,6-tetramethybenzene with two equivalents of 2-bromo-4-tert-butylmethoxymethylphenol using literature conditions. [Ref 37] In the glove box, 2-bromo-4-tert-butylmethoxymethylphenol (10.46 g, 38.3 mmol) and 150 mL of THF were combined in a large Schlenk tube and frozen in the cold well. tert-Butyllithium (47.32 mL, 80.44 mmol, 2.1 equiv) was added to the thawing solution and stirred for 1 h while warming to room temperature. The resultant yellow orange solution was refrozen in the cold well. Concurrently, a suspension of ZnCl$_2$ (3.66 g, 26.8 mmol, 0.7 equiv) in THF (40 mL) was frozen in the cold well. The thawing ZnCl$_2$ suspension was added to the thawing reaction mixture and stirred for 1 h resulting in a colorless cloudy solution. 1,4-dibromo-2,3,5,6-tetramethybenzene (5.03 g, 17.24 mmol, 0.45 equiv), Pd(PPh$_3$)$_4$ (0.44 g, 0.38 mmol, 0.01 equiv) and THF (40 mL) were added to the reaction mixture at room temperature. The sealed Schlenk tube was brought out of the glove box and heated to 70° C. for 4 days. Water was added to quench the reaction. The solution was filtered over silica gel and the silica gel was washed with dichloromethane. The filtrate was extracted between DCM and water. The organics were dried with MgSO$_4$, filtered, and volatiles were removed under vacuum. The di-coupled products were coprecipitated from MeOH in a ratio of 1:0.73 anti:syn (4.75 g of white powder, 53% yield). $^1$H NMR (300 MHz, CDCl$_3$): δ=7.33-7.29 (2dd, J=8.6, 2.5, 2H per atropisomer, ArH), 7.17-7.10 (4d, J=8.6, 2.5, 4H per atropisomer, ArH), 5.07 (s, 4H, OCH$_2$OCH$_3$, anti), 4.97 (s, 4H, OCH$_2$OCH$_3$, syn), 3.37 (s, 6H, OCH$_2$OCH$_3$, anti), 3.24 (s, 6H, OCH$_2$OCH$_3$, syn), 1.97 (s, 12H, Ar—CH$_3$, syn), 1.95 (s, 12H, Ar—CH$_3$, anti), 1.32 (s, 18H per atropisomer, ArC(CH$_3$)$_3$) ppm.

2-a and 2-s. 1 (4.75 g, 9.16 mmol, 1 equiv), N,N,N',N'-tetramethylethylenediamine (19.1 mL, 128.2 mmol, 14 equiv) and THF (80 mL) were added to a Schlenk tube in the glove box and frozen in the cold well. n-Butyllithium (9.6 mL, 24.0 mmol, 2.6 equiv) was added to the thawing solution and stirred for 4 h. The resultant orange red solution was refrozen in the cold well. A solution of DMF (4.3 mL, 54.9 mmol, 6 equiv) in THF (30 mL) was also frozen in the cold well. The thawing DMF solution was added to the thawing reaction mixture resulting in a pale amber solution, which was stirred for 10 h before the Schlenk tube was brought out of the box and about 5 mL of water were added to quench the reaction. The desired product was extracted into DCM and the organic fraction was washed with water, dried with MgSO$_4$, filtered, and the volatiles were removed under vacuum to yield the doubly orthoformylated products, 2, with greater than 90% purity. These compounds were carried forward without further purification and 100% conversion was assumed for stoichiometry. $^1$H NMR (300 MHz, CDCl$_3$): δ 10.49 (2s, 2H per atropisomer, OCH), 7.90 (2d, J=2.7, 2H per atropisomer, ArH), 7.43 (d, J=2.7, 2H, ArH, syn), 7.31 (d, J=2.6, 2H, ArH, anti), 4.67 (s, 4H, OCH$_2$OCH$_3$, anti), 4.60 (s, 4H, OCH$_2$OCH$_3$, syn), 3.29 (s, 6H, OCH$_2$OCH$_3$, syn), 3.24 (s, 6H, OCH$_2$OCH$_3$, anti), 2.03 (s, 12H, Ar—CH$_3$, syn), 2.00 (s, 12H, Ar—CH$_3$, anti), 1.35 (2s, 18H per atropisomer, ArC(CH$_3$)$_3$) ppm.

3-a and 3-s. 2 (5.26 g, 9.2 mmol, 1 equiv), 2N HCl (69 mL, 137.4 mmol, 15 equiv), and methanol (275 mL) were added to a round bottom flask equipped with a reflux condenser and the reaction was refluxed for 2 h. Then the reaction was cooled to room temperature and filtered to collect precipitate. The precipitate was dissolved in DCM and washed with water. Additional product was collected from the filtrate by extraction into DCM. The organic fractions were dried with MgSO$_4$, filtered, and the volatiles were removed under vacuum to yield the deprotected products, 3. The atropisomers were separated via column chromatography (3:1 DCM/hexanes). 1.3 g of 3-a and 0.7 g of 3-s were isolated as white solids in 95 puritiy (45% overall yield). 3-a $^1$H NMR (400 MHz, CDCl$_3$): δ 11.13 (s, 2H, OH), 9.99 (s, 2H, OCH), 7.56 (d, J=2.5, 2H, ArH), 7.53 (d, J=2.5, 2H, ArH), 1.99 (s, 12H, Ar—CH$_3$), 1.38 (s, 18H, C(CH$_3$)$_3$) ppm. 3-s $^1$H NMR (400 MHz, CDCl$_3$): δ 10.92 (s, 2H, OH), 9.99 (s, 2H, OCH), 7.55 (d, J=2.5, 2H, ArH), 7.45 (d, J=2.5, 2H, ArH), 1.99 (s, 12H, Ar—CH$_3$), 1.36 (s, 18H, C(CH$_3$)$_3$) ppm.

L$^1$-a. The anti-bis-salicylaldimine compound was synthesized by mixing 3-a (0.36 g, 0.74 mmol, 1 equiv), p-toluenesulfonic acid (0.014 g, 0.074 mmol, 0.1 equiv), 2,6-diisopropylamine (0.31 mL, 1.63 mmol, 2.2 equiv), and methanol (40 mL) in a round bottom flask equipped with a reflux condenser. A color change to orange was observed with the addition of aniline. The mixture was stirred at reflux for 4 h and then cooled to room temperature. A pale solid was collected from the deep red solution via filtration. The precipitate was further purified by column chromatography (2:1 hexanes/DCM) and 0.44 g (73% yield) of pale yellow solid was obtained. $^1$H NMR (400 MHz, C$_6$D$_6$): δ 13.45 (s, 2H, OH), 8.05 (s, 2H, NCH), 7.42 (d, 2H, ArH), 7.28 (d, 2H, ArH), 7.11 (bs, 6H, N—ArH), 3.06 (septet, J=6.8, 4H, CH(CH$_3$)$_2$), 2.24 (s, 12H, ArCH$_3$), 1.29 (s, 18H, C(CH$_3$)$_3$), 1.06 (d, J=6.8, 24H, CH(CH$_3$)$_2$) ppm. $^{13}$C NMR (101 MHz, C$_6$D$_6$): δ 168.05 (ArCHN), 157.53 (Ar), 147.32 (Ar), 141.85 (Ar), 138.96 (Ar), 137.61 (Ar), 133.75 (Ar), 132.81 (Ar), 131.98 (Ar), 125.75 (Ar), 123.54 (Ar), 118.49 (Ar), 34.26 (ArC(CH$_3$)$_3$), 31.60 (ArC(CH$_3$)$_3$), 28.63 (ArCH(CH$_3$)$_2$), 23.42 (ArCH(CH$_3$)$_2$), 18.44 (ArCH$_3$) ppm. HRMS (FAB+) Calcd. for C$_{56}$H$_{73}$O$_2$N$_2$: 805.5672. Found: 805.5693.

L$^1$-s. The imine condensation to form the syn-bis-salicylaldimine compound from 3-s was accomplished via the same procedure as the anti. The desired product was isolated as a pale yellow solid in 56% yield (1.32 g). $^1$H NMR (400 MHz, C$_6$D$_6$): δ 13.45 (s, 2H, OH), 8.06 (s, 2H, NCH), 7.45 (d, 2H, ArH), 7.29 (d, 2H, ArH), 7.13 (bs, 6H, N—ArH), 3.12 (septet, J=6.8, 4H, CH(CH$_3$)$_2$), 2.22 (s, 12H, ArCH$_3$), 1.27 (s, 18H, C(CH$_3$)$_3$), 1.11 (d, J=6.8, 24H, CH(CH$_3$)$_2$) ppm. $^{13}$C NMR (101 MHz, C$_6$D$_6$): δ 168.04 (ArCHN), 157.58 (Ar), 147.39 (Ar), 141.68 (Ar), 138.95 (Ar), 137.76 (Ar), 133.43 (Ar), 132.92 (Ar), 131.98 (Ar), 127.65 (Ar), 125.77 (Ar), 123.54 (Ar), 118.62 (Ar), 34.19 (ArC(CH$_3$)$_3$), 31.57 (ArC(CH$_3$)$_3$), 28.67 (ArCH(CH$_3$)$_2$), 23.46 (ArCH(CH$_3$)$_2$), 18.47 (ArCH$_3$) ppm. HRMS (FAB+) Calcd. for C$_{56}$H$_{73}$O$_2$N$_2$: 805.5672. Found: 805.5688.

Example 14

Synthesis of Bisphenoxyiminato Compounds with Pendant Donors (Para—FIG. 5)

L$^2$-a. 3-a (0.258 g, 0.530 mmol, 1 equiv), 2-aminophenyl phenyl sulfide (0.235 g, 1.166 mmol, 2.2 equiv), tosic acid (0.010 g, 0.053 mmol, 0.1 equiv) and MeOH (25 mL) were combined in a round bottom flask equipped with a stirbar and a reflux condenser. The reaction mixture was heated to reflux with stifling for 30 h and then cooled to room temperature and put into freezer to precipitate for 12 h. The pale solid was collected over a frit and purified via column chromatography (2:1 hexanes/DCM) to yield 0.2 g of pale yellow solid (44% yield). $^1$H NMR (300 MHz, CDCl$_3$): δ 12.89 (s, 2H, OH), 8.62 (s, 2H, NCH), 7.26 (m, 22H, ArH), 2.04 (s, 12H, Ar—CH$_3$), 1.34 (s, 18H, C(CH$_3$)$_3$) ppm.

L$^2$-s. The imine condensation with 2-aminophenyl phenyl sulfide and 3-s was accomplished via the same procedure as the anti. The desired product was isolated as a pale yellow solid in 80% yield (0.24 g). $^1$H NMR (400 MHz, C$_6$D$_6$): δ 13.39 (s, 2H, OH), 8.15 (s, 2H, NCH), 7.41 (d, J=2.5, 2H, ArH), 7.31 (dd, J=7.8, 1.4, 3H, ArH), 7.16 (d, J=2.5, 3H, ArH), 7.12 (dd, J=7.8, 1.4, 2H, ArH), 6.92 (td, J=7.6, 1.3, 2H, ArH), 6.88 (m, 6H, ArH), 6.81 (td, J=7.6, 1.3, 2H, ArH), 6.73 (dd, J=7.9, 1.3, 2H, ArH), 2.24 (s, 12H, Ar—CH$_3$), 1.29 (s, 18H, C(CH$_3$)$_3$) ppm. $^{13}$C NMR (101 MHz, C$_6$D$_6$): δ 163.78 (Ar), 157.54 (Ar), 147.66 (Ar), 141.30 (Ar), 137.97 (Ar), 134.35 (Ar), 134.06 (Ar), 133.62 (Ar), 133.41 (Ar), 132.91 (Ar), 131.90 (Ar), 130.05 (Ar), 129.50 (Ar), 128.17 (Ar), 127.94 (Ar), 127.20 (Ar), 127.13 (Ar), 119.21 (Ar), 118.59 (Ar), 34.16 (C(CH$_3$)), 31.63 (C(CH$_3$)), 18.40 (ArCH$_3$) ppm.

Example 15

Figure 6:
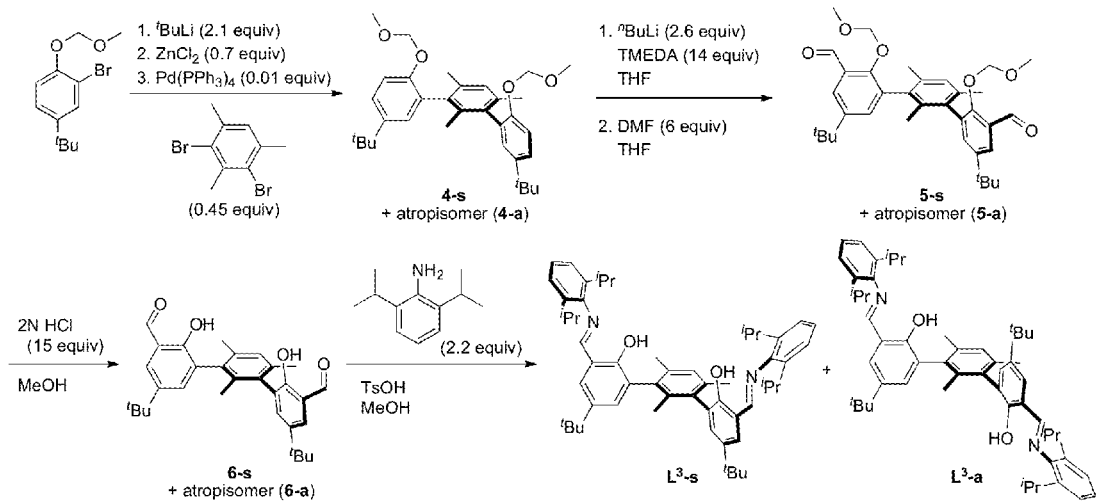
FIG. 6 shows a schematic illustration of an exemplary reaction scheme for the preparation of atropisomers of an m-terphenyl bisphenoxyimine ligand according to an embodiment herein described, and in particular the synthesis of m-terphenyl bisphenoxyimine ligands $L^3$-s and $L^3$-a.

Synthesis of Bisphenoxyiminato Compounds (Meta—FIG. 6)

1,3-dibromomesitylene was synthesized according to literature procedures. [Ref 38]

4-a and 4-s. Synthesis of the biphenyl compounds 4 was accomplished via the Negishi coupling of 1,3-dibromomesitylene with two equivalents of 2-bromo-4-tert-butyl-methoxymethylphenol using conditions analogous to the synthesis of compounds 1. Precipitation from methanol yielded 4-a as a white solid (2.5 g). 4-s was collected in greater than 80% purity via column chromatography (30:1 hexanes/ethyl acetate). 4-s was then isolated as a colorless oil (2.3 g, 58% overall yield) via column chromatography of the 3:2 hexanes/ethyl acetate flush of the previous column (6.25:1 hexanes/ethyl acetate). 4-a $^1$H NMR (300 MHz, CDCl$_3$): δ 7.36 (dd, J=8.6, J=2.5, 2H, ArH), 7.21 (d, J=8.6, 2H, ArH), 7.17 (d, J=2.5, 2H, ArH), 7.14 (s, 1H, ArH), 5.18 (d, J=6.8, 2H, OCH$_2$OCH$_3$), 5.13 (d, J=6.8, 2H, OCH$_2$OCH$_3$), 3.40 (s, 6H, OCH$_2$OCH$_3$), 2.10 (s, 6H, ArCH$_3$), 1.78 (s, 3H, ArCH$_3$), 1.36 (s, 18H, ArC(CH$_3$)$_3$) ppm. 4-s $^1$H NMR (300 MHz, CDCl$_3$): δ 7.30 (dd, J=8.6, J=2.5, 2H, ArH), 7.16 (d, J=2.5, 2H, ArH), 7.12 (d, J=8.6, 2H, ArH), 7.08 (s, 1H, ArH), 5.02 (d, J=6.7, 2H, OCH$_2$OCH$_3$), 4.98 (d, J=6.7, 2H, OCH$_2$OCH$_3$), 3.30 (s, 6H, OCH$_2$OCH$_3$), 2.06 (s, 6H, ArCH$_3$), 1.72 (s, 3H, ArCH$_3$), 1.31 (s, 18H, ArC(CH$_3$)$_3$) ppm.

5-a. Formylation of 4-a was accomplished via the same procedure as for 2. 0.53 g of doubly orthoformylated compound was collected as a pale yellow solid after extraction and moved forward without further purification (53% yield). $^1$H NMR (300 MHz, CDCl$_3$): δ 10.44 (s, 2H, CHO), 7.87 (d, J=2.6, 2H, ArH), 7.32 (d, J=2.6, 2H, ArH), 7.08 (s, 1H, ArH), 4.72 (d, J=2.4, 2H, OCH$_2$OCH$_3$), 4.69 (d, J=2.4, 2H, OCH$_2$OCH$_3$), 3.20 (s, 3H, OCH$_2$OCH$_3$), 2.09 (s, 6H, ArCH$_3$), 1.80 (s, 3H, ArCH$_3$), 1.32 (s, 18H, ArC(CH$_3$)$_3$) ppm.

5-s. Formylation of 4-s was accomplished via the same procedure as for the anti, but a mixture of species resulted. Column chromatography was used to isolate the desired product as a pale yellow solid (0.30 g, 51% yield). $^1$H NMR (300 MHz, CDCl$_3$): δ 10.46 (s, 2H, CHO), 7.89 (d, J=2.7, 2H, ArH), 7.45 (d, J=2.7, 2H, ArH), 7.15 (s, 1H, ArH), 4.65 (s, 4H, OCH$_2$OCH$_3$), 3.36 (s, 6H, OCH$_2$OCH$_3$), 2.11 (s, 6H, ArCH$_3$), 1.79 (s, 3H, ArCH$_3$), 1.34 (s, 18H, ArC(CH$_3$)$_3$) ppm.

6-a. Deprotection of 5-a was accomplished via the same procedure for 3. The desired product was isolated as an olive green solid in 95% yield (0.86 g). $^1$H NMR (300 MHz, CDCl$_3$): δ 11.07 (s, 2H, ArOH), 9.95 (s, 2H, CHO), 7.55 (d, J=2.5, 2H, ArH), 7.52 (d, J=2.5, 2H, ArH), 7.14 (s, 1H, ArH), 2.07 (s, 6H, ArCH$_3$), 1.75 (s, 3H, ArCH$_3$), 1.34 (s, 18H, ArC(CH$_3$)$_3$) ppm.

6-s. Deprotection of 5-s was accomplished via the same procedure as for the anti. The desired product was isolated as a brown solid in quantitative yield (0.69 g). $^1$H NMR (300 MHz, CDCl$_3$): δ 10.95 (s, 2H, ArOH), 9.97 (s, 2H, CHO), 7.57 (d, J=2.5, 2H, ArH), 7.49 (d, J=2.5, 2H, ArH), 7.16 (s, 1H, ArH), 2.08 (s, 6H, ArCH$_3$), 1.80 (s, 3H, ArCH$_3$), 1.35 (s, 18H, ArC(CH$_3$)$_3$) ppm.

L$^3$-a. The imine condensation with 2,6-diisopropylaniline and 6-a was accomplished via the same procedure as for L$^1$-a. The desired product was isolated as a pale yellow solid in 66% yield (0.26 g). $^1$H NMR (300 MHz, CDCl$_3$): δ 13.44 (s, 2H, ArOH), 7.99 (s, 2H, NCH) 7.38 (d, J=2.4, 2H, ArH), 7.23 (d, J=2.4, 2H, ArH), 7.20 (s, 1H, ArH), 7.09 (s, 6H, ArH), 3.02 (septet, J=6.8, 4H, ArCH(CH$_3$)$_2$), 2.37 (s, 3H, ArCH$_3$), 2.32 (s, 6H, ArCH$_3$), 1.17 (s, 18H, ArC(CH$_3$)$_3$), 1.04 (dd, J=6.8, J=3.4, 24H, ArCH(CH$_3$)$_2$) ppm.

L$^3$-s. The imine condensation with 2,6-diisopropylaniline and 6-s was accomplished via the same procedure as for the anti. The desired product was isolated as a pale yellow solid in 42% yield (0.17 g). $^1$H NMR (300 MHz, CDCl$_3$): δ 13.29 (s, 2H, ArOH), 8.03 (s, 2H, NCH), 7.49 (d, J=2.5, 2H, ArH), 7.25 (d, J=2.5, 2H, ArH), 7.13 (s, 1H, ArH), 7.10 (s, 6H, ArH), 3.02 (septet, J=8.4, 4H, ArCH(CH$_3$)$_2$), 2.38 (s, 3H, ArCH$_3$), 2.31 (s, 6H, ArCH$_3$), 1.23 (s, 18H, ArC(CH$_3$)$_3$), 1.04 (dd, J=8.4, J=7.0, 24H, ArCH(CH$_3$)$_2$) ppm.

Example 16

Figure 7:
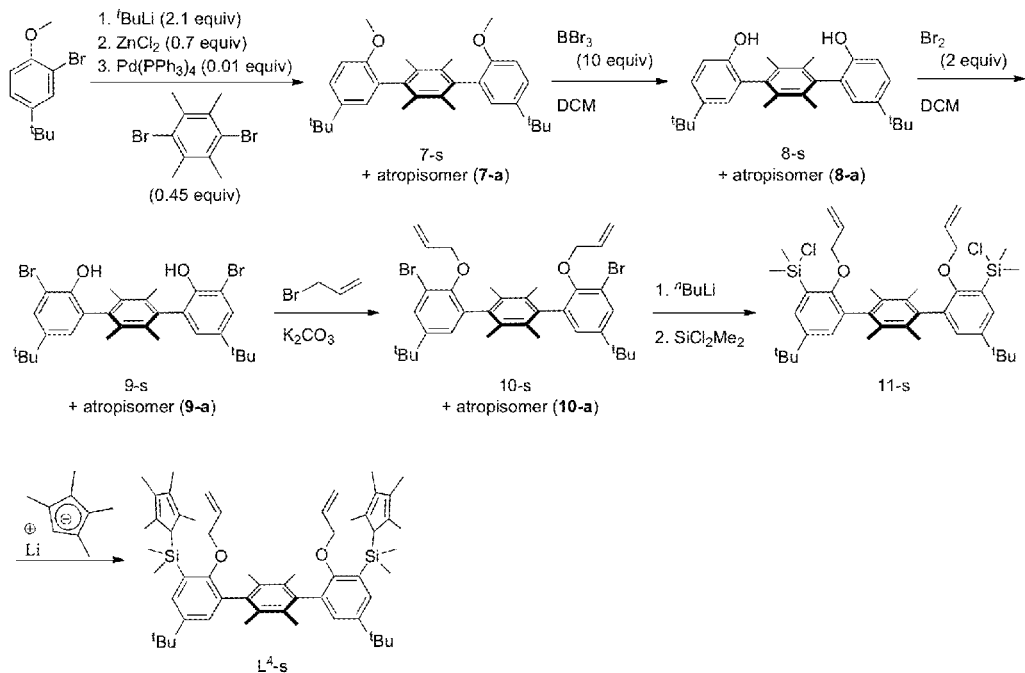
FIG. 7 shows schematic illustration of an exemplary reaction scheme for the preparation of atropisomers of a p-terphenyl bisphenoxy-cyclopentadiene ligand according to an embodiment herein described, and in particular p-terphenyl bisphenoxy-cyclopentadiene ligand $L^4$-s.

Synthesis of Bisphenoxycyclopentadienyl Compounds (Para —FIG. 7)

2-bromo-4-tert-butylmethoxybenzene was synthesized from 2-bromo-4-tert-butylphenol according an analogous synthesis.[Ref 39] The $^1$H NMR spectrum matched literature assignments.[Ref 40] HRMS (EI+) Calcd. for C$_{11}$H$_{15}$OBr: 242.0306. Found: 242.0305.

7-a and 7-s. Synthesis of the biphenyl compounds 7 was accomplished via the Negishi coupling of 1,4-dibromo-2,3,5,6-tetramethybenzene with two equivalents of 2-bromo-4-tert-butylmethoxybenzene using conditions analogous to the synthesis of compounds 1. The two atropisomers of the terphenyl compound were coprecipitated from methanol as a colorless solid (15.4 g, 71% yield). $^1$H NMR (300 MHz, CDCl$_3$): δ 7.36 (2dd, 2H, ArH), 7.19 (2d, 2H, ArH), 6.95 (2d, 2H, ArH), 3.78 (2s, 6H, OCH$_3$), 1.99 (2s, 12H, ArCH$_3$), 1.34 (2s, 18H, C(CH$_3$)$_3$) ppm. $^{13}$C NMR (75 MHz, CDCl$_3$): δ 154.70 (Ar), 143.25 (Ar), 137.83 (Ar), 137.57 (Ar), 132.22 (Ar), 132.10 (Ar), 130.75 (Ar), 129.31 (Ar), 128.97 (Ar), 124.29 (Ar), 124.21 (Ar), 110.19 (Ar), 110.09 (Ar), 55.81 (OCH$_3$), 55.59 (OCH$_3$), 34.29 (ArC(CH$_3$)$_3$), 31.75 (ArC(CH$_3$)$_3$), 18.07 (ArCH$_3$), 18.00 (ArCH$_3$) ppm. HRMS (EI+) Calcd. for C$_{32}$H$_{42}$O$_2$: 458.3185. Found: 458.3184.

8-a and 8-s. A mixture of 7-a and 7-b (10.90 g, 23.76 mmol, 1 equiv) was dissolved in 100 mL of DCM and cooled to 0° C. Neat boron tribromide (9.0 mL, 95.03 mmol, 4 equiv) was added to the solution. The reaction mixture was allowed to warm to ambient temperature and stirred for 1 h. The mixture was quenched with saturated sodium bicarbonate solution. The organic fraction was collected, dried with MgSO$_4$, filtered through Celite, and concentrated in vacuo. The syn and anti atropisomers were separated by column chromatography (4:1 DCM/hexanes). 8-anti (6.5 g) $^1$H-NMR (300 MHz, CDCl$_3$): δ 7.31 (dd, 2H, J=8.4, 2.4 Hz, Ar—H) 7.05 (d, 2H, J=2.4 Hz, ArH) 6.94 (d, 2H, J=8.5 Hz, ArH) 4.52 (s, 2H, ArOH) 1.99 (s, 12H, Ar—CH$_3$) 1.32 (s, 18H, C(CH$_3$)$_3$) ppm. 8-syn (1.73 g) $^1$H-NMR (300 MHz, CDCl$_3$): δ 7.50 (d, 2H, J=2.3 Hz, ArH) 7.02 (d, 2H, J=2.3 Hz, ArH) 5.26 (br, 2H, ArOH) 1.98 (s, 12H, ArCH$_3$) 1.30 (s, 18H, C(CH$_3$)$_3$) ppm.

9-a. 8-a (1.094 g, 2.54 mmol, 1 equiv) was dissolved in 100 mL of DCM and cooled to −78° C. A 0.5 M solution of bromine in DCM (9.91 mL, 4.95 mmol, 1.95 equiv) was added by syringe. The mixture was stirred at reduced temperature for 1 h and then allowed to reach ambient temperature. The mixture was stirred for 8 h at ambient temperature. A saturated solution of sodium bicarbonate was added. The organic phase was collected, dried with MgSO$_4$, filtered through Celite, and concentrated in vacuo. The compound was purified by flash column chromatography (5:1:0.5 hexanes/ethyl acetate/DCM) as a white solid (1.345 g, 90% yield) $^1$H-NMR (300 MHz, CDCl$_3$): δ 7.49 (d, 2H, J=2.3 Hz, ArH) 7.07 (d, 2H, J=2.3 Hz, ArH) 5.20 (s, 2H, ArOH) 1.98 (s, 12H, Ar—CH$_3$) 1.31 (s, 18H, C(CH$_3$)$_3$) ppm.

9-s. 8-s (1.728 g, 4.01 mmol, 1 equiv) was dissolved in 100 mL of DCM and cooled to −78° C. Bromine (0.403 mL, 7.82 mmol, 1.95 equiv) was added by syringe. The mixture was stirred at reduced temperature for 1 h and then allowed to reach ambient temperature. The mixture was stirred for 8 h at ambient temperature. A saturated solution of sodium bicarbonate was added. The organic phase was collected, dried with MgSO$_4$, filtered through Celite, and concentrated in vacuo. The compound was purified by flash column chromatography (5:1:0.5 hexanes/ethyl acetate/DCM as a white solid (2.20 g, 94% yield) $^1$H-NMR (300 MHz, CDCl$_3$): δ 7.52 (d, 2H, J=2.3 Hz, ArH) 7.05 (d, 2H, J=2.3 Hz, ArH) 5.27 (s, 2H, ArOH) 2.00 (s, 12H, ArCH$_3$) 1.32 (s, 18H, C(CH$_3$)$_3$) ppm.

10-a. 9-a (1.495 g, 2.54 mmol, 1 equiv) was dissolved in acetone (200 mL). Allyl bromide (0.484 mL, 5.6 mmol, 2.2 equiv) was added by syringe. This mixture was added using an addition funnel to a stirred solution of sodium hydroxide (0.224 g, 5.6 mmol, 2.2 equiv) in water (2 mL). After addition was complete, the mixture was rapidly stirred for 24 h at which time volatiles were removed in vacuo. The mixture was extracted with DCM, Dried with MgSO$_4$, filtered through Celite, and concentrated in vacuo. The product was purified by crystallization from DCM/hexane (0.930 g, 55% yield). Additional crops of crystals can be collected. 10-a has not currently been moved forward to L$^4$-a. $^1$H NMR (300 MHz, CDCl$_3$): δ 7.55 (d, 2H, J=2.4 Hz, ArH) 6.99 (d, 2H, J=2.4 Hz, ArH) 5.73 (m, 2H, OCH$_2$CH=CH$_2$) 5.05 (m, 4H, OCH$_2$CH=CH$_2$) 4.08 (m, 4H, OCH$_2$CH=CH$_2$) 1.96 (s, 12H, ArCH$_3$) 1.32 (s, 18H, C(CH$_3$)$_3$) ppm.

10-s. 9-s (2.450 g, 4.16 mmol, 1 equiv) was dissolved in acetone (200 mL). Allyl bromide (3.6 mL, 41.6 mmol, 10 equiv) was added by syringe. This mixture was added using an addition funnel to a stirred solution of sodium hydroxide (1.7 g, 41.6 mmol, 10 equiv) in water (5 mL). After addition was complete, the mixture was rapidly stirred for 24 h at which time volatiles were removed in vacuo. The mixture was extracted with DCM, dried with MgSO$_4$, filtered through Celite, and concentrated in vacuo. The compound was purified by flash column chromatography (5:1:0.5 hexanes/ethyl acetate/DCM) as a white solid. (2.557 g, 92% yield) $^1$H NMR (300 MHz, C$_6$D$_6$): δ 7.72 (d, 2H, J=2.4 Hz, ArH) 7.10 (d, 2H, J=2.4 Hz, ArH) 5.80 (ddt, 2H, J=17.1, 10.5, 5.4 Hz, OCH$_2$CH=CH$_2$) 5.21 (dd, 2H, J=17.1, 1.7 Hz, OCH$_2$CH=CH$_2$) 4.96 (dd, 2H, J=17.1, 1.7 Hz, OCH$_2$CH=CH$_2$) 4.22 (dt, 4H, J=5.3, 1.5 Hz, OCH$_2$CH=CH$_2$) 2.04 (s, 12H, ArCH$_3$) 1.11 (s, 18H, C(CH$_3$)$_3$) ppm.

11-s. 10-s (0.093 g, 0.14 mmol, 1 equiv) was dissolved in toluene (5 mL) in a Schlenk tube and THF (1 mL) was added to the reaction flask. The Schlenk tube was cooled to −78° C. After the temperature had equilibrated, "BuLi (0.116 mL, 0.29 mmol, 2.1 equiv) was added via syringe. The reaction was stirred for 1 h at −78° C. beore it was transferred via cannula to a second Schlenk tube containing dichlorodimethylsilane (0.361 mL, 2.8 mmol, 20 equiv) toluene (5 mL) at −78° C. The reaction mixture was allowed to slowly reach ambient temperature at which point volatiles were removed under vacuum. The residue was taken up in pentane, filtered through celite, and concentrated in vacuo. The product was collected as a white powder (- - - g, - - - % yield).

$^1$H-NMR (300 MHz, $C_6D_6$): δ 8.13 (d, 2H, J=2.5 Hz, Ar—H) 7.34 (d, 2H, J=2.5 Hz, Ar—H) 5.61 (ddt, 2H, J=17.2, 10.4, 5.1 Hz, $OCH_2CH=CH_2$) 5.11 (dd, 2H, J=17.2, 1.7 Hz, $OCH_2CH=CH_2$) 4.88 (dd, 2H, J=10.5, 1.6 Hz, $OCH_2CH=CH_2$) 4.14-4.07 (m, 4H, $OCH_2CH=CH_2$) 2.12 (s, 12H, Ar—$CH_3$) 1.30 (s, 18H, $C(CH_3)_3$) 0.79 (s, 12H, Si—$CH_3$) ppm.

$L^4$-s. 11-s (0.154 g, 0.22 mmol, 1 equiv) was dissolved in THF (5 mL) and added to a suspension of lithium tetramethylcyclopentadienyl (0.062 mg, 0.29 mmol, 1.3 equiv) in THF (10 mL). The reaction mixture was stirred for 12 h before filtering through celite, concentrating, taking up in pentane and filtering again through celite. The white solid (0.158 g, 83% yield) was carried on without further purification. $^1$H NMR (300 MHz, $C_6D_6$) δ 7.62 (d, J=2.6 Hz, 2H), 7.29 (d, J=2.6 Hz, 2H), 5.91-5.57 (m, 2H), 5.28 (dd, J=17.2, 1.8 Hz, 2H), 4.97 (dd, J=10.6, 1.7 Hz, 2H), 4.22 (d, J=4.9 Hz, 4H), 3.72 (s, 1H), 2.21 (s, 12H), 1.97 (s, 12H), 1.91 (s, 12H), 1.29 (s, 18H), 0.42 (s, 12H) ppm.

Example 17

Figure 8:
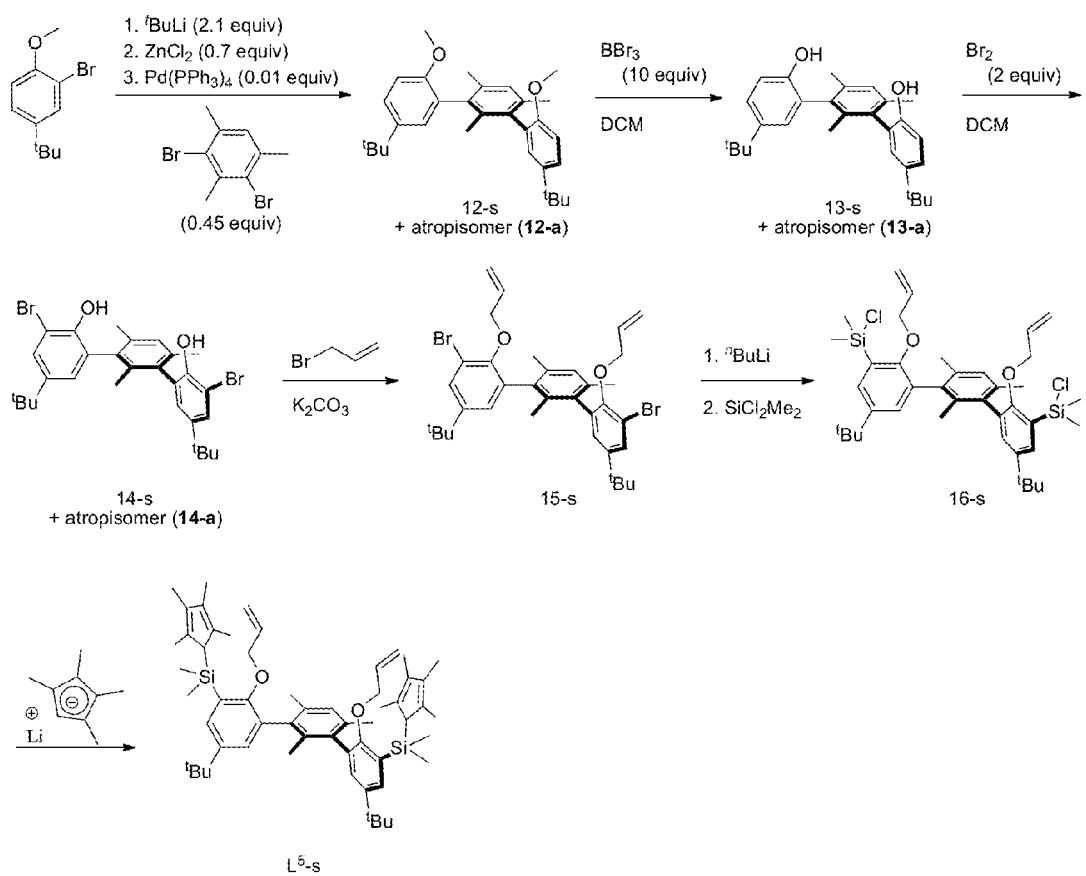
FIG. 8 shows a schematic illustration of an exemplary reaction scheme for the preparation of atropisomers of an m-terphenyl bisphenoxy-cyclopentadiene ligand according to an embodiment herein described, and in particular m-terphenyl bisphenoxy-cyclopentadiene ligands $L^5$-s.

Synthesis of Bisphenoxycyclopentadienyl Compounds (Meta —FIG. 8)

12-a and 12-s. Synthesis of the biphenyl compounds 12 was accomplished via the Negishi coupling of 1,3-dibromomesitylene (5.488 g, 19.74 mmol, 0.48 equiv) with 2-bromo-4-tert-butylmethoxybenzene (10.000 g, 41.13 mmol, 1 equiv) using conditions analogous to the synthesis of compounds 1. Anti and syn isomers generated in the coupling reaction were not separated and instead were carried on together. (5.571 g, 63% yield) $^1$H NMR (300 MHz, $CDCl_3$): δ 7.34 (dd, 2H, J=8.6, 2.6 Hz, ArH) 7.17 (d, 2H, J=2.5 Hz, ArH) 7.11 (s, 1H, ArH) 6.92 (d, 2H, J=8.5 Hz, ArH) 2.73 (s, 6H, $OCH_3$-anti) 2.84 (s, 6H, $OCH_3$-syn) 2.06 (s, 6H, $ArCH_3$) 1.71 (s, 3H, $ArCH_3$) 1.330 (s, 18H, $C(CH_3)_3$-anti) 1.326 (s, 18 H, $C(CH_3)_3$-anti) ppm.

13-a and 13-s. A mixture of 12-a and 12-s (5.591 g, 12.53 mmol, 1 equiv) was dissolved in DCM (100 mL) and cooled to 0° C. Neat boron tribromide (4.75 mL, 50.12 mmol, 4 equiv) was added to the solution. The reaction mixture was allowed to warm to ambient temperature and stirred for 1 h. The mixture was quenched with saturated sodium bicarbonate solution. The organic fraction was collected, dried with $MgSO_4$, filtered through Celite, and concentrated in vacuo. The syn and anti atropisomers were separated by flash column chromatography on silica gel (5:1:0.5 hexanes/ethyl acetate/DCM). 13-a $^1$H NMR (300 MHz, $CDCl_3$): δ 7.29 (dd, 2H, J=8.5, 2.5 Hz, ArH) 7.17 (s, 1H, ArH) 7.04 (d, 2H, J=2.5 Hz, ArH) 6.92 (d, 2H, J=8.5 Hz, ArH) 4.55 (s, 2H, OH) 2.07 (s, 6H, $ArCH_3$) 1.75 (s, 3H, $ArCH_3$) 1.30 (s, 18H, $C(CH_3)_3$) ppm. 13-s $^1$H NMR (300 MHz, $CDCl_3$): δ 7.24 (dd, 2H, J=8.5, 2.5 Hz, ArH) 7.15 (s, 1H, ArH) 7.07 (d, 2H, J=2.5 Hz, ArH) 6.86 (d, 2H, J=8.5 Hz, ArH) 5.02 (br, 2H, OH) 2.07 (s, 6H, $ArCH_3$) 1.69 (s, 3H, $ArCH_3$) 1.29 (s, 18 H, $C(CH_3)_3$) ppm.

14-a. The desired material was prepared utilizing a procedure identical to that for 9-a and 9-s with 13-a (1.870 g, 4.49 mmol, 1 equiv) and bromine (0.451 mL, 8.75 mmol, 1.95 equiv) The product was isolated by flash column chromatography on silica gel (5:1:0.5 hexanes/ethyl acetate/DCM) (2.488 g, 96% yield). 14-a has not currently been moved forward to $L^5$-a. $^1$H NMR (300 MHz, $CDCl_3$): δ 7.47 (d, 2H, J=2.3 Hz, ArH) 7.14 (s, 1H, ArH) 7.06 (d, 2H, J=2.3 Hz, ArH) 5.21 (s, 2H, ArOH) 2.07 (s, 6H, $ArCH_3$) 1.74 (s, 3H, $ArCH_3$) 1.29 (s, 18H, $C(CH_3)_3$) ppm.

14-s. The desired material was prepared utilizing a procedure identical to that for 9-a and 9-s with 13-s (1.753 g, 4.21 mmol, 1 equiv) and bromine (0.423 mL, 8.21 mmol, 1.95 equiv) The product was isolated by flash column chromatography on silica gel (5:1:0.5 hexanes/ethyl acetate/DCM) (2.489 g, quantitative yield). $^1$H NMR (300 MHz, $CDCl_3$): δ 7.48 (d, 2H, J=2.3 Hz, ArH) 7.17 (s, 1H, ArH) 7.07 (d, 2H, J=2.3 Hz, ArH) 5.31 (s, 2H, ArOH) 2.08 (s, 6H, $ArCH_3$) 1.75 (s, 3H, $ArCH_3$) 1.30 (s, 18 H, $C(CH_3)_3$) ppm.

15-s. The desired material was prepared utilizing a procedure identical to that for 10-s with 14-s (2.489 g, 4.3 mmol, 1 equiv), allyl bromide (3.7 mL, 43 mmol, 10 equiv) and sodium hydroxide (1.72 g, 43 mmol, 10 equiv). The product was isolated by flash column chromatography on silica gel (30:1 hexanes/ethyl acetate) (2.2 g, 78% yield). $^1$H NMR (300 MHz, $C_6D_6$): δ 7.68 (d, 2H, J=2.5 Hz, ArH) 7.11 (s, 1H, ArH) 6.98 (d, 2H, J=2.5 Hz, ArH) 5.87 (ddt, 2H, J=17.2, 10.6, 5.4 Hz, $OCH_2CH=CH_2$) 5.24 (ddd, 2H, J=17.2, 3.3 1.6 Hz, $OCH_2CH=CH_2$) 4.97 (m, 2H, $OCH_2CH=CH_2$) 4.24 (m, 4H, $OCH_2CH=CH_2$) 2.14 (s, 6H, $ArCH_3$) 2.09 (s, 3H, $ArCH_3$) 1.04 (s, 18 H, $C(CH_3)_3$) ppm.

16-s. The desired material was prepared utilizing a procedure identical to that for 11-s with 15-s (1.000 g, 1.53 mmol, 1 equiv), "BuLi (1.34 mL, 3.36 mmol, 2.2 equiv), and dichlorodimethylsilane (1.9 mL, 15.3 mmol, 10 equiv). The product was used without further purification (0.720 g, 69% yield). $^1$H NMR (300 MHz, $C_6D_6$): δ 8.08 (d, 2H, J=2.4 Hz, ArH) 7.34 (d, 2H, J=2.4 Hz, ArH) 7.02 (s, 1H, ArH) 5.63 (ddd, 2H, J=22.2, 10.3, 5.0 Hz, $OCH_2CH=CH_2$) 5.13 (dd, 2H, J=17.2, 1.5 Hz, $OCH_2CH=CH_2$) 4.91 (dd, 2H, J=10.5, 1.3 Hz, $OCH_2CH=CH_2$) 4.09 (d, 4H, J=4.9 Hz, $OCH_2CH=CH_2$) 2.21 (s, 6H, $ArCH_3$) 2.21 (s, 3H, $ArCH_3$) 1.22 (s, 18 H, $C(CH_3)_3$) 0.75 (s, 6H, $SiCH_3$) 0.73 (s, 6H, $SiCH_3$) ppm.

$L^5$-s. The desired material was prepared utilizing a procedure identical to that for $L^4$-s with 16-s (0.253 g, 0.30 mmol, 1 equiv), "BuLi (0.486 mL, 1.22 mmol, 4.1 equiv) and $TiCl_4$ $(THF)_2$ (0.200 g, 0.60 mmol, 2.0 equiv) The product used without further purification (0.520 g, 85% yield). $^1$H NMR (300 MHz, $C_6D_6$): δ 7.59 (d, 2H, J=2.5 Hz, ArH) 7.31 (d, 2H, J=2.5 Hz, ArH) 7.05 (s, 1H, ArH) 5.75 (ddd, 2H, J=15.4, 10.1, 4.7 Hz, $OCH_2CH=CH_2$) 5.31 (dd, 2H, J=17.3, 1.6 Hz, $OCH_2CH=CH_2$) 5.00 (dd, 2H, J=10.6, 1.4 Hz, $OCH_2CH=CH_2$) 4.25 (d, 4H, J=4.7 Hz, $OCH_2CH=CH_2$) 3.69 (s, 2H, Cp*H) 2.34 (s, 3H, $ArCH_3$) 2.30 (s, 6H, $ArCH_3$) 1.92 (s, 12H, Cp*$CH_3$) 1.88 (s, 12H, Cp*$CH_3$) 1.22 (s, 18 H, $C(CH_3)_3$) 0.39 (s, 6H, $SiCH_3$) 0.37 (s, 6H, $SiCH_3$) ppm.

Example 18

Figure 9:
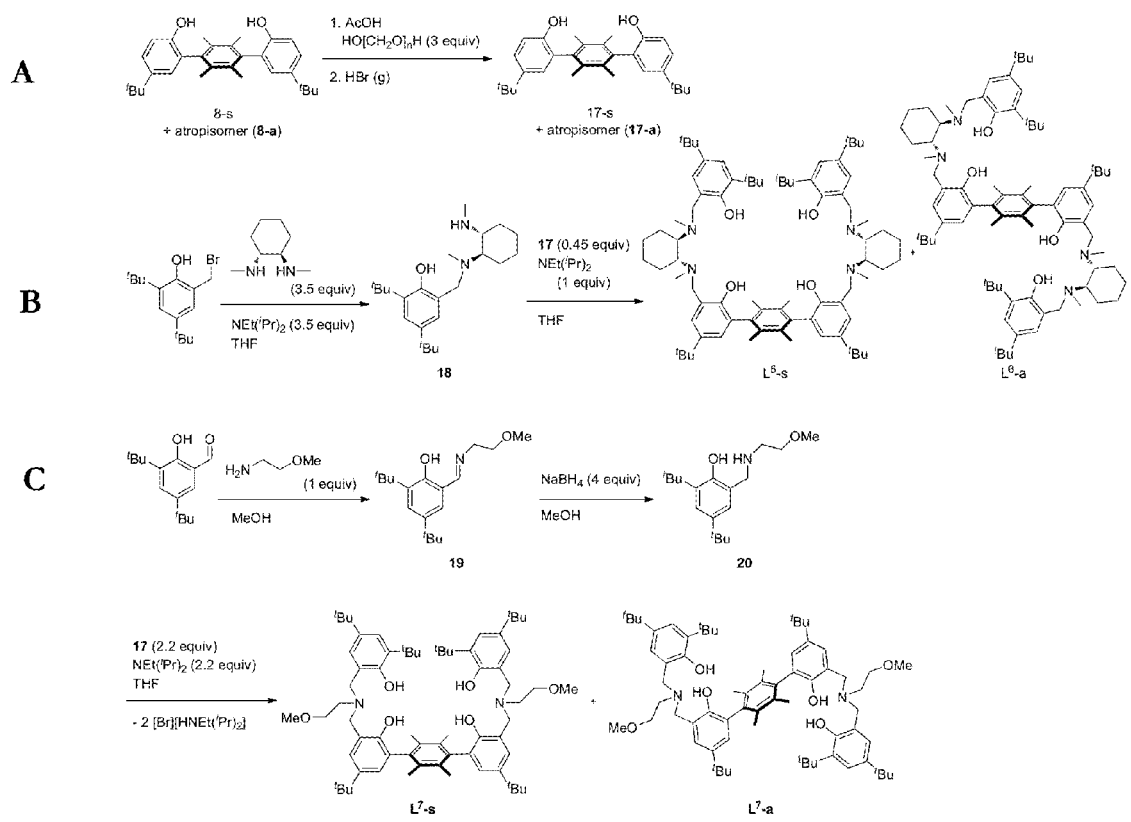
FIG. 9 shows a schematic illustration of an exemplary reaction scheme for the preparation of atropisomers of p-terphenyl bis-salan ligands according to embodiments herein described. Panel A shows an exemplary reaction scheme for the preparation of compound 17, an intermediate compound used in the synthesis of the p-terphenyl bis-salan ligands. Panel B shows an exemplary reaction scheme for the preparation of atropisomers of p-terphenyl bis-salan ligands $L^6$-s and $L^6$-a. Panel C shows an exemplary reaction scheme for the preparation of p-terphenyl bis-salan ligands $L^7$-s and $L^7$-a.

Synthesis of Bis-Salan Compounds (Para —FIG. 9)

2-(Bromomethyl)-4,6-di-tert-butylphenol[Ref 41] and (1R,2R)—$N^1,N^2$-dimethylcyclohexane-1,2-diamine[Ref 42] were synthesized according to literature procedures.

17-a. 8-a (3.39 g, 7.88 mmol, 1 equiv), paraformaldehyde (0.71 g, 7.88 mmol, 3 equiv), and glacial acetic acid (20 mL) were combined in a 3-neck round bottom flask equipped with a stir bar. A thermometer was secured in one arm of the flask, another arm was equipped with a small Teflon tube and the third was connected via hosing to a series of bubblers with water and dilute base. HBr(g) was bubbled through the Teflon tube directly into the stirring mixture for 15 minutes over which time the maximum exotherm was 60° C. at which point the tube was lifted out of the solution and the flask was sealed and left to stir an additional 12 h. The desired material was extracted into hexanes and the aqueous fractions were washed with DCM. The organic fractions were combined, dried with $MgSO_4$, filtered, and the volatiles were removed under vacuum. The residue was dissolved in warm hexanes and then cooled so that the desired product precipitated. 17-a was collected via filtration as a white solid in 63% yield (3.08 g). $^1$H NMR (300 MHz, $CDCl_3$): δ 7.34 (d, J=2.5, 2H, ArH), 7.03 (d, J=2.4, 2H, ArH), 4.81 (s, 2H, OH), 4.66 (s, 4H, $ArCH_2Br$), 1.98 (s, 12H, Ar—$CH_3$), 1.33 (s, 18H, $C(CH_3)_3$) ppm.

17-s. Bromination of 8-s was accomplished via the same procedure as the anti. The desired product was isolated as a white solid in 51% yield (1.49 g). $^1$H NMR (300 MHz, $CDCl_3$): δ 7.34 (d, J=2.5, 2H, ArH), 7.05 (d, J=2.5, 2H, ArH), 4.84 (s, 2H, OH), 4.67 (s, 4H, $ArCH_2Br$), 2.00 (s, 12H, Ar—$CH_3$), 1.32 (s, 18H, $C(CH_3)_3$) ppm.

18. 2-(Bromomethyl)-4,6-di-tert-butylphenol (0.30 g, 1.00 mmol, 1 equiv) in THF (10 mL) was dripped into a solution of (1R,2R)—$N^1,N^2$-dimethylcyclohexane-1,2-diamine (0.50 g, 3.51 mmol, 3.5 equiv) and Hünig's base (0.36 g, 3.51 mmol, 3.5 equiv) in THF (10 mL) cooled to 0° C. in an ice bath over 5 minutes. Over this time the solution turned cloudy. The reaction was stirred for 2 h at 0° C. and then an additional 2.5 h at room temperature. The reaction mixture was filtered over celite and volatiles were removed under vacuum to yield a pale yellow oily solid. The solid was washed over silica gel with 2:1 EtOAC/hexanes and then flushed through with 2:1 DCM/MeOH. The flush through was concentrated in vacuo to yield 18 as a nearly colorless oily solid in 66% yield (0.24 g). $^1$H NMR (300 MHz, $CDCl_3$): δ 7.24 (d, J=2.4, 1H, ArH), 6.88 (d, J=2.4, 1H, ArH), 3.83 (d, J=13.1, 1H, $ArCH_2$), 3.60 (d, J=13.1, 1H, $ArCH_2$), 2.95 (m, 1H, CH), 2.71 (m, 1H, CH), 2.42 (s, 3H, $NCH_3$), 2.31 (s, 3H, $NCH_3$), 2.21 (m, 2H, $CH_2$), 2.04 (m, 2H, $CH_2$), 1.84 (m, 2H, $CH_2$), 1.49 (s, 2H, $CH_2$), 1.42 (s, 9H, $C(CH_3)_3$), 1.28 (s, 9H, $C(CH_3)_3$) ppm.

$L^6$-a. A solution of 18 (0.10 g, 0.28 mmol, 2.2 equiv) and Hünig's base (0.028 g, 0.28 mmol, 2.2 equiv) in THF (7 mL) was cooled in an ice bath and 17-a (0.078 g, 0.13 mmol, 1 equiv) in THF (6 mL) was dripped into the solution over 5 minutes. The mixture was stirred while gradually warming to room temperature over 4 h, filtered over celite and concentrated in vacuo. The solid was washed over silica gel with 5:1 EtOAC/hexanes and concentrated in vacuo after which the product was isolated by column chromatography (1:3 EtOAc/hexanes) as a pale solid in 85% purity and 42% yield (0.06 g). $^1$H NMR (300 MHz, $C_6D_6$): δ 10.13 (s, 4H), 7.49 (d, J=2.4, 2H), 7.13 (d, J=2.6, 2H), 7.04 (d, J=2.7, 2H), 6.92 (d, J=2.5, 2H), 3.59 (m, 8H), 3.26 (m, 2H), 2.64 (s, 6H), 2.38 (s, 6H), 2.24 (m, 8H), 2.02 (s, 6H), 1.82 (s, 6H), 1.61 (s, 18H), 1.34 (s, 36H), 0.74 (m, 10H) ppm.

$L^6$-s. Formation of $L^6$-s was accomplished via the same procedure as the anti and the product was purified by column chromatography (1:2 EtOAc/hexanes) to yield the desired product as a pale solid in 80% purity (0.05 g, 32% yield). $^1$H NMR (300 MHz, $C_6D_6$): δ 9.95 (s, 4H), 7.50 (d, J=2.4, 2H), 7.30 (d, J=2.6, 2H), 7.16 (d, 2H), 6.96 (d, J=2.4, 2H), 3.59 (m, 3H), 2.53 (s, 6H), 2.32 (s, 6H), 2.10 (s, 6H), 1.94 (s, 6H), 1.64 (s, 9H), 1.36 (s, 9H), 1.35 (s, 9H), 0.80 (m, 10H) ppm.

19. 2-methoxy ethylamine (0.50 mL, 5.75 mmol, 1 equiv), 3,5-ditertbutyl-2-hydroxybenzaldehyde (1.35 g, 5.75 mmol, 1 equiv) and MeOH (20 mL) were added to a round bottom flask equipped with a stirbar and a reflux condenser and heated to reflux with stirring for 5 hours over which time the reaction mixture turned bright yellow. The reaction mixture was cooled to room temperature and volatiles were removed under vacuum to yield 1.67 g of imine 19 as a bright yellow oil (99% yield). $^1$H NMR (300 MHz, $CDCl_3$): δ 8.38 (t, J=1.2, 1H, NCH), 7.38 (d, J=2.4, 1H, ArH), 7.09 (d, J=2.4, 1H, ArH), 3.76 (t, J=5.1, 2H, $CH_2$), 3.68 (t, J=5.1, 2H, $CH_2$), 3.38 (s, 3H, $OCH_3$), 1.42 (s, 9H, $C(CH_3)_3$), 1.31 (s, 9H, $C(CH_3)_3$) ppm. $^{13}$C NMR (101 MHz, $CDCl_3$): δ 167.56 (NCH), 158.24 (Ar), 140.10 (Ar), 136.75 (Ar), 127.01 (Ar), 126.12 (Ar), 118.02 (Ar), 72.16 ($OCH_3$), 59.23 ($CH_2$), 59.12 ($CH_2$), 35.16 ($C(CH_3)_3$), 34.26 ($C(CH_3)_3$), 31.65 ($C(CH_3)_3$), 29.58 ($C(CH_3)_3$) ppm.

20. 19 (1.65 g, 5.66 mmol, 1 equiv), $NaBH_4$ (0.86 g, 22.65 mmol, 4 equiv) and MeOH (20 mL) were added to a round bottom flask equipped with a stirbar. The bright yellow suspension was stirred at room temperature, turning colorless and mostly clear within 0.5 h. After a total of 2 h of stifling, 1M HCl was added to quench the reaction and the product was extracted with DCM (3×). The combined organic fractions were dried with $MgSO_4$, filtered, and volatiles were removed under vacuum to yield 1.60 g of amine 20 as a colorless oil (96% yield). $^1$H NMR (300 MHz, $CDCl_3$): δ 7.22 (d, J=2.5, 1H, ArH), 6.86 (d, J=2.5, 1H, ArH), 3.97 (s, 2H, $ArCH_2N$), 3.52 (t, 2H, $CH_2$), 3.37 (s, 3H, $OCH_3$), 2.84 (t, 2H, $CH_2$), 1.40 (s, 9H, $C(CH_3)_3$), 1.28 (s, 9H, $C(CH_3)_3$) ppm. $^{13}$C NMR (101 MHz, $CDCl_3$): δ 154.83 (Ar), 140.50 (Ar), 135.94 (Ar), 123.30 (Ar), 123.01 (Ar), 122.05 (Ar), 71.22 ($OCH_3$), 58.96 ($CH_2$), 58.94 ($CH_2$), 53.33 ($CH_2$), 48.08 ($CH_2$), 35.02 ($C(CH_3)_3$), 34.26 ($C(CH_3)_3$), 31.82 ($C(CH_3)_3$), 29.78 ($C(CH_3)_3$) ppm.

$L^7$-a. A round bottom flask equipped with a stirbar was charged with 17-a (0.588 g, 0.954 mmol), ($^i$Pr)$_2$NEt (0.29 mL, 2.099 mmol, 2.2 equiv) and THF (60 mL) was cooled in an ice bath to 0° C. 20 (0.700 g, 2.386 mmol, 2.5 equiv) in THF (35 mL) was added dropwise over 3 minutes to the cooled reaction vessel. The reaction was stirred for 4 h and then concentrated. $L^7$-a was isolated via precipitation from cold EtOAc and extraction of the ammonium salt byproduct with potassium carbonate, water, and DCM. The organic fractions were dried with $MgSO_4$, filtered and concentrated under vacuum to yield 0.19 g of a colorless solid (19% yield). $^1$H NMR (600 MHz, $CDCl_3$): δ 7.22 (d, J=2.5, 2H, ArH), 7.21 (d, J=2.4, 2H, ArH), 7.04 (d, J=2.4, 2H, ArH), 6.90 (d, J=2.3, 2H, ArH), 3.85 (d, J=3.3, 8H, $ArCH_2N$), 3.58 (t, J=5.7, 4H, $CH_2$), 3.34 (s, 6H, $OCH_3$), 2.77 (t, J=5.7, 4H, $CH_2$), 1.99 (s, 12H, $ArCH_3$), 1.41 (s, 18H, $C(CH_3)_3$), 1.33 (s, 18H, $C(CH_3)_3$), 1.29 (s, 18H, $C(CH_3)_3$) ppm. $^{13}$C NMR (151 MHz, $CDCl_3$): δ 164.89 (Ar), 154.17 (Ar), 149.90 (Ar), 142.73 (Ar), 140.51 (Ar), 136.52 (Ar), 135.79 (Ar), 133.72 (Ar), 128.59 (Ar), 127.47 (Ar), 127.32 (Ar), 124.10 (Ar), 123.10 (Ar), 122.01 (Ar), 121.67 (Ar), 110.15 (Ar), 71.07 ($OCH_3$), 58.97 ($CH_2$), 58.50 ($CH_2$), 55.42 ($CH_2$), 51.84 ($CH_2$), 35.03 ($C(CH_3)_3$), 34.28 ($C(CH_3)_3$), 31.87 ($C(CH_3)_3$), 31.82 ($C(CH_3)_3$), 29.74 ($C(CH_3)_3$), 17.91 ($ArCH_3$) ppm.

$L^7$-s. A round bottom flask equipped with a stirbar was charged with 17-s (0.588 g, 0.954 mmol), ($^i$Pr)$_2$NEt (0.29 mL, 2.099 mmol, 2.2 equiv) and THF (60 mL) was cooled in an ice bath to 0° C. 20 (0.700 g, 2.386 mmol, 2.5 equiv) in THF (35 mL) was added dropwise over 3 minutes to the cooled reaction vessel. The reaction was stirred for 4 h and then concentrated. Removal of the ammonium salt byproduct by precipitation from EtOAc left L$^7$-s and some organic impurities in the filtrate. L$^7$-s was isolated in 80% purity as a colorless solid from this filtrate via column chromatography (eluent=9:1 hexanes/EtOAc, r$_f$=0.3) (0.52 g, 52% yield). $^1$H NMR (600 MHz, C$_6$D$_6$): δ 7.50 (d, J=2.4, 2H, ArH), 7.37 (d, J=2.5, 2H, ArH), 7.21 (d, J=2.5, 2H, ArH), 6.98 (d, J=2.4, 2H, ArH), 3.75 (d, J=14.8, 8H, ArCH$_2$N), 3.17 (t, J=5.4, 4H, CH$_2$), 2.91 (s, 6H, OCH$_3$), 2.56 (t, J=5.4, 4H, CH$_2$), 2.24 (s, 12H, ArCH$_3$), 1.69 (s, 18H, C(CH$_3$)$_3$), 1.38 (s, 18H, C(CH$_3$)$_3$), 1.34 (s, 18H, C(CH$_3$)$_3$) ppm.

Example 19

Preparation of Group 10 Metal Complexes (FIG. 10)

NiMe$_2$(tmeda) [Ref 43] and Ni(PMe$_3$)$_2$MeCl [Ref 44, 45] were synthesized according to literature procedures.

Ni$^1$-a-pyridine Synthesis of the anti-dinickelphenoxyiminato complex was achieved by a method similar to that of Mecking, et al.[Ref 46] A solution of L$^1$-a (0.20 g, 0.2484 mmol, 1 equivalent) in 5 mL of diethyl ether and a solution of NiMe$_2$(tmeda) (0.11 g, 0.55 mmol, 2.2 equiv) in 3 mL of diethyl ether were cooled in the glove box freezer to about −35° C. The solution of the ligand was added to the solution of nickel precursor. Pyridine (0.40 mL, 4.97 mmol, 20 equiv) was syringed into the mixture causing a color change to reddish orange. The reaction became gradually cloudier over 5 h of stifling at room temperature, at which point volatiles were removed under vacuum. The orange brown solid was washed over Celite with hexanes and the desired product was collected by flushing it through the Celite with THF. Black precipitate was left on the Celite. The solution of the product was placed under vacuum to remove volatiles leaving 0.21 g (76% yield) of bright orange solid. X-ray quality crystals were grown from a room temperature vapor diffusion of hexanes into THF (FIG. 12). $^1$H NMR (400 MHz, C$_6$D$_6$): δ 8.35 (d, 4H, PyH), 7.72 (s, 2H, ArH), 7.41 (s, 2H, ArH), 7.16 (bs, 6H, N—ArH), 7.14 (s, 2H, ArH), 6.87 (m, 2H, PyH), 6.27 (m, 4H, PyH), 4.32 (septet, J=6.6, 4H, CH(CH$_3$)$_2$), 1.97 (s, 12H, ArCH$_3$), 1.53 (d, J=6.6, 12H, CH(CH$_3$)$_2$), 1.43 (s, 18H, C(CH$_3$)$_3$), 1.13 (d, J=6.6, 12H, CH(CH$_3$)$_2$), −0.69 (s, 6H, NiCH$_3$) ppm. $^{13}$C NMR (shifts determined from gHSQCAD and gHMBC experiments, C$_6$D$_6$): δ 166.0 (ArCHN), 163.5 (Ar), 151.6 (Py), 150.1 (Ar), 140.9 (Ar), 138.6 (Ar), 134.7 (Py), 132.6 (Ar), 131.6 (Ar), 127.0 (Ar), 123.2 (Ar), 122.1 (Py), 118.7 (Ar), 33.4 (ArC(CH$_3$)$_3$), 31.3 (ArC(CH$_3$)$_3$), 28.2 (ArCH(CH$_3$)$_2$), 24.6 (ArCH(CH$_3$)$_2$), 22.8 (ArCH(CH$_3$)$_2$), 18.0 (ArCH$_3$), −7.9 (NiCH$_3$) ppm. Anal. Calcd for C$_{68}$H$_{86}$N$_4$Ni$_2$O$_2$: C, 73.66; H, 7.82; N, 5.05. Found: C, 72.76; H, 7.72; N, 4.96.

Ni$^1$-s-pyridine Metallation of L$^1$-s with NiMe$_2$(tmeda) was accomplished with the same procedure as the metallation of the anti-analog, though due to differences in solubility, the purification method was changed. After the reaction, volatiles were removed under vacuum and the resulting oily solid was dissolved in pentane and filtered over Celite to remove nickel (0). Precipitation from cold pentane yielded 0.20 g (73% yield) of ca. 92% pure desired complex. The remaining impurity was the mono-nickel complex. Subsequent precipitations yielded only minimal increase in purity. Analytically pure Ni$^1$-s-pyridine was obtained by treating the nearly pure complex with half an equivalent of NiMe$_2$(tmeda) and 5 equivalents of pyridine using the same conditions as the initial reaction. Volatiles were removed under vacuum and the resulting oily solid was dissolved in pentane and filtered over Celite to remove nickel (0). Precipitation from cold pentane yielded 0.084 g (30% yield) of pure desired complex. X-ray quality crystals were grown from a cold pentane solution (FIG. 13). $^1$H NMR (400 MHz, C$_6$D$_6$): δ 8.00 (d, 4H, PyH), 7.66 (s, 2H, ArH), 7.54 (m, 2H, PyH), 7.48 (s, 2H, ArH), 7.16 (bs, 6H, N—ArH), 7.10 (s, 2H, ArH), 6.60 (m, 4H, PyH), 4.27 (septet, 4H, CH(CH$_3$)$_2$), 1.98 (s, 12H, ArCH$_3$), 1.53 (d, 12H, CH(CH$_3$)$_2$), 1.33 (s, 18H, C(CH$_3$)$_3$), 1.09 (d, 12H, CH(CH$_3$)$_2$), −0.75 (s, 6H, NiCH$_3$) ppm. $^{13}$C NMR (101 MHz, C$_6$D$_6$): δ 166.62 (ArCHN), 163.71 (Ar), 151.80 (Ar), 150.52 (Ar), 141.23 (Ar), 138.92 (Ar), 136.07 (Ar), 135.76 (Ar), 135.01 (Ar), 134.11 (Ar), 132.31 (Ar), 127.52 (Ar), 126.48 (Ar), 123.69 (Ar), 119.28 (Ar), 33.94 (ArC(CH$_3$)$_3$), 31.66 (ArC(CH$_3$)$_3$), 28.65 (ArCH(CH$_3$)$_2$), 25.05 (ArCH(CH$_3$)$_2$), 23.34 (ArCH(CH$_3$)$_2$), 18.70 (ArCH$_3$), −7.33 (NiCH$_3$) ppm. Anal. Calcd for C$_{68}$H$_{86}$N$_4$Ni$_2$O$_2$: C, 73.66; H, 7.82; N, 5.05. Found: C, 73.44; H, 7.66; N, 5.03.

Deprotonation of L$^1$-a. A scintillation vial equipped with a stir bar was charged with Na(N(SiMe$_3$)$_2$) (0.018 g, 0.099 mmol, 2 equiv) and toluene (1 mL). A solution of L$^1$-a (0.040 g, 0.050 mmol) in toluene (2 mL) was added and the mixture was stirred at room temperature for 2 h, and then concentrated in vacuo to yield a bright yellow solid. The amine side product was removed by two cycles of suspending the product in hexanes and removing the volatiles under vacuum. The solid was used without further purification. $^1$H NMR (400 MHz, CDCl$_3$): δ 8.36 (s, 2H, NCH), 7.38 (d, J=2.5, 2H, ArH), 7.30 (d, J=2.5, 2H, ArH), 7.17 (m, 6H, ArH), 3.05 (hept, J=6.7, 4H, CH(CH$_3$)$_2$), 2.09 (s, 12H ArCH$_3$), 1.34 (s, 18H, C(CH$_3$)$_3$), 1.18 (d, J=6.7, 24H, CH(CH$_3$)$_2$) ppm.

Deprotonation of L$^1$-s. A scintillation vial equipped with a stir bar was charged with KH (0.005 g, 0.117 mmol, 2 equiv) and THF (1 mL) and cooled in the glovebox cold well. A solution of L$^1$-s (0.050 g, 0.059 mmol) in THF (2 mL) was also cooled in the cold well. The solution of L$^1$-s was added and the solution of KH while thawing, and the mixture was stirred at room temperature for 2 h, and then concentrated in vacuo to yield a bright yellow solid. The solid was taken up in Et$_2$O, filtered over celite, concentrated in vacuo, and used without further purification. $^1$H NMR (300 MHz, CDCl$_3$): δ 8.17 (s, 2H, NCH), 7.37 (d, J=3.0, 2H, ArH), 7.30 (s, 2H, ArH), 7.07 (m, 6H, ArH), 3.07 (hept, J=6.7, 4H, CH(CH$_3$)$_2$), 2.06 (s, 12H, ArCH$_3$), 1.32 (s, 18H, C(CH$_3$)$_3$), 1.09 (d, J=6.7, 24H, CH(CH$_3$)$_2$) ppm.

Ni$^1$-a-PMe$_3$. Metallations with Ni(PMe$_3$)$_2$MeCl were carried out using literature conditions.[Ref 47] A solution of deprotonated L$^1$-a (0.114 g, 0.134 mmol, 1 equiv) in Et$_2$O (4 mL) was added dropwise to a solution of Ni(PMe$_3$)$_2$MeCl (0.070 g, 0.266 mmol, 1.98 equiv) in Et$_2$O (3 mL) and the resulting solution was stirred for 14 h, and then concentrated in vacuo to yield a dark orange brown solid. The solid was suspended in hexanes and filtered over Celite. The hexanes washes were discarded and the desired product was flushed thru the Celite with benzene and then concentrated in vacuo to yield 0.12 g of bright orange solid (81% yield). $^1$H NMR (300 MHz, C$_6$D$_6$): δ 8.03 (d, J=8.9, 2H, NCH), 7.39 (d, J=2.7, 2H, ArH), 7.15 (multiple overlapping peaks, 8H, ArH), 3.93 (hept, J=6.8, 4H, CH(CH$_3$)$_2$), 2.16 (s, 12H, ArCH$_3$), 1.39 (s, 18H, C(CH$_3$)$_3$), 1.37 (d, J=6.8, 12H, CH(CH$_3$)$_2$), 1.06 (d, J=6.8, 12H, CH(CH$_3$)$_2$), 0.70 (d, J=9.7, 18H, P(CH$_3$)$_3$), −1.13 (d, J=7.3, 6H, NiCH$_3$) ppm. $^{31}$P NMR (121 MHz, C$_6$D$_6$): 8-8.33 (s) ppm.

Ni$^1$-s-PMe$_3$. A solution of deprotonated L$^1$-s (0.151 g, 0.171 mmol, 1 equiv) in Et$_2$O (5 mL) was added dropwise to a solution of Ni(PMe$_3$)$_2$MeCl (0.089 g, 0.340 mmol, 1.98 equiv) in Et$_2$O (4 mL) and the resulting solution was stirred for 14 h, filtered over Celite, and then concentrated in vacuo to yield a red orange solid. The $^1$H and $^{31}$P NMR spectra still indicated the presence of Ni(PMe$_3$)$_2$MeCl so an additional 0.15 equiv of deprotonated L$^1$-s was added to the red orange solid in Et$_2$O (9 mL) and the reaction was stirred an additional 14 h. 0.16 g of red orange solid was collected (84% yield). $^1$H NMR (400 MHz, C$_6$D$_6$): δ 8.05 (s, 2H, NCH), 7.35 (d, J=2.7, 2H, ArH), 7.17 (bs, 6H, ArH), 7.11 (d, J=2.7, 2H, ArH), 3.95 (hept, J=6.9, 4H, CH(CH$_3$)$_2$), 2.25 (s, 12H, ArCH$_3$), 1.35 (d, J=6.9, 12H, CH(CH$_3$)$_2$), 1.25 (s, 18H, C(CH$_3$)$_3$), 1.04 (d, J=6.9, 12H, CH(CH$_3$)$_2$), 0.80 (d, J=9.5, 18H, P(CH$_3$)$_3$), −1.05 (s, 6H, NiCH$_3$) ppm. $^{31}$P NMR (162 MHz, C$_6$D$_6$): 8-8.15 (s) ppm.

Ni$^3$-a-PMe$_3$. Deprotonated with L$^3$-a with KH using the same procedure as was used to deprotonate L$^1$-s. The deprotonated material was then metallated with Ni(PMe$_3$)$_2$MeCl using the same procedure as for Ni$^1$-a-PMe$_3$. Ni$^3$-a-PMe$_3$ was purified by precipitation from pentane. $^1$H NMR (300 MHz, C$_6$D$_6$): δ 7.99 (s, 2H, NCH), 7.34 (d, J=2.7, 2H, ArH), 7.14 (bs, 6H, ArH), 7.10 (d, J=2.7, 2H, ArH), 7.03 (s, 1H, ArH), 3.90 (hept, J=6.8, 4H, CH(CH$_3$)$_2$), 2.26 (s, 6H, ArCH$_3$), 2.14 (s, 3H, ArCH$_3$), 1.37 (2d, 12H, CH(CH$_3$)$_2$), 1.34 (s, 18H, C(CH$_3$)$_3$), 1.03 (2d, 12H, CH(CH$_3$)$_2$), 0.76 (d, J=9.5, 18H, P(CH$_3$)$_3$), −1.14 (s, 6H, NiCH$_3$) ppm.

Ni$^3$-s-PMe$_3$. Deprotonated with L$^3$-s with KH using the same procedure as was used to deprotonate L$^1$-s. The deprotonated material was then metallated with Ni(PMe$_3$)$_2$MeCl using the same procedure as for Ni$^1$-s-PMe$_3$. Ni$^3$-s-PMe$_3$ was purified by precipitation from pentane. $^1$H NMR (300 MHz, C$_6$D$_6$): δ 8.01 (d, J=8.2, 2H, NCH), 7.42 (d, J=2.9, 2H, ArH), 7.16 (m, 6H, ArH), 7.07 (d, J=2.9, 2H, ArH), 7.02 (s, 1H, ArH), 3.97 (hept, J=6.8, 4H, CH(CH$_3$)$_2$), 2.35 (s, 6H, ArCH$_3$), 2.25 (s, 3H, ArCH$_3$), 1.41 (dd, J=9.7, 6.7, 12H, CH(CH$_3$)$_2$), 1.22 (s, 18H, C(CH$_3$)$_3$), 1.05 (dd, J=15.7, 6.7, 12H, CH(CH$_3$)$_2$), 0.92 (d, J=9.6, 18H, P(CH$_3$)$_3$), −1.06 (d, J=6.4, 6H, NiCH$_3$) ppm.

Example 20

Figure 11:
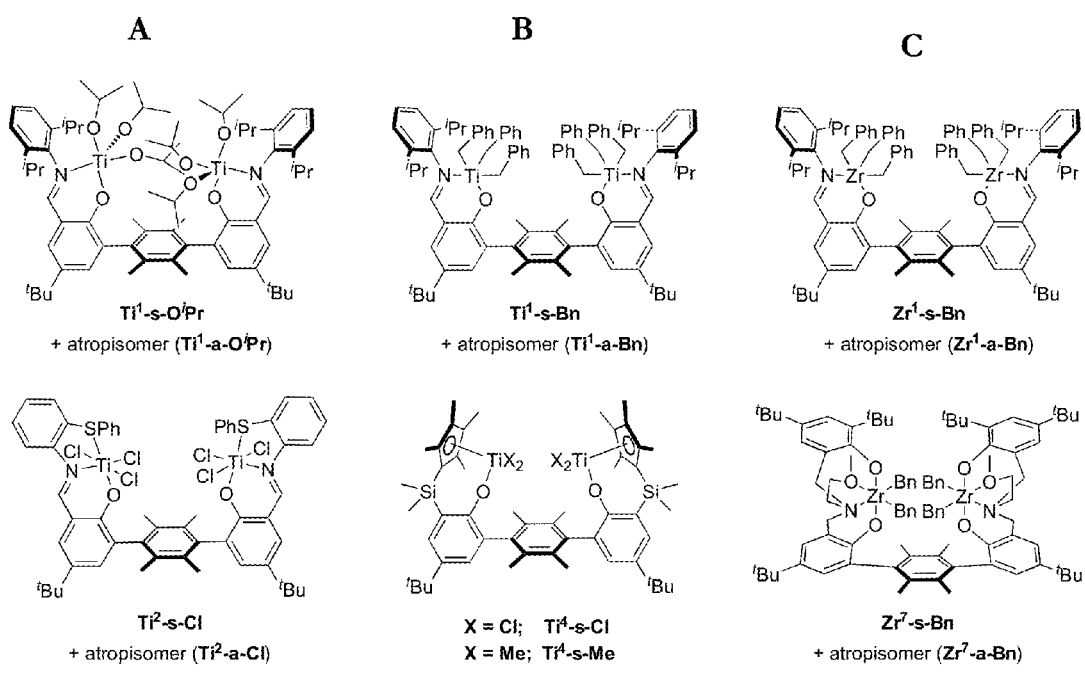
FIG. 11 shows the structures of multi-metallic polymerization precatalysts according to embodiments herein described, and in particular multi-metallic organometallic complexes with group 4 metals. Panel A shows the structure of the syn atropisomer of multi-metallic organometallic complexes $Ti^1$-s-$O^iPr$. Panel B shows the structure of the syn atropisomer of multi-metallic organometallic complexes $Ti^1$-s-Bn. Panel C shows the structure of the syn atropisomer of multi-metallic organometallic complexes $Zr^1$-s-Bn. Panel D shows the structure of the syn atropisomer of multi-metallic organometallic complexes $Ti^2$-s-Cl. Panel E shows the structure of the syn atropisomer of multi-metallic organometallic complexes $Ti^4$-s-Cl (X=Cl) and $Ti^4$-s-Me (X=Me). Panel F shows the structure of the syn atropisomer of multi-metallic organometallic complexes $Zr^7$-s-Bn.

Preparation of Group 4 Metal Complexes (FIG. 11)

TiBn$_4$,[Ref 48] ZrBn$_4$,[Ref 49] TiCl$_4$(THF)$_{2,[Ref 50]}$ and Me$_2$Mg(tmeda)[Ref 51] were synthesized according to literature procedures.

Ti$^1$-a-O$^i$Pr. A solution of L$^1$-a (0.050 g, 0.062 mmol) in THF (3 mL) was added dropwise to a solution of Ti(O$^i$Pr)$_4$ (0.039 g, 0.137 mmol, 2.2 equiv) in THF (2 mL) and the resulting solution was stirred for 20 h, and concentrated in vacuo. The material was then dissolved in hexanes and filtered over celite. The volatiles were removed under vacuum to yield Ti$^1$-a-O$^i$Pr as a yellow solid. X-ray quality single crystals were grown by evaporation of hexanes at −35° C. (FIG. 14). $^1$H NMR (300 MHz, C$_6$D$_6$): δ 8.25 (s, 2H, NCH), 7.61 (d, J=2.6, 2H, ArH), 7.25 (d, J=2.6, 2H, ArH), 7.16 (bs, 6H, ArH), 4.58 (hept, J=6.1, 6H, OCH(CH$_3$)$_2$), 3.47 (hept, J=6.8, 4H, CH(CH$_3$)$_2$), 2.26 (s, 12H, ArCH$_3$), 1.28 (s, 18H, C(CH$_3$)$_3$), 1.10 (d, J=6.1, 60H, OCH(CH$_3$)$_2$ and CH(CH$_3$)$_2$) ppm.

Ti$^1$-s-O$^i$Pr. A solution of L$^1$-s (0.092 g, 0.115 mmol) in THF (5 mL) was added dropwise to a solution of Ti(O$^i$Pr)$_4$ (0.072 g, 0.252 mmol, 2.2 equiv) in THF (4 mL) and the resulting solution was stirred for 22 h, and concentrated in vacuo. The material was then dissolved in hexanes and filtered over celite. The volatiles were removed under vacuum to yield a yellow solid. This solid was reprecipitated from hexanes to yield Ti$^1$-s-O$^i$Pr. X-ray quality single crystals were grown by evaporation of hexanes at −35° C. (FIG. 14). $^1$H NMR (300 MHz, C$_6$D$_6$): δ 8.27 (s, 2H, NCH), 7.56 (d, J=2.7, 2H, ArH), 7.29 (d, J=2.7, 2H, ArH), 7.19 (bs, 6H, ArH), 4.76 (hept, J=6.0, 6H, OCH(CH$_3$)$_2$), 3.59 (hept, J=6.7, 4H, CH(CH$_3$)$_2$), 2.40 (s, 12H, ArCH$_3$), 1.24 (s, 18H, C(CH$_3$)$_3$), 1.15 (d, 60H, OCH(CH$_3$)$_2$ and CH(CH$_3$)$_2$) ppm.

Ti$^1$-a-Bn and Ti$^1$-s-Bn. A cooled solution of L$^1$ (0.050 g, 0.062 mmol) in toluene (3 mL) was added dropwise to a solution of TiBn$_4$ (0.064 g, 0.155 mmol, 2.5 equiv) in toluene (2 mL) at −35° C. and the resulting solution was stirred for 20 h covered, and concentrated in vacuo to yield a deep red solid. Ti$^1$-a-Bn was purified by washing the solid with hexanes, Et$_2$O, and THF. The remaining deep red material was 90% pure by $^1$H NMR spectroscopy. Ti$^1$-s-Bn was purified by reprecipitation of the solid from hexanes to yield a single major species in 80% purity by $^1$H NMR spectroscopy. Ti$^1$-a-Bn $^1$H NMR (400 MHz, CDCl$_3$): δ 8.56 (s, 2H, NCH), 7.63 (d, J=2.5, 2H, ArH), 7.38 (d, J=2.5, 2H, ArH), 7.19 (m, 6H, ArH), 6.94 (m, 12H, CH$_2$ArH), 6.84 (m, 6H, CH$_2$ArH), 6.41 (m, 12H, CH$_2$ArH), 2.60 (s, 12H, CH$_2$Ar), 2.34 (hept, 4H, CH(CH$_3$)$_2$), 2.13 (s, 12H, ArCH$_3$), 1.31 (s, 18H, C(CH$_3$)$_3$), 1.18 (bs, 12H, CH(CH$_3$)$_2$), 1.03 (bs, 12H, CH(CH$_3$)$_2$) ppm. Ti$^1$-s-Bn $^1$H NMR (400 MHz, C$_6$D$_6$): δ 8.33 (s, 2H, NCH), 7.54 (d, J=2.5, 2H, ArH), 7.24 (d, J=2.5, 2H, ArH), 7.09 (m, 6H, ArH), 7.01 (m, 12H, CH$_2$ArH), 6.84 (m, 6H, CH$_2$ArH), 6.74 (m, 12H, CH$_2$ArH), 2.99 (s, 12H, CH$_2$Ar), 2.41 (hept, 4H, CH(CH$_3$)$_2$), 2.37 (s, 12H, ArCH$_3$), 1.21 (s, 18H, C(CH$_3$)$_3$), 1.07 (bs, 12H, CH(CH$_3$)$_2$), 1.00 (bs, 12H, CH(CH$_3$)$_2$) ppm.

Zr$^1$-a-Bn and Zr$^1$-s-Bn. A cooled solution of L$^1$ (0.050 g, 0.062 mmol) in toluene (3 mL) was added dropwise to a solution of ZrBn$_4$ (0.071 g, 0.155 mmol, 2.5 equiv) in toluene (2 mL) at −35° C. and the resulting solution was stirred for 20 h, and concentrated in vacuo to yield a bright orange solid. To purify Zr$^1$-a-Bn, the solid was washed over Celite with benzene and the product was flushed thru with dichloromethane. Then volatiles were removed in vacuo. The resulting bright orange solid was clean by $^1$H NMR spectroscopy. To purify Zr$^1$-s-Bn, the solid was washed over Celite with hexanes and the product was flushed thru with benzene. Then volatiles were removed in vacuo. The residue was suspended in hexanes and cooled to −35° C. overnight. Bright orange solid was collected via filtration. Zr$^1$-a-Bn $^1$H NMR (400 MHz, CDCl$_3$): δ 8.41 (s, 2H, NCH), 7.56 (d, J=2.5, 2H, ArH), 7.31 (d, J=2.5, 2H, ArH), 7.18 (m, 6H, ArH), 6.86 (m, 18H, CH$_2$ArH), 6.27 (m, 12H, CH$_2$ArH), 2.51 (hept, J=6.6, 4H, CH(CH$_3$)$_2$), 2.36 (s, 12H, CH$_2$Ar), 2.09 (s, 12H, ArCH$_3$), 1.29 (s, 18H, C(CH$_3$)$_3$), 1.22 (d, J=6.6, 12H, CH(CH$_3$)$_2$), 1.04 (d, J=6.6, 12H CH(CH$_3$)$_2$) ppm. Zr$^1$-s-Bn $^1$H NMR (400 MHz, C$_6$D$_6$): δ 8.25 (s, 2H, NCH), 7.49 (d, J=2.6, 2H, ArH), 7.22 (d, J=2.6, 2H, ArH), 7.09 (m, 6H, ArH), 6.87 (m, 18H, CH$_2$ArH), 6.62 (m, 12H, CH$_2$ArH), 2.57 (hept, J=6.7, 4H, CH(CH$_3$)$_2$), 2.33 (s, 12H, CH$_2$Ar), 1.93 (s, 12H, ArCH$_3$), 1.18 (s, 18H, C(CH$_3$)$_3$), 1.17 (d, J=6.7, 12H, CH(CH$_3$)$_2$), 1.02 (d, J=6.7, 12H CH(CH$_3$)$_2$) ppm.

Deprotonation of L$^2$-a and L$^2$-s. A scintillation vial equipped with a stir bar was charged with KH (0.006 g, 0.159 mmol, 2 equiv) and THF (1 mL) and cooled in the glovebox cold well. A solution of L$^3$ (0.068 g, 0.079 mmol) in THF (2 mL) was also cooled in the cold well. The solution of L$^2$ was added and the solution of KH while thawing, and the mixture was stirred at room temperature for 2 h during which time the reaction with the anti atropisomer stayed cloudy while the reaction with the syn atropisomer turned clear, and then concentrated in vacuo to yield a bright yellow solid for the anti atropisomer and a bright orange solid for the syn atropisomer. $^1$H NMR spectroscopy indicated that the anti atropisomer was not fully deprotonated as evidenced by a phenol peak in the spectrum so the solid was resubmitted to the reaction conditions with another equivalent of KH. After an hour of stirring the reaction mixture turned clear. The resubmitted reaction was stirred for a total of 14 h and then concentrated in vacuo to yield a bright yellow solid. Deprotonated $L^2$-a $^1$H NMR (300 MHz, $C_6D_6$): δ 8.09 (s, 2H, NCH), 7.20 (bs, 2H, ArH), 7.04 (m, 6H, ArH), 6.91 (m, 4H, ArH), 6.82 (m, 6H, ArH), 6.71 (m, 2H, ArH), 6.63 (m, 2H, ArH), 2.50 (s, 6H, ArCH$_3$), 1.89 (s, 6H, ArCH$_3$), 1.36 (m, 18H, C(CH$_3$)$_3$) ppm. Deprotonated $L^2$-a $^1$H NMR (300 MHz, $C_6D_6$): δ 8.04 (s, 2H, NCH), 7.40 (bs, 2H, ArH), 7.19 (m, 8H, ArH), 6.92 (m, 6H, ArH), 6.82 (m, 2H, ArH), 6.68 (m, 2H, ArH), 6.35 (m, 2H, ArH), 1.99 (s, 12H, ArCH$_3$), 1.42 (m, 18H, C(CH$_3$)$_3$) ppm.

$Ti^2$-a-Cl and $Ti^2$-s-Cl. After the deprotonation of $L^3$ with KH, the solid was metallated without further purification and assuming quantitative yield of the deprotonated product. Deprotonated $L^2$ (0.079 mmol) in toluene (5 mL) was added dropwise to TiCl$_4$(THF)$_2$ (0.058 g, 0.174 mmol, 2.2 equiv) in toluene (5 mL) and left stirring at room temperature for 12 h. The reaction was then concentrated in vacuo to yield a deep red solid. $Ti^2$-a-Cl was purified by precipitation from DCM by the addition of hexanes and cooling to −35° C. The red solid was collected via filtration over a frit. $Ti^2$-s-Cl was partially purified (to 90% purity) by washing over Celite with hexanes and benzene before flushing the desired product through with DCM. The product is partially soluble in benzene, so some material is lost in this method of purification. Other precipitations and recrystallizations also proved ineffective for further purification of $Ti^2$-s-Cl. $Ti^2$-a-Cl $^1$H NMR (400 MHz, CDCl$_3$): δ 8.96 (s, 2H, NCH), 7.68 (m, 10H, ArH), 7.50 (m, 2H, ArH), 7.31 (m, 10H, ArH), 2.00 (s, 12H, ArCH$_3$), 1.38 (s, 18H, C(CH$_3$)$_3$) ppm. $Ti^2$-s-Cl $^1$H NMR (300 MHz, CDCl$_3$): δ 8.91 (s, 2H, NCH), 7.64 (m, 8H, ArH), 7.54 (m, 2H, ArH), 7.46 (m, 2H, ArH), 7.29 (m, 10H, ArH), 2.09 (s, 12H, ArCH$_3$), 1.37 (s, 18H, C(CH$_3$)$_3$) ppm.

$Ti^4$-s-Cl. Metalation of $L^4$-s was accomplished by dissolving $L^4$-s (0.200 g, 0.23 mmol, 1 equiv) in 10 mL of Et$_2$O and cooling to −35° C. at which time, $^a$BuLi (0.380 mL, 0.95 mmol, 4.1 equiv) was added by syringe. The mixture was allowed to warm to ambient temperature and stirred for 3 h. Volatiles were removed in vacuo. The remaining material was dissolved in THF (20 mL). This solution was added cold (−35° C.) to a solution of TiCl$_4$(THF)$_2$ (0.154 g, 0.46 mmol, 2.0 equiv) in THF (20 mL) at −35° C. The mixture was allowed to reach ambient temperature and then was heated in a 95° C. oil bath for 4 h. Volatiles were removed in vacuo. The material was taken up in pentane (20 mL) and filtered through Celite to remove lithium salts. The material was isolated by crystallization from pentane/hexamethyldisiloxane (0.015 g, 6.4% yield). Yellow, X-ray quality crystals of $Ti^4$-s-Cl were obtained by vapor-diffusion of pentane out of hexamethyldisiloxane (FIG. 15). $^1$H-NMR (300 MHz, $C_6D_6$): δ 7.63 (d, 2H, J=2.5 Hz, Ar—H) 7.37 (d, 2H, J=2.4 Hz, Ar—H) 2.28 (s, 12H, Ar—CH$_3$) 1.98 (s, 12H, Cp*—CH$_3$) 1.95 (s, 12H, Cp*—CH$_3$) 1.31 (s, 18H, C(CH$_3$)$_3$) 0.53 (s, 12H, Si—CH$_3$) ppm.

$Ti^4$-s-Me. The titanium dichloride complex $Ti^4$-s-Cl (0.0084 g, 0.008 mmol) was dissolved in 5 mL of diethyl ether and cooled to −35° C. A solution of Me$_2$Mg(tmeda) (2.72 mg, 0.016 mmol) was prepared by dissolving the material in 5 mL of Et$_2$O and cooling to −35° C. The solution containing the titanium complex was added to the solution of Me$_2$Mg (tmeda) and warmed to room temperature. The mixture was stirred for 1 h before removing volatiles in vacuo. The material was taken up in pentane and filtered through Celite to remove magnesium salts. The product was isolated as colorless oil (8 mg, 90%). $^1$H NMR (300 MHz, $C_6D_6$) δ 7.64 (s, 2H, ArH) 7.44 (s, 2H, ArH) 2.34 (s, 12H, ArCH$_3$) 1.88 (s, 12H, Cp*Me) 1.74 (s, 12H, Cp*Me) 1.37 (s, 18H, C(CH$_3$)$_3$) 0.59 (s, 12H, TiCH$_3$) 0.51 (s, 12H, SiCH$_3$) ppm.

$Zr^7$-a-Bn and $Zr^7$-s-Bn. A solution of $L^7$ (0.044 g, 0.042 mmol) in toluene (2 mL) and a solution of ZrBn$_4$ (0.038 g, 0.084 mmol, 2 equiv) in toluene (1 mL) were frozen in the cold well in the glovebox. The solution of $L^7$ was added dropwise to the ZrBn$_4$ while thawing in the dark and the resulting solution was stirred for 5 h, filtered over Celite, and concentrated in vacuo to yield a pale yellow solid. $Zr^7$-s-Bn was partially purified by precipitation from cold hexanes. $Zr^7$-a-Bn $^1$H NMR (300 MHz, $C_6D_6$): δ 7.61 (m, 4H), 7.32 (m, 4H), 7.01 (m, 20H), 3.62 (m, 2H), 3.28 (m, 2H), 2.75 (s, 6H), 2.69 (m, 4H), 2.58 (s, 4H), 2.47 (m, 2H), 2.42 (d, 6H), 2.22 (d, 2H), 2.11 (s, 4H), 1.97 (d, 4H), 1.84 (s, 18H), 1.38 (s, 18H), 1.31 (s, 18H), 1.12 (m, 6H) ppm. $Zr^7$-s-Bn $^1$H NMR (300 MHz, $C_6D_6$): δ 7.54 (d, J=2.5, 2H), 7.48 (d, J=2.5, 2H), 7.21 (d, J=7.1, 8H), 7.09 (d, J=2.4, 2H), 6.88 (m, 12H), 6.62 (t, J=7.1, 2H), 3.60 (m, 4H), 2.76 (s, 6H), 2.67 (d, 2H), 2.61 (s, 6H), 2.50 (s, 6H), 2.42 (s, 6H), 2.31 (m, 4H), 2.18 (m, 4H), 1.97 (m, 4H), 1.61 (s, 18H), 1.40 (s, 18H), 1.36 (s, 18H) ppm.

Example 21

Ethylene Homopolymerization

A 3 oz. Andrews glass pressure reaction vessel equipped with Swagelock valves and a gauge was used for all high pressure polymerizations. The high-pressure setup was brought into the glove box with a magnetic stirbar and charged with the desired amount of solvent. A syringe was loaded with a solution of the desired organometallic precatalyst and activator or scavenger, if applicable, and the needle was sealed with a rubber septum. The syringe and setup were brought out of the box and the setup was clamped firmly over a hot plate with a mineral oil bath previously regulated to the desired temperature (generally 25° C.). The solution was stirred vigorously (1200 rpm). A nylon core hose equipped with quick connect adaptors was purged with ethylene for 1 minute and the pressure was set to 15 psig. The hose was connected to the setup and the setup was filled with ethylene. A bleed needle was inserted into a Teflon septum at the top of the high pressure setup and flushed with ethylene. The solution of organometallic precatalyst and any applicable activator or scavenger was added via syringe and the top of the setup was closed. The pressure was increased to the desired level. After the desired time, the ethylene hose was disconnected, the setup was vented and the reaction mixture was quenched with acidified methanol (3 times the reaction volume) to precipitate the polymer, which was collected as a white solid by filtration over a fine frit. If only a small amount of polymer was precipitated, the entire mixture was collected and volatile materials were removed under vacuum. All polymers were dried on the Schlenk line for a minimum of 8 hours before a mass was recorded.

Example 22

Ethylene Homopolymerization in the Presence of Polar Additives

Homopolymerizations of ethylene with polar additives were completed via the same methods as the homopolymerization of ethylene except that the desired amount of additive was added to the solvent in the high pressure setup before sealing and removing from the glovebox.

Example 23

Polymerization Procedure for the Copolymerization of Ethylene and Alpha-Olefins Copolymerizations of ethylene and alpha-olefins were completed via the same methods as the homopolymerization of ethylene except that the desired amount of comonomer was added to the solvent in the high pressure setup before sealing and removing from the glovebox.

Example 24

Polymerization Procedure for the Copolymerization of Ethylene and Polar Olefins Copolymerizations of ethylene and polar olefins were completed via the same methods as the homopolymerization of ethylene except that the desired amount of comonomer was added to the solvent in the high pressure setup before sealing and removing from the glovebox.

Example 25

Polymerization Procedures for 1-hexene Homo- and Copolymerizations (Not with Ethylene)

For homopolymerizations of 1-hexene with nickel complexes, the nickel complex, Ni(COD)$_2$, if applicable, and solvent were added to a Schlenk tube equipped with a stirbar in the glovebox. The 1-hexene was added last and the timer for the polymerization was started upon addition of 1-hexene. The Schlenk tube was sealed, brought out of the glovebox, and clamped over a stirplate with mineral oil bath set to 25° C. After the desired time, the Schlenk flask was opened to air and the reaction mixture was quenched with acidified methanol. Poly-1-hexene was extracted with hexanes, volatiles were removed on the rotary evaporator and the sticky residue was dried under vacuum on the Schlenk line for more than 12 hours.

For homopolymerizations of 1-hexene with zirconium complexes, the zirconium complex, half of the solvent, if applicable, and half of the 1-hexene were added to a Schlenk tube equipped with a stirbar in the glovebox. Trityl borate suspended/dissolved in the remainder of the solvent and 1-hexene was added dropwise and the timer for the polymerization was started upon addition. The Schlenk tube was sealed, brought out of the glovebox and clamped over a stirplate. After the desired time, the Schlenk flask was opened to air and the reaction mixture was transferred to a tared round bottom flask with hexanes, volatiles were removed on the rotary evaporator and the sticky residue was dried under vacuum on the Schlenk line for more than 12 hours.

Example 26

Synthesis of Mononucleating Salicylaldimine Ligands Based on Biphenyl and Terphenyl Frameworks [Ref 52]

For comparison with the dinuclear systems, mononucleating ligands were also prepared. Several aspects of the terphenyl framework were investigated. The steric effect close to the metal center was tested by targeting catalysts based on a salicylaldimine substituted with pentamethylphenyl ortho to the oxygen (13). A previously reported variant (29)[Ref 53] of this ligand includes a phenyl group instead of pentamethylphenyl and was studied as a more sterically open version of 13. Dinucleating ligand precursors 7-s and 7-a bear steric bulk on both peripheral rings of the terphenyl unit. Three mononucleating terphenyl ligands were prepared to mimic the remote steric environment of 7-s and 7-a. All are fully substituted on the central ring. Two have oxygen substitution on both peripheral aryls in the position ortho to the central ring. This substitution pattern blocks the aryl-aryl rotation and leads to syn and anti isomers (19-s and 19-a, respectively). The third mononucleating terphenyl ligand (24) has 3,5-di-tert-butyl substitution on the second peripheral ring.

Figure 21:
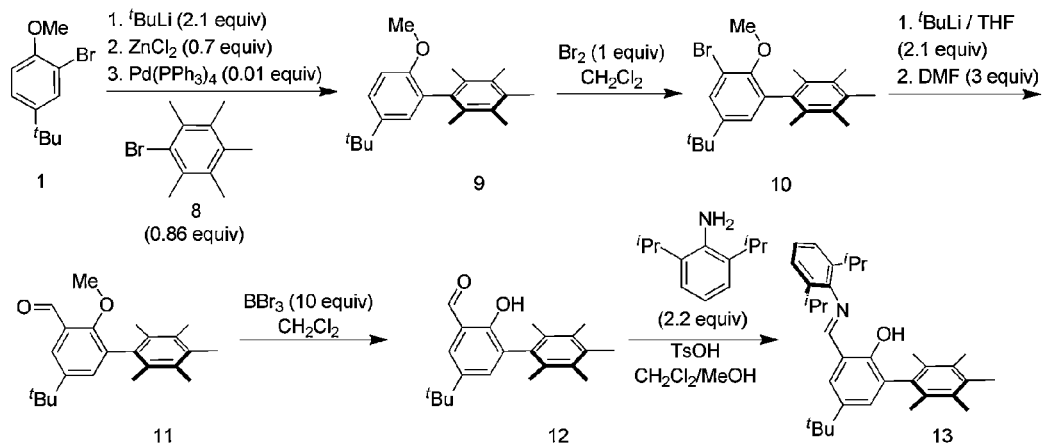
FIG. 21 shows a schematic illustration of an exemplary reaction scheme for the preparation of mononucleating biphenyl-based salicylaldimine ligands for comparison to the multinucleating ligands according to embodiments herein described.

The synthesis of salicylaldimine 13 was accomplished in five steps (FIG. 21). Negishi cross-coupling of 1 and pentamethylbromobenzene[Ref 54] afforded biphenyl species 9. Subsequent steps are similar to the synthesis of ligands 7-s and 7-a. Bromination, followed by lithium-halogen exchange and DMF treatment installed the formyl moiety to give 11. Deprotection of the ether group and condensation with 2,6-diisopropyl aniline provided 13 in 14% overall yield.

Figure 20:
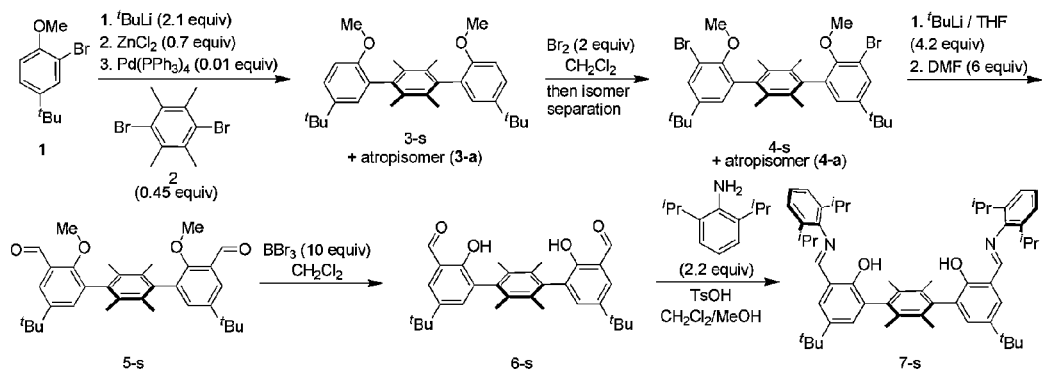
FIG. 20 shows a schematic illustration of an exemplary reaction scheme for the preparation of atropisomers of a p-terphenyl bisphenoxyimine ligands according to an embodiment herein described.
Figure 22:
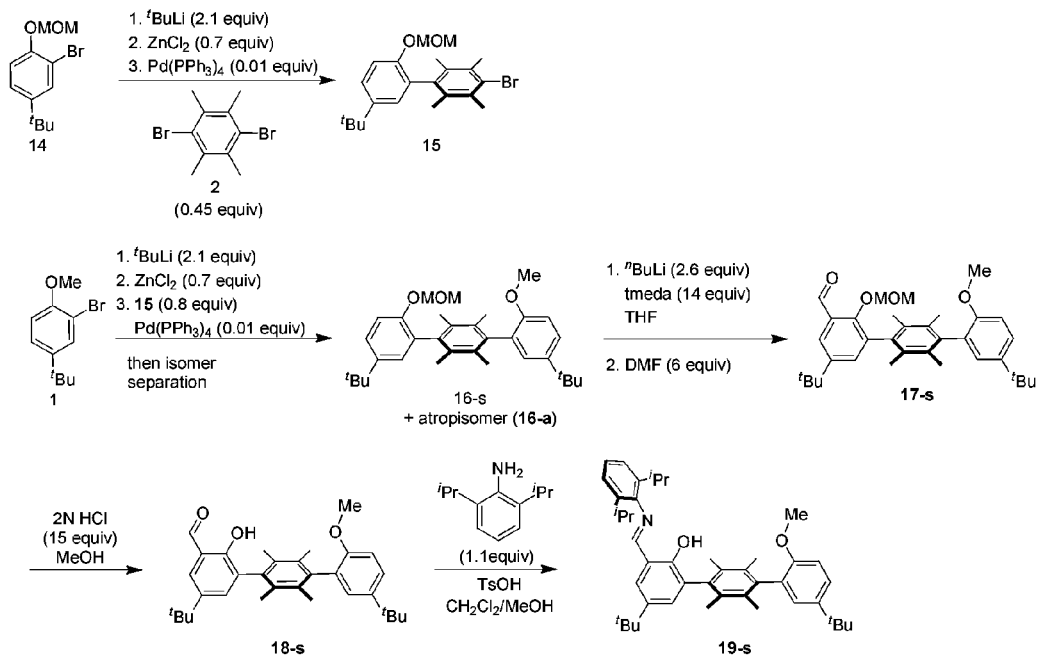
FIG. 22 shows a schematic illustration of an exemplary reaction scheme for the preparation of mononucleating terphenyl-based salicylaldimine ligands for comparison to the multinucleating ligands according to embodiments herein described.
Figure 23:
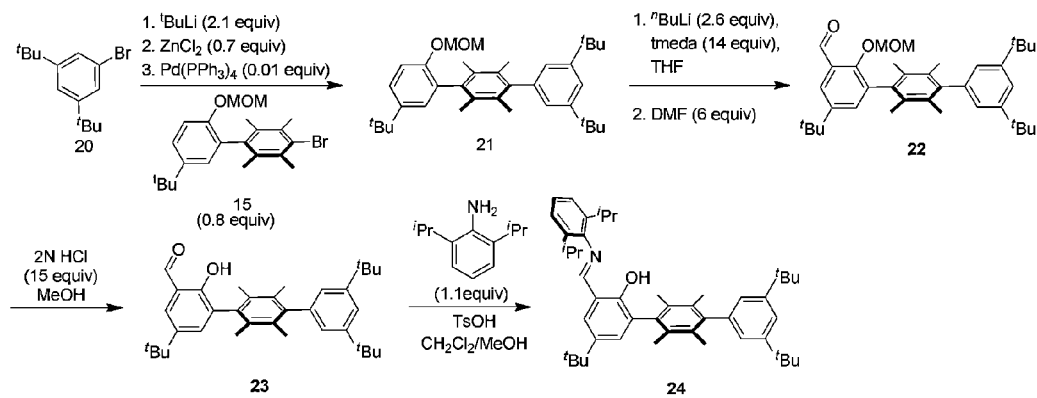
FIG. 23 shows a schematic illustration of an exemplary reaction scheme for the preparation of mononucleating terphenyl-based salicylaldimine ligands without methoxy substitution for comparison to the multinucleating ligands according to embodiments herein described.

The synthesis of the mononucleating terphenyl ligand analogs was accomplished via a modification of the procedure in FIG. 20. Negishi cross-coupling of 2 with 2.2 equivalents of zinc reagent stemming from methoxymethyl (MOM)-protected 2-bromo-4-tert-butylphenol afforded both the expected terphenyl species as well as a bromo-substituted biphenyl species 15 (FIG. 22). The isolation of the mono-cross-coupled product (15) was instrumental to the preparation of asymmetric terphenyl ligands. A second cross-coupling, with orthogonally protected 2-bromo-4-tert-butylanisole (1), afforded the syn and anti atropisomers of terphenyl species 16 in a ratio of 1:1. Deprotonation directed by the MOM-protected ether using n-butyllithium and N,N,N',N'-tetramethylethylenediamine (tmeda) led, upon reaction with DMF and aqueous workup, to the installation of a single formyl group. Acid-catalyzed removal of the MOM group followed by condensation with 2,6-diisopropylaniline afforded 19-a and 19-s in 35 and 37% yield, respectively, starting from compounds 16. Separation of the two atropisomers was accomplished by column chromatography after the second Negishi cross-coupling (compounds 16). The third mononucleating terphenyl ligand was synthesized starting from the Negishi cross-coupling of 15 with the aryl-zinc reagent derived from 3,5-di-tert-butylbromobenzene to yield asymmetric terphenyl 21 (FIG. 23). Adapting the protocols from the synthesis of 19, 21 was converted to monophenol 24 in 34% overall yield from 15. A single isomer is expected because of the lack of substitution ortho to the central ring and due to the symmetrical substitution pattern on the peripheral aryl.

Example 27

Studies of the Interconversion of Atropisomers [Ref 52]

Figure 24:
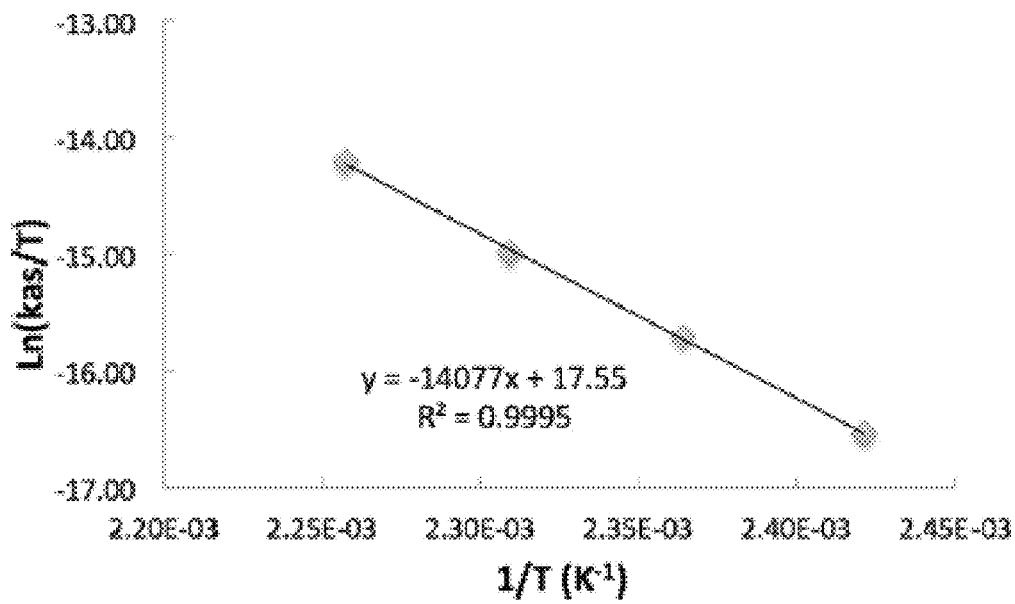
FIG. 24 shows an Eyring plot for the isomerization of atropisomers of multinucleating ligands according to embodiments herein described. In particular, the Eyring plot for the isomerization of 7-a to 7-s is shown.

In the context of preserving the steric environment and the metal-metal separation in complexes supported by ligands with restricted rotation around aryl-aryl bonds, it is of interest to determine the kinetic and thermodynamic behavior of the atropisomers. Because the nickel complexes decompose before isomer interconversion (vide infra), kinetics studies of the interconversion of ligand precursor 7-a to 7-s were performed in [D$_0$]-1-bromonaphthalene at 140, 150, 160 and 170° C. and were monitored by $^1$H NMR spectroscopy. Starting from either 7-s or 7-a, equilibrium was reached over 20 h at 140° C., 8 h at 150° C., 3.5 h at 160° C., and 1.75 h at 170° C. At these temperatures, the equilibrium constant is $K_{eq}$=[7- s]/[7-a]=0.61 (eq 1). The studied processes fit the integrated rate expression for approach to equilibrium of first-order kinetics (eq 2; $X_e$=concentration at equilibrium; X=concentration at time t).[Ref 55] An Eyring plot using the determined rate constants provided activation energy parameters: $\Delta H^\ddagger$=28.0±0.4 kcal×mol$^{-1}$ and $\Delta S^\ddagger$=−12.3±0.4 cal× mol$^{-1}$×K$^{-1}$ (FIG. 24). As expected, the calculated free energy barrier to rotation for 7-a ($\Delta G^*$=32 kcal×mol$^{-1}$ at 298 K) is significantly higher than for a recently reported terphenyl system without permethylation of the central arene (14.6 kcal×mol$^{-1}$).[Ref 56] Although the entropy of activation for conformational dynamic processes is typically close to zero, the larger absolute value determined here is still in the range reported for related fluxional processes, for example rotation around the C—NMe$_2$ bond of a N,N-dimethylthiourethane ($\Delta S^\ddagger$=−8±2 cal×mol$^{-1}$×K$^{-1}$).[Ref 57] The significantly negative value suggests a relatively ordered transition state likely corresponding to the geometry with two aryl rings coplanar. This geometry can require significant distortions of the ring substituents. The barrier for isomerization for 7-a is comparable to the reported value for the restricted rotation in hexaarylbenzenes (ca. 33 kcal×mol$^{-1}$ at 419 K).[Ref 58] Extrapolating to 25° C. (the temperature at which most of the polymerizations discussed herein were run), the rate constant for the interconversion of 7-a and 7-s is approximately 10$^{-11}$ s$^{-1}$ indicating that virtually no isomerization takes place over the course of the polymerization experiment.

(1)

$$\ln(X_e - X) = -(k_{as} + k_{sa}) \cdot t \qquad (2)$$

Example 28

Synthesis of Nickel Complexes [Ref 52]

Figure 25:
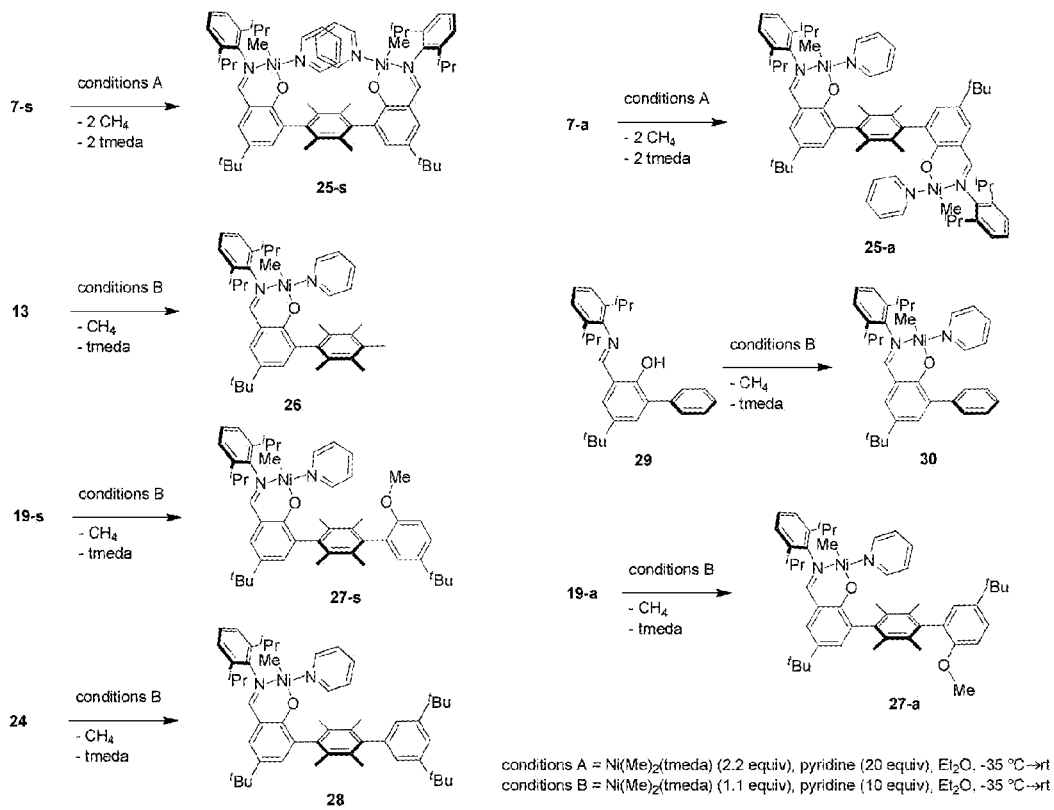
FIG. 25 shows a schematic illustration of reaction schemes for the preparation of multi-metallic polymerization catalysts according to embodiments herein described and of monometallic nickel complexes for comparison to the multi-metallic polymerization catalysts herein described.

Nickel complexes were prepared via alkane elimination. Reaction of phenols with a 10% excess of NiMe$_2$(tmeda) in diethyl ether in the presence of excess pyridine allowed for the isolation of the nickel-methyl species supported by the corresponding phenoxyiminato ligands with a bound pyridine (FIG. 25). If acetonitrile or tertiary amine (N,N-dimethylbutylamine or N,N-dimethylethylamine) were utilized instead of pyridine or if no additional labile ligand was added, the desired nickel complexes were not isolated cleanly. The $^1$H NMR spectra of the isolated nickel complexes each display a single peak around −0.5 ppm, diagnostic of the N$_1$—CH$_3$ moiety. The atropisomers were assigned by $^1$H-$^1$H NOESY and ROESY NMR studies. Through-space cross peaks are observed between the meta proton of the Ni-bound pyridine and the proton ortho to the aryl-aryl linkage for only one of the isomers. This isomer was assigned as the anti atropisomer (25-a and 27-a).

NMR spectra of the nickel complexes are each indicative of a single ligand environment, suggesting that for complexes with atropisomers no isomerization occurs during synthesis. Heating solutions of 25-s and 25-a in benzene at 50° C. for 13 h did not cause isomerization of 25-s to 25-a or 25-a to 25-s, respectively ($^1$H NMR spectroscopy). No decomposition was observed for 25-a, though 70% decomposition of 25-s was observed, based on the disappearance of the N$_1$—CH$_3$ peak in the $^1$H NMR spectrum. Heating of 25-s and 25-a at 70° C. for 8 h led to 100% and 10% decomposition, respectively, but no isomerization. Further heating of 25-a at 90° C. for 12 h caused significant decomposition, but no isomerization to 25-s. Analogous results were seen when heating 27-a and 27-s to 90° C. for 6 h resulting in about 60% decomposition of 27-s and 80% decomposition of 27-a. These studies indicate that the energetic barrier is too high for isomerization to occur at any appreciable rate at 25° C., consistent with the kinetics studies completed with the bis-salicylaldimines 7-a and 7-s (vide supra).

Example 29

Structure of Dinickel Complexes [Ref 52]

X-ray quality single crystals were obtained from a concentrated pentane solution cooled at −35° C. for 25-s and by vapor diffusion of hexanes into tetrahydrofuran at room temperature for 25-a. X-ray diffraction studies provided structural confirmation of the identity of the isomers (FIG. 13) as assigned by NMR spectroscopy above. The methyl groups are located trans to the phenoxide and the pyridine trans to the imine, as reported for similar coordination environments. [Ref 59] The Ni—Ni distance is 7.1 Å (average for the two molecules in the asymmetric unit) for the syn isomer (25-s). A slight distortion from square planar geometry is observed, probably due to the pyridine ligands that extend towards each other and tilt to avoid steric interaction. The planes of the two pyridines are about 3.86 Å apart, possibly indicative of a weak π interaction.[Ref 60] The direction of binding of the pyridine ligands indicates that appropriate substrates can reach both metal centers for cooperative interaction. Conversely, for the anti atropisomer (25-a) intramolecular cooperativity is not possible because of the large metal-metal distance (11.1 Å), and because the nickel centers are on opposite faces of the central arene ring. The N(1)-Ni(1)-N(2) and N(3)-Ni(2)-N(4) angles in the syn isomer of 173° and 166°, respectively (average for the two molecules in the asymmetric unit), and the N(1)-Ni(1)-N(2) angle of 177° in the anti isomer is nearly linear. Ni—N, Ni—O, and Ni-Me distances are similar to known complexes.[Ref 53, 59, 61-64] (See also Example 11).

Example 30

Ethylene Polymerization ([Ref 52]; See Also Example 12)

Ethylene homopolymerization trials were performed to determine the effect of reaction scale, reaction time, catalyst loading, and solvent (Table 6). Duplicate polymerization trials show changes in turnover frequencies (TOF) of less than 50% in the majority of cases. Increased reaction time led to increased polymer yield indicating that the catalyst remains active over extended periods (e.g. entries 3, 4, 5, Table 6). Ethylene polymerizations in 25 mL of toluene with 25-a and mononuclear counterparts 26, 27-a, 28, and 30 resulted in similar catalytic activities (TOFs 1200-3700 (mol C$_2$H$_4$)× (mol Ni)$^{-1}$×h$^{-1}$) (e.g. entries 3, 18, 23, 33, 37, Table 6). This level of activity is similar or lower than seen with nickel salicylaldimines that have a phosphine or nitrile ligand in place of the pyridine, which can be due in part to the stability of the pyridine-bound complex. [Ref 4] The highest TOFs were observed using 25-a and 26 (entries 3,18, Table 6). 25-s exhibits catalytic activity one order of magnitude less than 25-a (entries 10-13, Table 1), and is generally less active than the other investigated catalysts. Similarly, 27-s has activity three-fold lower than 27-a (entries 28, 29, Table 6). The observed difference in TOFs between 25-s and 25-a can be due to the effect of crowding of the catalytic pocket by the second nickel center. Similarly, steric bulk on the remote aryl of the terphenyl unit can be responsible for the difference between 27-s and 27-a.

Decreasing the scale of the polymerization reaction by five times (5 mL toluene) caused a significant drop in activity (e.g. entry 4 versus entry 7, Table 6). The concentration of nickel complex was doubled in order to collect enough polymer for analysis when running polymerizations at this scale. These changes in scale and concentration resulted in a reduction of TOF by two- to ten-fold (entries 4, 7; 12-15; 18-20; 23-25; 28-30; 33, 34; 37, 38, 40; Table 6). This effect is not well understood, but can be caused by changes in mixing of the solution and mass transfer problems, which could lower the effective concentration of ethylene in solution. To test the effect of mixing, a polymerization with 25-a was run with stirring at one third the rate used for all other polymerizations (entry 6, Table 6). The TOF in this polymerization was reduced by two-fold from an identical trial with the higher stirring rate (entries 4, 6, Table 6), supporting the hypothesis that insufficient mixing in the smaller scale polymerizations could contribute to the drop in activity. Changing the solvent from toluene to tetrahydrofuran (THF), did not significantly affect the activity of 25-28, but decreased the activity of 30 by four-fold (entries 7-9; 14-17; 20, 21; 30-32; 34-36; 40-42; Table 6). This drop in activity for 30 is similar to the three- to five-fold drop in TOF reported for polymerizations with phosphine-ligated nickel salicylaldimine complexes in the presence of excess ethers.[Ref 4, 65, 66] The notable lack of inhibition by THF of catalysts 25-28 can be due to the steric bulk of the fully substituted aryl group ortho to oxygen disfavoring ether coordination.

Polymer characterization by $^1$H and $^{13}$C NMR spectroscopy showed only methyl branch formation with peaks in the $D_2$-tetrachloroethane $^{13}$C NMR spectrum at δ 20.1, 27.5, 30.4, 33.4 and 37.6 ppm assigned to the methyl branch carbon, the β carbon, the γ carbon, the methyne carbon and the α carbon, respectively.[Ref 67] The variation in polymer branching level (determined by $^1$H NMR spectroscopy) was less than 35% for repeated trials, indicating good reproducibility.[Ref 68, 69] Polymers resulting from 25-s have the highest level of branching by at least two-fold compared to products from other catalysts under the same catalytic conditions (up to 70 branches/1000 C, entry 16, Table 6). Increase in polymer branching was also observed upon the combination of scale reduction, catalyst concentration increase, and the solvent change to THF (e.g. compare entries 12, 16, Table 6). Polymer branching is caused by chain walking processes that are dependent on relative rates of olefin insertion and β-H elimination/isomerization.[Ref 70-73] Increased ethylene concentration allows for faster olefin insertion compared to isomerization and leads to lower levels of branching. Higher branch density in the small-scale experiments is consistent with lower concentration of monomer due to inefficient mixing (as proposed for the decreased yield) and with the lower solubility of ethylene in THF.

Figure 26:
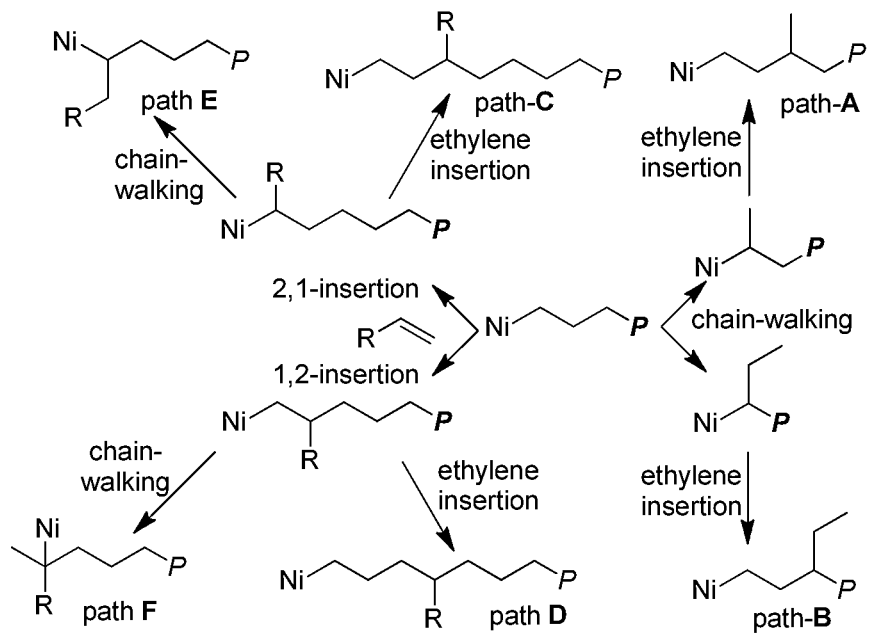
FIG. 26 shows a schematic illustration of possible insertion and chain walking processes during polymerization using the multi-metallic polymerization catalysts according to embodiments herein described.
Figure 40:
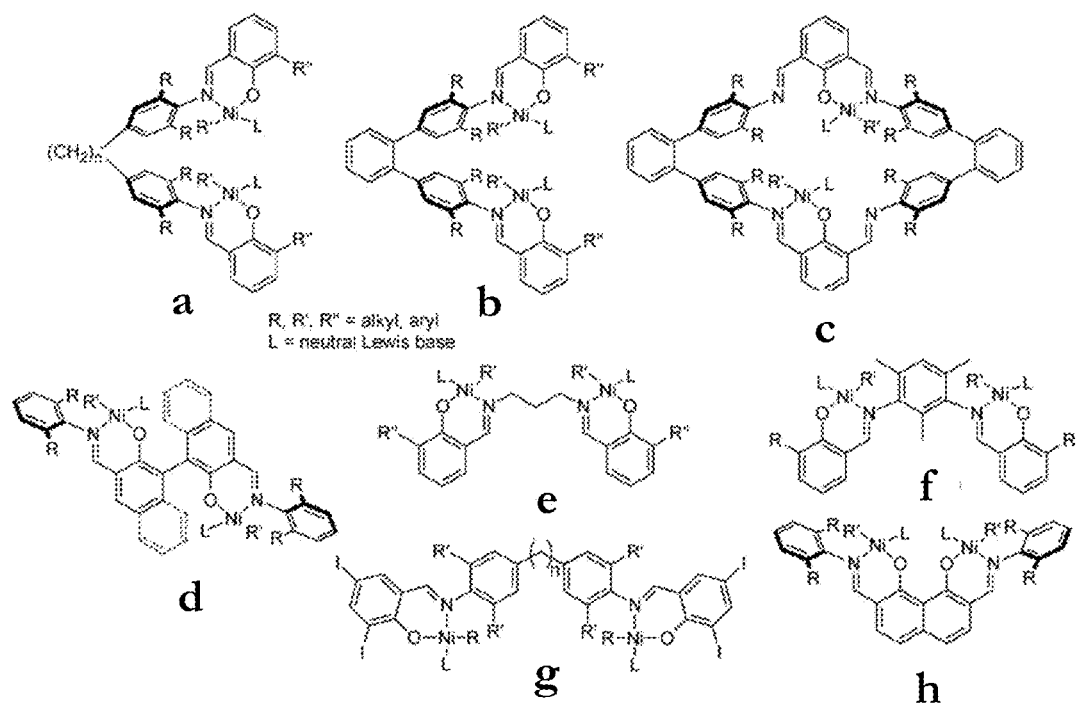
FIG. 40 shows dinuclear nickel phenoxyiminato complexes.

The selectivity for methyl branches is notable. Previously reported dinuclear nickel polymerization catalysts based on system h (FIG. 40) also generate polyethylene with only methyl branches and there are a few additional accounts of dinuclear nickel systems producing polyethylene with predominantly methyl branches.[Ref 65, 74] This contrasts with previously reported mononickel systems that show longer branches as well.[Ref 62, 63, 66, 75, 76] Catalysts 25-28 and 30 generate polyethylene with only methyl branches (path A, FIG. 26) suggesting that the proximal ligand environments hinder the formation of ethyl (or longer) branches regardless of the contributions from a second metal center. Bulky ligands can disfavor path B in FIG. 26, which involves species with nickel bound to a secondary carbon substituted with an ethyl group and the polymeryl chain. Similar to system h, the dinuclear syn isomer 25-s generates increased branch density compared to the mononuclear analogs. One explanation invokes slower propagation kinetics for 25-s compared to 25-a and the mononuclear systems, allowing for more extensive chain walking with 25-s. In THF, compound 27-s produced polymers with lower branching despite similar TOFs compared with 25-s (entries 16, 17, 31, 32, Table 6); this behavior suggests that the simple ligand sterics explanation is not fully satisfactory. However, a direct bimetallic interaction of pendant C—H bonds in the chain walking intermediates, as proposed for h, seems unlikely given the significant metal-metal distance.

TABLE 6

Ethylene homopolymerization trials.[a]

| Entry | Complex | mmol Ni | Solvent | Volume (mL) | Time (h) | Yield | TOF[b] | Branching[c] |
|---|---|---|---|---|---|---|---|---|
| 1 | 25-a | 0.0126 | toluene | 25 | 1 | 0.680 | 1924 | 3.4 |
| 2 | 25-a | 0.0126 | toluene | 25 | 1 | 0.940 | 2660 | |
| 3 | 25-a | 0.0200 | toluene | 25 | 1 | 2.079 | 3705 | |
| 4 | 25-a | 0.0200 | toluene | 25 | 3 | 3.415 | 2029 | 7.5 |
| 5 | 25-a | 0.0200 | toluene | 25 | 1.5 | 1.893 | 2250 | 6.0 |
| 6[d] | 25-a | 0.0200 | toluene | 25 | 3 | 1.875 | 1114 | |
| 7 | 25-a | 0.0080 | toluene | 5 | 3 | 0.118 | 280 | |
| 8 | 25-a | 0.0080 | THF | 5 | 3 | 0.101 | 150 | 18.8 |
| 9 | 25-a | 0.0080 | THF | 5 | 3 | 0.224 | 333 | 17.3 |
| 10 | 25-s | 0.0126 | toluene | 25 | 1 | 0.150 | 424 | 25.5 |
| 11 | 25-s | 0.0126 | toluene | 25 | 1 | 0.110 | 311 | 27.0 |
| 12 | 25-s | 0.0200 | toluene | 25 | 3 | 0.574 | 341 | 19.6 |
| 13 | 25-s | 0.0200 | toluene | 25 | 3 | 0.894 | 531 | 16.5 |
| 14 | 25-s | 0.0080 | toluene | 5 | 3 | 0.047 | 69 | |
| 15 | 25-s | 0.0080 | toluene | 5 | 3 | 0.036 | 53 | |
| 16 | 25-s | 0.0080 | THF | 5 | 3 | 0.041 | 60 | 70.3 |
| 17 | 25-s | 0.0080 | THF | 5 | 3 | 0.043 | 64 | 67.5 |
| 18 | 26 | 0.0200 | toluene | 25 | 3 | 5.532 | 3287 | |
| 19 | 26 | 0.0200 | toluene | 25 | 3 | 4.791 | 2846 | |
| 20 | 26 | 0.0080 | toluene | 5 | 3 | 0.549 | 815 | |
| 21 | 26 | 0.0080 | THF | 5 | 3 | 0.675 | 1003 | 7.2 |
| 22 | 26 | 0.0080 | THF | 5 | 1 | 0.172 | 766 | 8.4 |

TABLE 6-continued

Ethylene homopolymerization trials.[a]

| Entry | Complex | mmol Ni | Solvent | Volume (mL) | Time (h) | Yield | TOF[b] | Branching[c] |
|---|---|---|---|---|---|---|---|---|
| 23 | 27-a | 0.0200 | toluene | 25 | 3 | 3.113 | 1850 | 3.8 |
| 24 | 27-a | 0.0200 | toluene | 25 | 3 | 2.901 | 1724 | 5.1 |
| 25 | 27-a | 0.0080 | toluene | 5 | 3 | 0.083 | 123 | 12.0 |
| 26 | 27-a | 0.0080 | THF | 5 | 3 | 0.122 | 182 | 20.8 |
| 27 | 27-a | 0.0080 | THF | 5 | 3 | 0.170 | 253 | 15.7 |
| 28 | 27-s | 0.0200 | toluene | 25 | 3 | 1.205 | 716 | 3.8 |
| 29 | 27-s | 0.0200 | toluene | 25 | 3 | 1.301 | 773 | 4.3 |
| 30 | 27-s | 0.0080 | toluene | 5 | 3 | 0.047 | 70 | 9.6 |
| 31 | 27-s | 0.0080 | THF | 5 | 3 | 0.037 | 54 | 26.8 |
| 32 | 27-s | 0.0080 | THF | 5 | 3 | 0.041 | 61 | 27.2 |
| 33 | 28 | 0.0200 | toluene | 25 | 3 | 3.107 | 1846 | |
| 34 | 28 | 0.0080 | toluene | 5 | 3 | 0.100 | 148 | 10.8 |
| 35 | 28 | 0.0080 | THF | 5 | 3 | 0.099 | 147 | 19.6 |
| 36 | 28 | 0.0080 | THF | 5 | 3 | 0.081 | 121 | 19.6 |
| 37 | 30 | 0.0200 | toluene | 25 | 3 | 1.975 | 1174 | |
| 38 | 30 | 0.0200 | toluene | 25 | 3 | 2.879 | 1710 | |
| 39 | 30 | 0.0200 | toluene | 25 | 1 | 0.720 | 1284 | |
| 40 | 30 | 0.0080 | toluene | 5 | 3 | 0.416 | 618 | |
| 41 | 30 | 0.0080 | THF | 5 | 3 | 0.152 | 225 | 37.8 |
| 42 | 30 | 0.0080 | THF | 5 | 3 | 0.076 | 113 | 40.5 |

[a]All polymerizations were run in a glass reactor under 100 psig of ethylene at 25° C.
[b]TOF = turnover frequency in (mol $C_2H_4$) × (mol Ni)$^{-1}$ × h$^{-1}$.
[c]Branching was determined from $^1$H NMR spectroscopy and is reported as the number of branches per 1000 carbons.
[d]In this polymerization, the stirring was reduced to one third of the rate used for all other polymerizations.

Example 31

Ethylene/1-Hexene Copolymerization [Ref 52]

Ethylene/1-hexene copolymerization trials were also performed to determine the effects of reaction scale, comonomer concentration, reaction time, reaction temperature and solvent on the resultant copolymers (Table 7). As with the ethylene homopolymerizations, polymerizations with 25-s and 27-s produced the least polymer, and polymers synthesized using 25-s display the largest amount of branching (e.g. entries 6, 16, 18, 21, 24, 27, 29, Table 7). The change in activity from homopolymerizations of ethylene observed in experiments performed on a 25 mL scale (Table 6, entry 1 versus Table 2, entry 1) was one order of magnitude matching previous reports of one order of magnitude decrease in activity from ethylene homopolymerization upon addition of an α-olefin comonomer in large excess.[Ref 61] The drop observed on a 5 mL scale, however, was not as significant (only up to 4.4 times). The decrease in activity was previously explained by a slower insertion rate of the α-olefins.[Ref 61, 77] As expected, lower comonomer concentration led to higher TOF (Table 7 entries 4 and 5). Extension of the reaction time from 3 to 12 h resulted in a lowered TOF, presumably due to catalyst decomposition over time. Increasing the temperature resulted in a less than twofold decrease in activity in 3 h polymerization reactions and approximately no change in activity in 12 h polymerization runs (Table 7, entries 8 and 11 and entries 10 and 12). Change of solvent also had negligible effect on either the yield or the branching of the resultant polymers. Overall, the behavior of catalysts 25-a, 25-s, 26, 27-a, 27-s, 28, and 30 is comparable to previously reported monometallic systems.[Ref 61, 77] A noteworthy trend is the higher branching with the syn catalysts 25-s and 27-s; this can also be a consequence of the bulkier environment, which slows propagation compared to chain walking. Additionally, all of the polymers characterized by $^{13}$C NMR spectroscopy displayed only methyl and butyl branches, which is a unique microstructure. Further study of this phenomenon was accomplished by polymerization trials with other α-olefins.

TABLE 7

Ethylene/1-hexene copolymerization trials.[a]

| Entry | Complex | mmol Ni | Equiv hexene | Solvent | Volume (mL) | Temp (° C.) | Time (h) | Yield (g) | TOF[b] | Branching[c] | Branch type[d] |
|---|---|---|---|---|---|---|---|---|---|---|---|
| 1 | 25-a | 0.0200 | 8000 | toluene | 25 | 25 | 1 | 0.107 | 191 | 36.3 | m + b |
| 2 | 25-a | 0.0040 | 8000 | toluene | 5 | 25 | 3 | 0.030 | 89 | 49.1 | m + b |
| 3 | 25-a | 0.0080 | 4000 | toluene | 5 | 25 | 3 | 0.043 | 64 | 33.0 | m + b |
| 4 | 25-a | 0.0080 | 4000 | THF | 5 | 25 | 3 | 0.051 | 76 | 34.7 | m + b |
| 5 | 25-a | 0.0080 | 3200 | THF | 5 | 25 | 3 | 0.112 | 167 | 31.1 | m + b |
| 6 | 25-a | 0.0080 | 3200 | THF | 5 | 25 | 3 | 0.080 | 118 | 31.6 | m + b |
| 7 | 25-s | 0.0040 | 8000 | toluene | 5 | 25 | 1 | —[e] | —[e] | 92.2 | |
| 8 | 25-s | 0.0040 | 8000 | toluene | 5 | 25 | 3 | 0.020 | 59 | 76.6 | m + b |
| 9 | 25-s | 0.0040 | 8000 | toluene | 5 | 25 | 12 | 0.016 | 12 | 65.2 | m + b |
| 10 | 25-s | 0.0040 | 8000 | toluene | 5 | 25 | 12 | 0.040 | 30 | 78.4 | m + b |
| 11 | 25-s | 0.0040 | 8000 | toluene | 5 | 40 | 3 | 0.012 | 36 | | |
| 12 | 25-s | 0.0040 | 8000 | toluene | 5 | 40 | 12 | 0.044 | 32 | | |
| 13 | 25-s | 0.0080 | 4000 | toluene | 5 | 25 | 3 | 0.023 | 34 | 54.0 | m + b |
| 14 | 25-s | 0.0080 | 4000 | toluene | 5 | 25 | 3 | 0.017 | 25 | | |

TABLE 7-continued

Ethylene/1-hexene copolymerization trials.[a]

| Entry | Complex | mmol Ni | Equiv hexene | Solvent | Volume (mL) | Temp (°C.) | Time (h) | Yield (g) | TOF[b] | Branching[c] | Branch type[d] |
|---|---|---|---|---|---|---|---|---|---|---|---|
| 15 | 25-s | 0.0080 | 3200 | THF | 5 | 25 | 3 | 0.018 | 26 | 63.7 | m + b |
| 16 | 25-s | 0.0080 | 3200 | THF | 5 | 25 | 3 | 0.016 | 23 | 62.9 | m + b |
| 17 | 26 | 0.0080 | 3200 | THF | 5 | 25 | 3 | 0.193 | 287 | 32.8 | m + b |
| 18 | 26 | 0.0080 | 3200 | THF | 5 | 25 | 3 | 0.078 | 116 | 33.1 | m + b |
| 19 | 27-a | 0.0080 | 3200 | toluene | 5 | 25 | 3 | 0.132 | 195 | 31.4 | m + b |
| 20 | 27-a | 0.0080 | 3200 | THF | 5 | 25 | 3 | 0.092 | 136 | 34.8 | m + b |
| 21 | 27-a | 0.0080 | 3200 | THF | 5 | 25 | 3 | 0.066 | 99 | 33.9 | m + b |
| 22 | 27-s | 0.0080 | 3200 | toluene | 5 | 25 | 3 | 0.017 | 26 | 33.3 | m + b |
| 23 | 27-s | 0.0080 | 3200 | THF | 5 | 25 | 3 | 0.028 | 42 | 38.9 | m + b |
| 24 | 27-s | 0.0080 | 3200 | THF | 5 | 25 | 3 | 0.028 | 42 | 39.3 | m + b |
| 25 | 28 | 0.0080 | 3200 | toluene | 5 | 25 | 3 | 0.030 | 44 | 53.4 | m + b |
| 26 | 28 | 0.0080 | 3200 | THF | 5 | 25 | 3 | 0.063 | 94 | 38.5 | m + b |
| 27 | 28 | 0.0080 | 3200 | THF | 5 | 25 | 3 | 0.108 | 160 | 38.8 | m + b |
| 28 | 30 | 0.0080 | 3200 | THF | 5 | 25 | 3 | 0.094 | 140 | 44.6 | m + b |
| 29 | 30 | 0.0080 | 3200 | THF | 5 | 25 | 3 | 0.047 | 70 | 48.4 | m + b |

[a]All polymerizations were run in a glass reactor under 100 psig of ethylene.
[b]TOF = turnover frequency in (mol $C_2H_4$) × (mol Ni)$^{-1}$ × h$^{-1}$. This value is not adjusted for the amount of 1-hexene incorporated.
[c]Branching was determined from $^1$H NMR spectroscopy and is reported as the number of branches per 1000 carbons.
[d]Determined from $^{13}$C NMR spectroscopy: m = methyl, b = butyl.
[e]Too little polymer to accurately mass.

Example 32

Ethylene/α-Olefin Copolymerization [Ref 52]

Ethylene/α-olefin copolymerization trials were performed in duplicate with 25-a and 25-s and 1-pentene, 1-hexene, 1-heptene, and 1-octene to evaluate the effects of nickel-nickel proximity on branching, comonomer incorporation, TOF, molecular weight and molecular weight distribution (Table 8). Again, significantly more branching was observed in polymers produced with 25-s than in polymers produced with 25-a, but the percent incorporations of 1-pentene and 1-hexene were similar. This behavior suggests that the difference in the extent of branching was due to the presence of additional methyl branches from chain walking rather than to the incorporation of additional comonomer. With the longer α-olefins, 1-heptene and 1-octene, a greater degree of comonomer incorporation was seen in polymers generated by 25-a than by 25-s, likely due to increased steric hindrance in 25-s.

Figure 27:
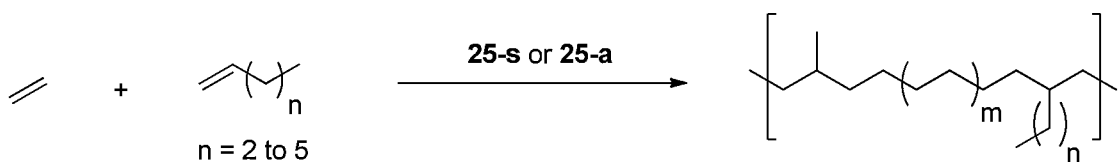
FIG. 27 shows a schematic illustration of branching observed with copolymerization of ethylene and alpha-olefins using the organometallic polymerization catalysts.

In all of the ethylene/α-olefin copolymers examined by $^{13}$C NMR spectroscopy (Table 7 and Table 8), only isolated methyl branches and branches the length of the comonomer chain were present. These data suggest that chain walking along the polyethylene chain to methyl branches occurs, but that after the insertion of a comonomer, no chain isomerization takes place before the coordination and insertion of the next ethylene monomer (paths C and D, FIG. 26; FIG. 27). To the best of the applicants' knowledge, this type of polymer microstructure has not been previously reported for ethylene-α-olefin copolymerization; it formally corresponds to an ethylene-propylene-α-olefin copolymer, without chain walking. [Ref 61, 77] Mecking et al. specifically report a variety of branch lengths including methyl, ethyl and butyl branches in the copolymerization of ethylene and 1-butene, which are attributed to various modes of insertion and subsequent chain walking.[Ref 77] Assuming 1,2-insertions are favored (paths D and F, FIG. 26), the difference in polymer microstructure achieved in polymerizations with the current systems can arise from the steric hindrance caused by the supporting ligand, disfavoring path F in which nickel migration to a tertiary carbon from a primary one.[Ref 77-79]

GPC analysis was performed on several of the ethylene/α-olefin copolymers (Table 8). In all cases, the molecular weights of polymers produced with 25-a were higher than of polymers produced with 25-s. The molecular weights for polymers produced with both 25-a and 25-s generally decreased with increasing comonomer size. The PDI values were between 3 and 4 except for the homopolymerization of ethylene with 25-a (PDI=7.5). Generally, lower PDI values were observed for 25-s compared to 25-a. The observed molecular weights and PDIs are in the range previously reported for mono- and dinickel catalysts.[Ref 4, 59, 62, 74, 80] Notably, high PDIs (5-8) were reported previously for bimetallic catalysts (c, f FIG. 40).[Ref 62, 63] The difference in polymer molecular weight is indicative of the relative rates of propagation vs chain termination, which depend on the rates of olefin insertion and β-H elimination, respectively. [Ref 81] The lower molecular weights for 25-s vs 25-a contrast with previous reports of a bimetallic catalsyt leading to an increase in M, vs the monometallic version,[Ref 63] but are consistent with the trends in TOF and branching level. Compared to 25-a, complex 25-s displays lower TOF and higher branching consistent with lower olefin insertion rates and higher β-H elimination rates, which is in agreement with the observed lower molecular weight polymers. Similar agreement between trends of $M_w$ vs TOF and polymer branching (for 25-a) were observed upon variation of the comonomer. The larger comonomers can lead to lower insertion rates due to steric reasons and result in lower $M_w$ polymers.[Ref 61, 77]

Copolymerizations of ethylene and polar monomers were also attempted. Using a large excess of a comonomer with a distal polar moiety, ethyl undecylenate (Table 8, entries 21 and 22; 2500 equivalents per nickel), led to a modest yield of polymer and incorporation within the range of previous reports for related catalysts.[Ref 61] Copolymerization attempts with 225 equivalents of N,N-dimethylallylamine per nickel resulted in polyethylene with no polar comonomer incorporation observed by $^1$H or $^{13}$C NMR spectroscopy, but larger inhibitory effects for 25-a compared to 25-s.[Ref 82] In contrast, copolymerization attempts with 225 equivalents of methyl acrylate per nickel resulted in no observable polymer. These data indicate that 25-a and 25-s tolerate some polar monomers. Additional investigations of the copolymerization of ethylene and polar monomers with these complexes are ongoing.

TABLE 8

Ethylene/α-olefin copolymerization trials with 25-a and 25-s.[a] (See also Table 2).

| Entry | Complex | Comonomer | Yield (g) | Branching[b] | Branch type[c] | Branch ratio[c] | % inc[d] | TOF e[e] | TOF co[e] | $M_w$[f] | $M_n$[f] | PDI[f] |
|---|---|---|---|---|---|---|---|---|---|---|---|---|
| 1 | 25-a | | 0.101 | 17.3 | m | | | 150 | | | | |
| 2 | 25-a | | 0.224 | 18.8 | m | | | 333 | | 47591 | 6309 | 7.54 |
| 3 | 25-s | | 0.041 | 70.3 | m | | | 60 | | | | |
| 4 | 25-s | | 0.043 | 67.5 | m | | | 64 | | 8114 | 2697 | 3.01 |
| 5 | 25-a | 1-pentene | 0.087 | 33.4 | m + p | 1:1.2 | 3.9 | 124 | 2.0 | 15238 | 4271 | 3.57 |
| 6 | 25-a | 1-pentene | 0.086 | 31.3 | m + p | 1:1.3 | 3.7 | 123 | 1.9 | | | |
| 7 | 25-s | 1-pentene | 0.044 | 70.2 | m + p | 1:0.3 | 3.4 | 64 | 0.9 | 7707 | 2583 | 2.98 |
| 8 | 25-s | 1-pentene | 0.028 | 76.1 | m + p | 1:0.3 | 3.7 | 39 | 0.6 | | | |
| 9 | 25-a | 1-hexene | 0.112 | 31.1 | m + b | 1:2.1 | 4.6 | 159 | 2.6 | 14088 | 3712 | 3.80 |
| 10 | 25-a | 1-hexene | 0.080 | 31.6 | m + b | 1:2.3 | 4.8 | 112 | 1.9 | | | |
| 11 | 25-s | 1-hexene | 0.018 | 63.7 | m + b | 1:0.4 | 3.9 | 25 | 0.3 | | | |
| 12 | 25-s | 1-hexene | 0.016 | 62.9 | m + b | 1:0.3 | 3.1 | 22 | 0.2 | 2759 | 893 | 3.09 |
| 13 | 25-a | 1-heptene | 0.053 | 36.0 | m + pn | 1:2.7 | 6.0 | 74 | 1.4 | 9097 | 3037 | 3.00 |
| 14 | 25-a | 1-heptene | 0.045 | 40.7 | m + pn | 1:3.2 | 7.3 | 61 | 1.4 | | | |
| 15 | 25-s | 1-heptene | 0.022 | 68.0 | m + pn | 1:0.5 | 5.1 | 31 | 0.5 | 3619 | 1196 | 3.03 |
| 16 | 25-s | 1-heptene | 0.006 | 61.3 | | | | | | | | |
| 17 | 25-a | 1-octene | 0.017 | 49.4 | m + h | 1:4.1 | 10.4 | 22 | 0.7 | 4472 | 1068 | 4.19 |
| 18 | 25-a | 1-octene | 0.017 | 49.5 | m + h | 1:6.2 | 11.5 | 22 | 0.7 | | | |
| 19 | 25-s | 1-octene | 0.012 | 61.0 | m + h | 1:0.6 | 5.3 | 17 | 0.2 | 2030 | 559 | 3.63 |
| 20 | 25-s | 1-octene | 0.009 | 51.1 | | | | | | | | |
| 21 | 25-a | $C_{13}H_{24}O_2$[g] | 0.037 | | | | 2.7 | 45 | 1.3 | | | |
| 22 | 25-s | $C_{13}H_{24}O_2$[g] | 0.002 | | | | 1.6 | 1.7 | 0.03 | | | |

[a] All polymerizations were run for 3 h in a glass reactor with 0.0080 mmol of nickel in THF under 100 psig of ethylene with 3200 equivalents of comonomer at 25° C. The total reaction volume was 5 mL.
[b] Branching was determined from $^1$H NMR spectroscopy and is reported as the number of branches per 1000 carbons.
[c] Determined from $^{13}$C NMR spectroscopy: m = methyl, p = propyl, b = butyl, pn = pentyl, h = hexyl.
[d] % incorporation was calculated from the overall branching and the branch ratio.
[e] TOF = turnover frequency in (mol monomer) × (mol Ni)$^{-1}$ × h$^{-1}$. "e" = ethylene, "co" = comonomer. Calculated from the yield and the % incoporation of comonomer.
[f] Calculated from GPC results.
[g] Ethyl undecylenate; used 2500 equivalents (4.8 mL) with 0.2 mL THF for a total volume of 5 mL.

Example 33

Ethylene Polymerization Trials [Ref 83]

Figure 28:
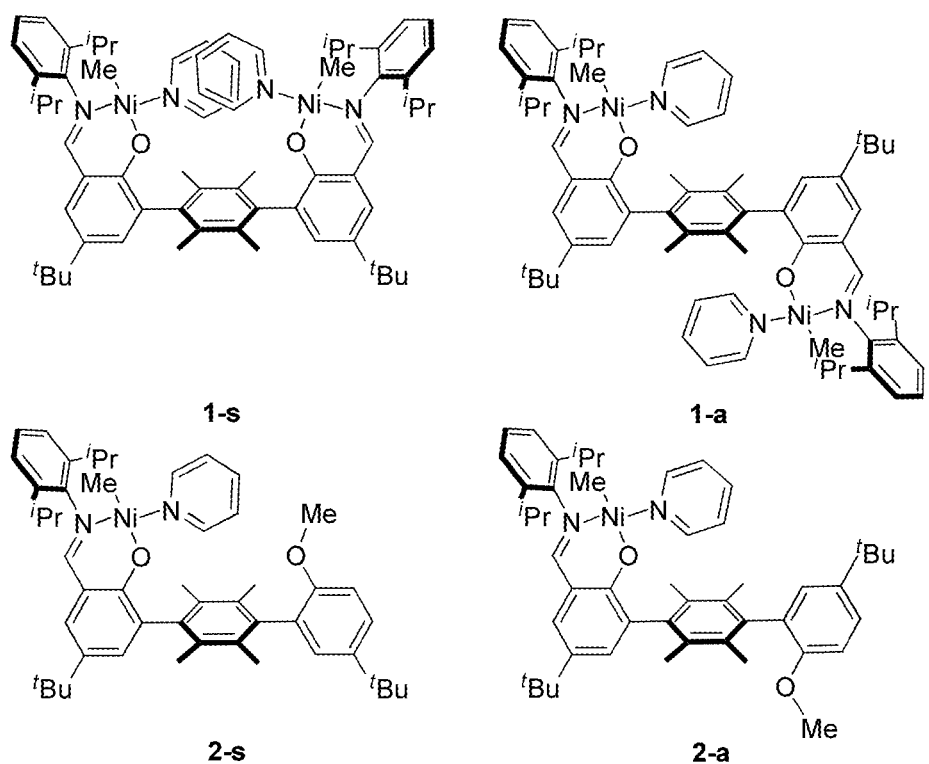
FIG. 28 shows the structures of multi-metallic polymerization catalysts according to embodiments herein described and mononucleating terphenyl-based salicylaldimine ligands for comparison to the multinucleating ligands according to embodiments herein described.

Ethylene polymerization trials were performed with the isolated nickel complexes in toluene at 25° C. (Table 9). The present catalysts perform ethylene polymerization with activities similar to previously reported pyridine-ligated nickel-phenoxyiminato systems.[Ref 59, 77] These experiments generate polyethylene with methyl branches (4 to 20 branches per 1000 carbon atoms).[Ref 67] Of the studied complexes, 1-s is the slowest catalyst by five-fold, likely due to the increased steric bulk at the active site compared to the other systems. The neutral ligands coordinated to the nickel centers in 1-s reach toward the second metal and hinder coordination of olefin. This proposal is supported by the distortion observed in the solid-state structure of 1-s. Although the methoxy substitutent is located syn with respect to nickel, the steric bulk in 2-s (FIG. 28) is likely not as large as that caused by the pyridine ligand bound to the second metal in the bimetallic system.

TABLE 9

Ethylene polymerization trials with 1-s and 1-a and polar additives.[a] (See also Table 3).

| | | Yield (g) | | TOF[b] | | |
|---|---|---|---|---|---|---|
| Additive | Equiv | 1-s | 1-a | 1-s | 1-a | R[c] |
| 1 none | n/a | 0.574 | 3.415 | 341 | 2029 | — |
| 2 none | n/a | 0.894 | 1.893[d] | 531 | 2250[d] | — |
| 3 NMe$_2$Et | 500 | 0.150 | 1.440 | 89 | 856 | 0.5 |
| 4 NMe$_2$Et | 500 | 0.148 | 1.032 | 88 | 613 | 0.7 |
| 5 NMe$_2$Et | 5000 | 0.068 | 0.103 | 41 | 61 | 3.3 |
| 6 NMeEt$_2$ | 500 | 0.128 | 0.181 | 76 | 108 | 3.5 |
| 7 NEt$_3$ | 500 | 0.039 | 0.016 | 23 | 9 | 12.2 |
| 8 NEt$_3$ | 500 | 0.010[d] | 0.006[d] | 12[d] | 7[d] | 8.0 |
| 9 NMe$_2$R$^{1e,f}$ | 225 | 0.058 | 0.071 | 103 | 126 | 4.0 |
| 10 NMe$_2$R$^{1e}$ | 500 | 0.062 | 0.111 | 36 | 66 | 2.7 |
| 11 NMe$_2$"Pr | 500 | 0.036 | 0.025 | 21 | 15 | 7.2 |
| 12 NMe"Pr$_2$ | 500 | 0.070 | 0.019 | 41 | 11 | 18.4 |
| 13 N"Pr$_3$ | 500 | 0.055 | 0.001 | 33 | 1 | 269 |
| 14 NMe$_2$"Bu | 500 | 0.047 | 0.019 | 25 | 10 | 12.1 |
| 15 NMe$_2$"Bu | 500 | 0.066 | 0.028 | 39 | 17 | 11.6 |
| 16 NMe"Bu$_2$ | 500 | 0.012 | 0.009 | 7 | 5 | 6.3 |
| 17 N"Bu$_3$ | 500 | 0.003 | —[i] | 2 | —[i] | — |
| 18 NMe$_2$Ph | 500 | 0.619 | 2.867 | 367 | 1703 | 1.1 |
| 19 NMe$_2$Bz | 500 | 0.252 | 1.330 | 150 | 790 | 0.9 |
| 20 HN"Pr$_2$ | 20 | —[i] | —[i] | —[i] | —[i] | — |
| 21 HNMe"Bu | 20 | —[i] | —[i] | —[i] | —[i] | — |
| 22 HN"Bu$_2$ | 20 | —[i] | —[i] | —[i] | —[i] | — |
| 23 HN$^i$Pr$_2$ | 20 | 0.299 | 0.149 | 178 | 88 | 9.9 |
| 24 H$_2$N"Bu | 5 | —[i] | —[i] | —[i] | —[i] | — |
| 25 H$_2$NR$^{2g}$ | 50 | 0.011 | —[i] | 7 | —[i] | — |
| 26 H$_2$NR$^{2g}$ | 20 | 0.022 | —[i] | 13 | —[i] | — |
| 27 H$_2$NR$^{2g}$ | 5 | 0.080 | 0.003 | 48 | 2 | 136 |

TABLE 9-continued

Ethylene polymerization trials with 1-s and 1-a and polar additives.[a]
(See also Table 3).

| | | Yield (g) | | TOF[b] | | |
|---|---|---|---|---|---|---|
| Additive | Equiv | 1-s | 1-a | 1-s | 1-a | R[c] |
| 28 H$_2$NR[3h] | 5 | 0.086 | 0.006 | 51 | 4 | 69.4 |
| 29 Pyridine | 10 | —[i] | —[i] | —[i] | —[i] | — |

[a]All polymerizations were run for 3 hours at 25° C. under 100 psig of ethylene in 25 ml of toluene with 10 μmol of dinickel complex. The number of equivalents of base listed is the number of equivalents per nickel.
[b]TOF = turnover frequency = (mol C$_2$H$_4$) × (mol Ni)$^{-1}$ × h$^{-1}$.
[c]R = ([TOF for 1-a with no additive]/[TOF for 1-a with additive])/([TOF for 1-s with no additive]/[TOF for 1-s with additive]).
[d]Polymerization was run for 1.5 hours.
[e]R$^1$ = allyl.
[f]Polymerization was run for 1 hour.
[g]R$^2$ = 1,1-dimethylpropyl.
[h]R$^3$ = 1,1,3,3-tetramethylbutyl.
[i]Insufficient product to accurately mass (<1 mg).

Ethylene polymerization trials in the presence of excess primary, secondary, and tertiary amines showed distinct inhibition trends (Table 9, Table 10). Complexes 1-a, 2-a, and 2-s were inhibited by two orders of magnitude upon the addition of N,N-dimethylbutylamine (Table 2). This deactivation effect in the presence of added amines is similar to that reported previously for related mononickel systems.[Ref 4] In contrast, 1-s was inhibited by only one order of magnitude. Consequently, in some cases (Table 9, entries 7, 8, 11-17), addition of a tertiary amine affords a syn catalyst that is more productive than the anti analog. The inhibition of the deactivation by amines observed only with 1-s is hereafter referred to as the bimetallic effect. The ratio between the deactivation of 1-a vs 1-s isomers (R) provides a quantitative measure of this effect. Compared to 1-s, catalyst 1-a is inhibited 10-25 times more by triethylamine, N-methyldipropylamine, and N,N-dimethylbutylamine and up to 270 times more by tripropylamine. Inhibition by triethylamine was also observed at a shorter polymerization time resulting in lower polymer yields for both 1-s and 1-a as well as a similar R, indicating that the calculated R is not due decomposition of the catalysts (Table 1 entry 8). The use of secondary or primary amines resulted in greater inhibition than the tertiary amines and, in all cases that yielded polymer, also displayed greater inhibition of 1-a than of 1-s (Table 9, entries 23, 25-28). Compared to 1-s, catalyst 1-a is inhibited approximately 10 times more with diisopropylamine and between 70 and 100 times more with 1,1-dimethylpropylamine and 1,1,3,3-tetramethylbutylamine (Table 9, entries 23, 25-28).

TABLE 10

Ethylene polymerization trials with 500 equivalents of N,N-dimethylbutylamine per nickel.[a]

| | Complex | Yield (g) | TOF[b] | R[d] |
|---|---|---|---|---|
| 1 | 1-s | 0.047 | 28 | 15 |
| 2 | 1-s | 0.066 | 39 | 11 |
| 3 | 1-a | 0.019 | 11 | 190 |
| 4 | 1-a | 0.028 | 17 | 130 |
| 5 | 2-s | 0.012 | 7 | 105 |
| 6 | 2-s | 0.010 | 6 | 121 |
| 7 | 2-a | 0.053 | 31 | 57 |
| 8 | 2-a | 0.048 | 29 | 62 |

[a]All polymerizations were run for 3 hours at 25° C. under 100 psig of ethylene in 25 ml of toluene with 20 μmol of nickel.
[b]TOF = turnover frequency = (mol C$_2$H$_4$) × (mol Ni)$^{-1}$ × h$^{-1}$.
[d]R = (TOF with no additive)/(TOF with additive).

The effect of amines on 1-s and 1-a was studied by $^1$H NMR spectroscopy. New N$_1$—CH$_3$ peaks were observed upon addition of one equivalent of 1,1-dimethylpropylamine, or of a large excess (≥100 equiv) of N,N-dimethylbutylamine or N,N-dimethylethylamine to 1-a and 1-s, indicating competitive substitution of pyridine. N,N-dimethylbenzylamine does not displace pyridine even upon addition of 100 equivalents. All investigated amines displaced more pyridine from 1-a than from 1-s. Qualitatively, the binding ability was found to vary in the following order: pyridine≈1,1-dimethylpropylamine>>N,N-dimethylbutylamine>N,N-dimethylethylamine>>N,N-dimethylbenzylamine. This trend mirrors the degree of inhibition recorded in ethylene polymerizations (Table 9, entries 4, 14, 19, 27, 29). The correlation suggests that stronger amine binding to nickel increases the bimetallic effect.

Figure 29:
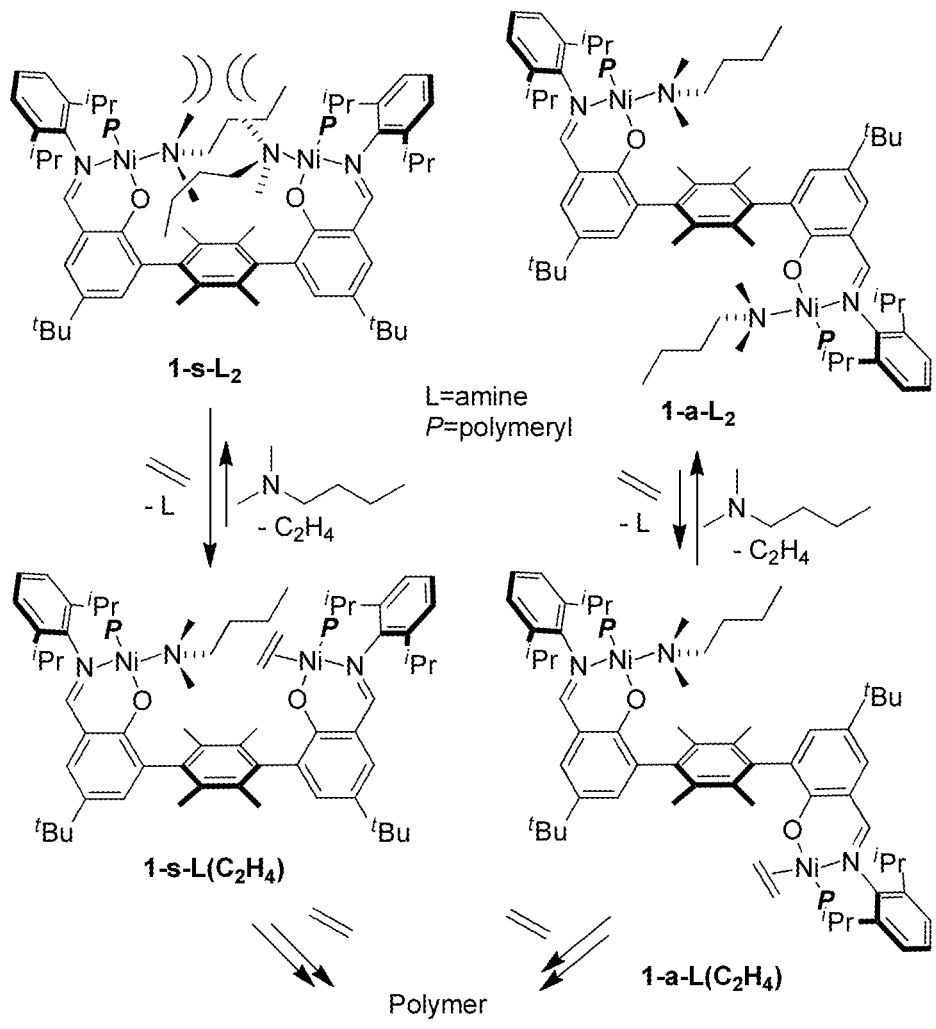
FIG. 29 shows a schematic illustration of possible competition between ethylene and amine for binding to the multi-metallic polymerization catalysts according to embodiments herein described.
Figure 30:
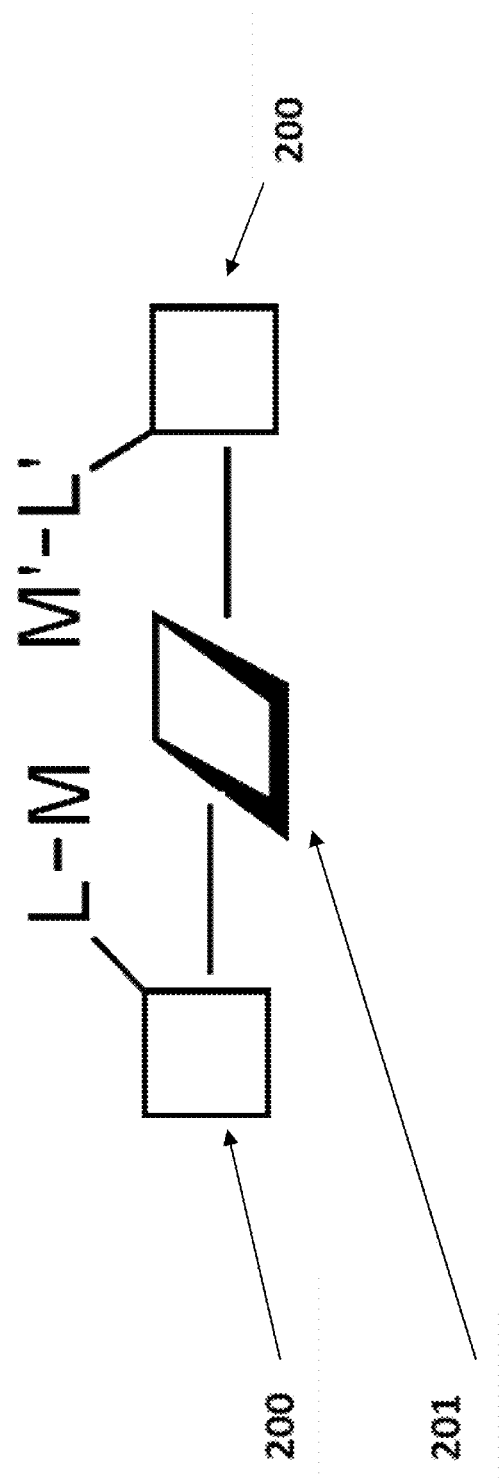
FIG. 30 shows a schematic illustrating a configuration of a multi-metallic organometallic complex according to some embodiments. In particular

The observed catalytic behavior suggests a bimetallic effect on the extent of inhibition by added base. Polymer formation is dependent on coordination of olefin and turnover limiting olefin insertion into the metal-polymeryl bond.[Ref 70, 84] Lewis bases compete with olefin for coordination to the metal and decrease the overall polymerization rate and polymer yield. [Ref 72, 73, 85, 86] While steric bulk from the ligand framework could cause a decrease in deactivation by hindering the binding of amine, the studied complexes show similar inhibition profiles for 1-a, 2-a, and 2-s in contrast to 1-s. The proximal arrangement of the two metal centers in compound I-s is proposed to cause the difference in deactivation compared to 1-a, 2-a, or 2-s (FIG. 29). Simultaneously binding a bulky base to each nickel center of 1-s is expected to be sterically disfavored compared to binding bases to all metal centers of 1-a, 2-a, or 2-s. Hence, for 1-s, ethylene can compete successfully with the amine for coordination to nickel. This has the net effect of inhibiting deactivation by the base for 1-s compared to 1-a, 2-a, or 2-s. Intriguingly, the proposed mechanism might also be relevant to the polymerization of olefins with binuclear cationic early transition metal catalysts, with the couteranions acting as inhibiting bases instead of amines.[Ref 87-90]

In agreement with the above mechanistic proposal, the extent of inhibition is dependent on the nature of the amine. The smallest amines induced a smaller difference between 1-s and 1-a. Binding of a smaller amine to one of the nickel centers of 1-s leaves space to bind a second amine to the other nickel center, thereby effecting inhibition similar to that seen for 1-a. For several of the secondary and primary amines (dipropylamine, N-methylbutylamine, dibutylamine, and butylamine), tight coordination and insufficient bulk result in no polymerization (Table 9, entries 20-22,24). With intermediate-size tertiary amines, as the size increases, the inhibition of 1-s is lowered compared to 1-a (NMeEt$_2$ vs NEt$_3$ and NMe$_2$″Bu vs NMe$_2$″ Pr vs NMe″Pr$_2$ vs N″Pr$_3$). This is consistent with the first coordinated amine hindering the binding of the second. Although X-ray quality crystals of the corresponding syn isomer have not been obtained, the solid-state structure of the 1,1-dimethylpropyl adduct of the bimetallic anti isomer highlights how the alkyl substituent of the primary amine extends toward the opposite aryl group, likely blocking the binding of a second amine in 1-s. With larger amines (NMe″Bu$_2$ and N″Bu$_3$), it is proposed that binding of an amine at one nickel prevents the binding of ethylene at the second nickel of 1-s; hence, the bimetallic effect is not apparent. Bulky and less basic N,N-dimethylbenzylamine and N,N-dimethylaniline show low inhibition likely because of weak binding to either isomer.

In summary, new mono- and dinickel ethylene polymerization catalysts are reported. The supporting ligands based on atropisomers of a locked terphenyl backbone allow for control of the relative position of the two catalytic centers. The syn bimetallic isomer shows less inhibition by added amines compared to the anti bimetallic and monometallic catalysts. The bimetallic effect observed with 1-s is proposed to arise from the close proximity of the nickels disfavoring simultaneous ligation of base to both of the metal centers. This behavior is expected to have applications in the design of olefin polymerization catalysts with increased functional group tolerance and with potential for copolymerization of polar olefins. Future studies will explore these areas along with extending the terphenyl motif with restricted rotation to other multimetallic catalyst systems.

Example 34

Alternative Synthesis of Binucleating Salicylaldimine Ligands ([Ref 52]; FIG. 20)

The synthesis of the binucleating ligands is based on well-documented procedures. 2-Bromo-4-tert-butyl-anisole (1) and 1,4-dibromo-2,3,5,6-tetramethylbenzene (2) starting materials were made using published syntheses.[Ref 91-93] Lithium-halogen exchange of 1, followed by treatment with $ZnCl_2$ afforded an aryl-zinc reagent suitable for a double Negishi cross-coupling with 2 (FIG. 20). The palladium-catalyzed coupling reaction led to a mixture of two atropisomers, syn (3-s) and anti (3-a). Bromination of 3 with $Br_2$ ortho to the methoxy groups generated dibromide 4. Column chromatography was used to separate the two atropisomers, which were then carried forward to the final ligand precursors, 7-s and 7-a, by the same synthetic procedures. Lithium-halogen exchange followed by addition of excess N,N-dimethylformamide (DMF) provided the diformyl species 5 upon aqueous work-up. Removal of the methyl protecting groups was accomplished with excess $BBr_3$ to afford compounds 6. Condensation with aniline generated the binucleating ligand precursors 7. The syntheses were high yielding overall: approximately 40% yield for the anti-analog (7-a) and 25% yield for the syn-analog (7-s).

In summary, in several embodiments, described herein are multi-metallic organometallic complexes that allow performance of olefin based reaction and in particular polymerization of olefins to produce polyolefin polymers, and related methods and systems are described.

The examples set forth above are provided to give those of ordinary skill in the art a complete disclosure and description of how to make and use the embodiments of multi-metallic organometallic complexes, and related polymers, methods and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, iso-propyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo", "halogen", and "halide" are used in the conventional sense to refer to a chloro, bromo, fluoro or iodo substituent or ligand.

The term "olefins" as used herein indicates two carbons covalently bound to one another that contain a double bond (sp2-hybridized bond) between them. The other functional groups bound to each of these two carbons can be, for example, additional carbons, hydrogen atoms, or heteroatoms.

The term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO$^-$), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)$_2$), mono-(C5-C24 aryl)-substituted carbamoyl (—(CO)—NH-aryl), di-(C5-C24 aryl)-substituted carbamoyl (—(CO)—N(C5-C24 aryl)$_2$), di-N—(C1-C24 alkyl), N—(C5-C24 aryl)-substituted carbamoyl, thiocarbamoyl (—(CS)—NH2), mono-(C1-C24 alkyl)-substituted thiocarbamoyl (—(CO)—NH(C1-C24 alkyl)), di-(C1-C24 alkyl)-substituted thiocarbamoyl (—(CO)—N(C1-C24 alkyl)$_2$), mono-(C5-C24 aryl)-substituted thiocarbamoyl (—(CO)—NH-aryl), di-(C5-C24 aryl)-substituted thiocarbamoyl (—(CO)—N(C5-C24 aryl)$_2$), di-N—(C1-C24 alkyl), N—(C5-C24 aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, etc.), C2-C20 alkylimino (CR=N(alkyl), where R=hydrogen, C1-C24 alkyl, C5-C24 aryl, C6-C24 alkaryl, C6-C24 aralkyl, etc.), arylimino (—CR=N(aryl), where R=hydrogen, C1-C20 alkyl, C5-C24 aryl, C6-C24 alkaryl, C6-C24 aralkyl, etc.), nitro (—NO$_2$), nitroso (—NO), sulfo (—SO2-OH), sulfonato (—SO2-O$^-$), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)$_2$), boronato (—B(OR)$_2$ where R is alkyl or other hydrocarbyl), phosphono (—P(O)(OH)$_2$), phosphonato (—P(O)(O$^-$)2), phosphinato (—P(O)(O$^-$)), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Widger, P. C., et al., "Isospecific polymerization of racemic epoxides: a catalyst system for the synthesis of highly isotactic polyethers". *Chem Commun (Camb)*, 2010. 46(17): p. 2935-7.
2. Britovsek, G. J. P., et al., "The Search for New-Generation Olefin Polymerization Catalysts: Life beyond Metallocenes". *Angewandte Chemie International Edition*, 1999. 38(4): p. 428-447.
3. Fuhrmann, H., et al., "Octahedral Group 4 Metal Complexes That Contain Amine, Amido, and Aminopyridinato Ligands: Synthesis, Structure, and Application in α-Olefin Oligo- and Polymerization". *Inorganic Chemistry*, 1996. 35(23): p. 6742-6745.
4. Younkin, T. R., et al., "Neutral, single-component nickel (II) polyolefin catalysts that tolerate heteroatoms". *Science*, 2000. 287(5452): p. 460-462.
5. Godoy Lopez, R., et al., "Synthesis of well-defined polymer architectures by successive catalytic olefin polymerization and living/controlled polymerization reactions". *Progress in Polymer Science*, 2007. 32(4): p. 419-454.
6. Amin, S. B., et al., "Versatile pathways for in situ polyolefin functionalization with heteroatoms: catalytic chain transfer". *Angew Chem Int Ed Engl*, 2008. 47(11): p. 2006-25.
7. Dong, J. Y., et al., "Synthesis of Isotactic Polypropylene Containing a Terminal Cl, OH, or NH2Group via Metallocene-Mediated Polymerization/Chain Transfer Reaction". *Macromolecules*, 2002. 35(25): p. 9352-9359.
8. Koning, C., "Strategies for compatibilization of polymer blends". *Progress in Polymer Science*, 1998. 23(4): p. 707-757.
9. Nakamura, A., et al., "Coordination-insertion copolymerization of fundamental polar monomers". *Chem Rev*, 2009. 109(11): p. 5215-44.
10. Chen, E. Y., "Coordination polymerization of polar vinyl monomers by single-site metal catalysts". *Chem Rev*, 2009. 109(11): p. 5157-214.
11. Imuta, J.-i., et al., "Catalytic Regioselective Introduction of Allyl Alcohol into the Nonpolar Polyolefins: Development of One-Pot Synthesis of Hydroxyl-Capped Polyolefins Mediated by a New Metallocene IF Catalyst". *Journal of the American Chemical Society*, 2002. 124(7): p. 1176-1177.
12. Zhang, Y., et al., "Catalyst-site-controlled coordination polymerization of polar vinyl monomers to highly syndiotactic polymers". *J Am Chem Soc*, 2010. 132(8): p. 2695-709.
13. Johnson, L. K., et al., "Copolymerization of ethylene and propylene with functionalized vinyl monomers by palladium(II) catalysts". *Journal of the American Chemical Society*, 1996. 118(1): p. 267-268.
14. Drent, E., et al., "Palladium catalysed copolymerization of ethene with alkylacrylates: polar comonomer built into the linear polymer chain". *Chemical Communications*, 2002(7): p. 744-745.
15. Pennington, D. A., et al., "The synthesis, structure and ethene polymerisation catalysis of mono(salicylaldiminato) titanium and zirconium complexes". *Dalton Trans*, 2005(3): p. 561-571
16. Wang, C., et al., "Synthesis and Characterization of Titanium(IV) Complexes Bearing Monoanionic [O—NX] (X=O, S, Se) Tridentate Ligands and Their Behaviors in Ethylene Homo- and Copolymerizaton with 1-Hexene". *Organometallics*, 2006. 25(13): p. 3259-3266.
17. Hanaoka, H., et al., "Synthesis and characterization of titanium and zirconium complexes with silicone-bridged phenoxycyclopentadienyl ligands". *Journal of Organometallic Chemistry*, 2007. 692(19): p. 4059-4066.
18. Dong, J.-Y., et al., "Design and synthesis of structurally well-defined functional polyolefins via transition metal-mediated olefin polymerization chemistry". *Coordination Chemistry Reviews*, 2006. 250(1-2): p. 47-65.
19. Leadbeater, N. E., et al., "Preparation of Polymer-Supported Ligands and Metal Complexes for Use in Catalysis". *Chemical Reviews*, 2002. 102(10): p. 3217-3274.
20. Maurya, M. R., et al., "Polymer-bound metal complexes as catalysts: Synthesis, characterization, reactivity and catalytic activity in E—H bond activation". *Journal of Organometallic Chemistry*, 2011. 696(1): p. 244-254.
21. Cornelissen, J. J., et al., "Chiral architectures from macromolecular building blocks". *Chem Rev*, 2001. 101(12): p. 4039-70.
22. Boffa, L. S., et al., "Copolymerization of polar monomers with olefins using transition-metal complexes". *Chemical Reviews*, 2000. 100(4): p. 1479-1493.
23. Delferro, M., et al., "Multinuclear olefin polymerization catalysts". *Chem Rev*, 2011. 111(3): p. 2450-85.

24. Kuran, W., "Coordination polymerization of heterocyclic and heterounsaturated monomers". *Progress in Polymer Science,* 1998. 23(6): p. 919-992.
25. Dechy-Cabaret, O., et al., "Controlled ring-opening polymerization of lactide and glycolide". *Chem Rev,* 2004. 104(12): p. 6147-76.
26. Anselment, T. M., et al., "Activation of late transition metal catalysts for olefin polymerizations and olefin/CO copolymerizations". *Dalton Trans,* 2008(34): p. 4537-48.
27. Bianchini, C., et al., "Alternating copolymerization of carbon monoxide and olefins by single-site metal catalysis". *Coordination Chemistry Reviews,* 2002. 225(1-2): p. 35-66.
28. Drent, E., et al., "Palladium-Catalyzed Alternating Copolymerization of Alkenes and Carbon Monoxide". *Chem Rev,* 1996. 96(2): p. 663-682.
29. Coates, G. W., et al., "Discrete metal-based catalysts for the copolymerization of CO2 and epoxides: discovery, reactivity, optimization, and mechanism". *Angew Chem Int Ed Engl,* 2004. 43(48): p. 6618-39.
30. Pangborn, A. B., et al., "Safe and convenient procedure for solvent purification". *Organometallics,* 1996. 15(5): p. 1518-1520.
31. Rodriguez, B. A., et al., "Bimetallic effects for enhanced polar comonomer enchainment selectivity in catalytic ethylene polymerization". *J Am Chem Soc,* 2009. 131(16): p. 5902-19.
32. Bauers, F. M., et al., "Aqueous homo- and copolymerization of ethylene by neutral nickel (II) complexes". *Macromolecules,* 2001. 34(5): p. 1165-1171.
33. Wehrmann, P., et al., "Highly Active Binuclear Neutral Nickel (II) Catalysts Affording High Molecular Weight Polyethylene". *Organometallics,* 2008. 27(7): p. 1399-1408.
34. Kiesewetter, E. T., et al., "Stereospecific octahedral group 4 bis(phenolate) ether complexes for olefin polymerization". *J Am Chem Soc,* 2010. 132(16): p. 5566-7.
35. Kaur, I., et al., "Design, synthesis, and characterization of a persistent nonacene derivative". *J Am Chem Soc,* 2010. 132(4): p. 1261-3.
36. Akama, T., et al., "Design and synthesis of potent antitumor 5,4'-diaminoflavone derivatives based on metabolic considerations". *J Med Chem,* 1997. 40(12): p. 1894-900.
37. Agapie, T., et al., "Cyclometalated Tantalum Diphenolate Pincer Complexes: Intramolecular C—H/M-CH₃σ-Bond Metathesis May Be Faster than O—H/M-CH3Protonolysis". *Organometallics,* 2007. 26(12): p. 2957-2959.
38. Mitchell, R. H., et al., "An Experimental Estimation of Aromaticity Relative to That of Benzene. The Synthesis and NMR Properties of a Series of Highly Annelated Dimethyldihydropyrenes: Bridged Benzannulenes". *Journal of the American Chemical Society,* 1995. 117(5): p. 1514-1532.
39. Yan, Y., et al., "Helical organization in foldable aromatic oligoamides by a continuous hydrogen-bonding network". *Org Lett,* 2009. 11(6): p. 1201-4.
40. Lodeiro, S., et al., "Protostadienol biosynthesis and metabolism in the pathogenic fungus *Aspergillus fumigatus*". *Org Lett,* 2009. 11(6): p. 1241-4.
41. Appiah, W. O., et al., "Linear Trimer Analogues of Calixarene as Chiral Coordinating Ligands: X-ray Crystallographic and NMR Spectroscopic Characterization of Chiral and Achiral Trisphenolates Complexed to Titanium (IV) and Aluminum (III)". *Inorganic Chemistry,* 2002. 41(14): p. 3656-3667.
42. Stead, D., et al., "A new sparteine surrogate for asymmetric deprotonation of N-Boc pyrrolidine". *Org Lett,* 2008. 10(7): p. 1409-12.
43. Connor, E. F., et al., "Synthesis of neutral nickel catalysts for ethylene polymerization—the influence of ligand size on catalyst stability". *Chem Commun (Camb),* 2003(18): p. 2272-3.
44. Klein, H.-F., et al., "Stabile Methylnickelverbindungen, II. Methyl(trimethylphosphin)nickel-hydroxid and verwandte Verbindungen". *Chemische Berichte,* 1973. 106(5): p. 1433-1452.
45. Dahl, 0., et al., "Four- and Five-Coordinate Nickel (II) Complexes with Trimethylphosphine". *Acta Chemica Scandinavica,* 1969. 23(7): p. 2342-2354.
46. Zuideveld, M. A., et al., "Remote substituents controlling catalytic polymerization by very active and robust neutral nickel (II) complexes". *Angew Chem Int Ed Engl,* 2004. 43(7): p. 869-73.
47. Rodriguez, B. A., et al., "Neutral Bimetallic Nickel (II) Phenoxyiminato Catalysts for Highly Branched Polyethylenes and Ethylene-Norbornene Copolymerizations". *Organometallics,* 2008. 27(10): p. 2166-2168.
48. Hamaed, A., et al., "H2 storage materials (22 KJ/mol) using organometallic Ti fragments as sigma-H2 binding sites". *J Am Chem Soc,* 2008. 130(22): p. 6992-9.
49. Covert, K. J., et al., "Carbon-oxygen and related R□X bond cleavages mediated by (silox)3Ti and other Group 4 derivatives (silox=tBu3SiO)". *Inorganica Chimica Acta,* 1997. 263(1-2): p. 263-278.
50. Manzer, L. E., "TETRAHYDROFURAN COMPLEXES OF SELECTED EARLY TRANSITION-METALS". *Inorganic Syntheses,* 1982. 21: p. 135-140.
51. Coates, G. E., et al., "Some co-ordination complexes of dimethyl- and diphenyl-magnesium with ethers and amines". *Journal of the Chemical Society A: Inorganic, Physical, Theoretical,* 1966(1): p. 26.
52. Radlauer, M. R., et al., "Dinickel Bisphenoxyiminato Complexes for the Polymerization of Ethylene and α-Olefins". *Organometallics,* 2012. 31(6): p. 2231-2243.
53. Wang, C. M., et al., "Neutral nickel (II)-based catalysts for ethylene polymerization". *Organometallics,* 1998. 17(15): p. 3149-3151.
54. Zysman-Colman, E., et al., "Synthesis of arylbromides from arenes and N-bromosuccinimide (NBS) in acetonitrile—A convenient method for aromatic bromination". *Canadian Journal of Chemistry-Revue Canadienne De Chimie,* 2009. 87(2): p. 440-447.
55. Moore, J. W., et al., *Kinetics and Mechanism.* 3rd ed. 1981, New York: John Wiley & Sons.
56. Lunazzi, L., et al., "Structure, conformation, and dynamic processes of the stereolabile atropisomers of hindered terphenyl hydrocarbons". *Organic Letters,* 2005. 7(7): p. 1291-1294.
57. Hoogasian, S., et al., "STEREODYNAMICS OF ACYCLIC ALCOHOLS, ETHERS, AND N,N-DIMETHYLURETHANES—POTENTIAL BARRIERS TO ROTATION ABOUT CARBON-CARBON AND CARBON-NITROGEN BONDS". *Journal of Physical Chemistry,* 1976. 80(6): p. 643-648.
58. Gust, D., "Restricted Rotation in Hexaarylbenzenes". *Journal of the American Chemical Society,* 1977. 99(21): p. 6980-6982.
59. Zuideveld, M. A., et al., "Remote substituents controlling catalytic polymerization by very active and robust neutral nickel (II) complexes". *Angewandte Chemie-International Edition,* 2004. 43(7): p. 869-873.

60. Janiak, C., "A critical account on [small pi]-[small pi] stacking in metal complexes with aromatic nitrogen-containing ligands". *Journal of the Chemical Society, Dalton Transactions,* 2000(21): p. 3885-3896.
61. Connor, E. F., et al., "Linear functionalized polyethylene prepared with highly active neutral Ni(II) complexes". *Journal of Polymer Science Part a-Polymer Chemistry,* 2002. 40(16): p. 2842-2854.
62. Na, S. J., et al., "Bimetallic nickel complexes of macrocyclic tetraiminodiphenols and their ethylene polymerization". *Journal of Organometallic Chemistry,* 2006. 691(4): p. 611-620.
63. Zhang, D., et al., "Bimetallic nickel complexes of trimethyl phenyl linked salicylaldimine ligands: Synthesis, structure and their ethylene polymerization behaviors". *Inorganic Chemistry Communications,* 2006. 9(12): p. 1322-1325.
64. Gottker-Schnetmann, I., et al., "Substituent effects in (kappa(2)-N,O)-salicylaldiminato nickel (II)-methylpyridine polymerization catalysts: Terphenyls controlling polyethylene microstructures". *Organometallics,* 2007. 26(9): p. 2348-2362.
65. Rodriguez, B. A., et al., "Bimetallic Effects for Enhanced Polar Comonomer Enchainment Selectivity in Catalytic Ethylene Polymerization". *Journal of the American Chemical Society,* 2009. 131(16): p. 5902-5919.
66. Chen, Q., et al., "Arene-Bridged Salicylaldimine-Based Binuclear Neutral Nickel (II) Complexes: Synthesis and Ethylene Polymerization Activities". *Organometallics,* 2007. 26: p. 617-625.
67. Crompton, T. R., *Analysis of Polymers: An Intoduction.* 1989: Pargamon Press.
68. The extent of polymer branching was determined by $^1$H NMR spectroscopy.
69. Gates, D. P., et al., "Synthesis of branched polyethylene using (alpha-diimine)nickel (II) catalysts: Influence of temperature, ethylene pressure, and ligand structure on polymer properties". *Macromolecules,* 2000. 33(7): p. 2320-2334.
70. Johnson, L. K., et al., "New Pd(II)-Based and Ni(II)-Based Catalysts for Polymerization of Ethylene and Alpha-Olefins". *Journal of the American Chemical Society,* 1995. 117(23): p. 6414-6415.
71. Gates, D. P., et al., "Synthesis of Branched Polyethylene Using (E±-Diimine)nickel (II) Catalysts:, Ää Influence of Temperature, Ethylene Pressure, and Ligand Structure on Polymer Properties". *Macromolecules,* 2000. 33(7): p. 2320-2334.
72. Mecking, S., et al., "Mechanistic studies of the palladium-catalyzed copolymerization of ethylene and alpha-olefins with methyl acrylate". *Journal of the American Chemical Society,* 1998. 120(5): p. 888-899.
73. Jenkins, J. C., et al., "A Mechanistic Investigation of the Polymerization of Ethylene Catalyzed by Neutral Ni(II) Complexes Derived from Bulky Anilinotropone Ligands". *Journal of the American Chemical Society,* 2004. 126(18): p. 5827-5842.
74. Rodriguez, B. A., et al., "Neutral bimetallic nickel (II) phenoxyiminato catalysts for highly branched polyethylenes and ethylene-norbornene copolymerizations". *Organometallics,* 2008. 27(10): p. 2166-2168.
75. Wang, W. H., et al., "Binuclear neutral nickel complexes bearing bis(bidentate) salicylaldiminato ligands: Synthesis, structure and ethylene polymerization behavior". *Inorganic Chemistry Communications,* 2006. 9(5): p. 548-550.
76. Hu, T., et al., "Synthesis and Ethylene Polymerization Activity of a Novel, Highly Active Single-Component Binuclear Neutral Nickel (II) Catalyst". *Organometallics,* 2005. 24: p. 2628-2632.
77. Wehrmann, P., et al., "Aqueous dispersions of polypropylene and poly(1-butene) with variable microstructures formed with neutral nickel (II) complexes". *Macromolecules,* 2006. 39(18): p. 5963-5964.
78. Schubbe, R., et al., "Structure of the Active Species and Explanation of the Migration Mechanism in 2,Omega-Polymerization of Alpha-Olefins". *Macromolecular Chemistry and Physics,* 1995. 196(2): p. 467-478.
79. Mecking reports both 1,2 and 2,1 insertions in α-olefin homopolymerizations, but indicates that this is in contrast with a report by Fink et al wherein they report only 1,2-insertions for a non-salicylaldiminato nickel system. Mecking suggests that the reason for this difference is steric crowding of the Ni center disfavoring 2,1 insertions.
80. Sujith, S., et al., "Ethylene/polar norbornene copolymerizations by bimetallic salicylaldimine-nickel catalysts". *Macromolecules,* 2005. 38(24): p. 10027-10033.
81. Klabunde, U., et al., "ETHYLENE HOMOPOLYMERIZATION WITH P,O-CHELATED NICKEL-CATALYSTS". *Journal of Polymer Science Part a-Polymer Chemistry,* 1987. 25(7): p. 1989-2003.
82. Radlauer, M. R., et al., "Manuscript in preparation". 2011.
83. Radlauer, M. R., et al., "Bimetallic Effects on Ethylene Polymerization in the Presence of Amines: Inhibition of the Deactivation by Lewis Bases". *Journal of the American Chemical Society,* 2012. 134(3): p. 1478-1481.
84. Ittel, S. D., et al., "Late-Metal Catalysts for Ethylene Homo- and Copolymerization". *Chemical Reviews,* 2000. 100(4): p. 1169-1204.
85. Wu, F., et al., "Acrylonitrile insertion reactions of cationic palladium alkyl complexes". *Journal of the American Chemical Society,* 2005. 127(6): p. 1841-1853.
86. Berkefeld, A., et al., "Mechanistic Insights on the Copolymerization of Polar Vinyl Monomers with Neutral Ni(II) Catalysts". *Journal of the American Chemical Society,* 2009. 131(35): p. 12613-12622.
87. Guo, N., et al., "Bimetallic Catalysis for Styrene Homopolymerization and Ethylene, àíStyrene Copolymerization. Exceptional Comonomer Selectivity and Insertion Regiochemistry". *Journal of the American Chemical Society,* 2004. 126(21): p. 6542-6543.
88. Li, H. B., et al., "Coordination copolymerization of severely encumbered isoalkenes with ethylene: Enhanced enchainment mediated by binuclear catalysts and cocatalysts". *Journal of the American Chemical Society,* 2005. 127(42): p. 14756-14768.
89. Li, H. B., et al., "Nuclearity and cooperativity effects in binuclear catalysts and cocatalysts for olefin polymerization". *Proceedings of the National Academy of Sciences of the United States of America,* 2006. 103(42): p. 15295-15302.
90. Guo, N., et al., "Bimetallic Effects in Homopolymerization of Styrene and Copolymerization of Ethylene and Styrenic Comonomers:, Ää Scope, Kinetics, and Mechanism". *Journal of the American Chemical Society,* 2008. 130(7): p. 2246-2261.
91. Kiesewetter, E. T., et al., "Stereospecific Octahedral Group 4 Bis(phenolate) Ether Complexes for Olefin Polymerization". *Journal of the American Chemical Society,* 2010. 132(16): p. 5566-+.
92. Yan, Y., et al., "Helical Organization in Foldable Aromatic Oligoamides by a Continuous Hydrogen-Bonding Network". *Organic Letters,* 2009. 11(6): p. 1201-1204.

93. Kaur, I., et al., "Design, Synthesis, and Characterization of a Persistent Nonacene Derivative". *Journal of the American Chemical Society*, 2010. 132(4): p. 1261-+.

The invention claimed is:

1. A multi-metallic organometallic complex comprising:
a rigid base linker comprising a central ring formed by a monocyclic or bicyclic aromatic moiety or a spirane moiety, the central ring attaching two or more exterior rings, each of the two or more exterior rings attaching a metal-presenting arm, thus defining two or more metal-presenting arms in syn position with respect to the rigid base linker,
wherein:
each metal-presenting arm of said two or more metal-presenting arms comprises one or more ancillary ligands presenting said metal,
said metal is bound to one or more auxiliary ligands through respective one or more auxiliary ligand metal bonds,
each said one or more auxiliary ligand metal bonds is adapted to be represented through corresponding one or more auxiliary ligand metal bond three-dimensional vectors originating at said metal,
metals pertaining to different metal-presenting arms are located at a metal-to-metal distance defining an imaginary sphere having said metal-to-metal distance as a diameter, and
for each of said metals located at the metal-to-metal distance, a resulting vector corresponding to a sum of said one or more auxiliary ligand metal bond three-dimensional vectors is located inside said imaginary sphere; and
wherein the multi-metallic organometallic complex has formula I:

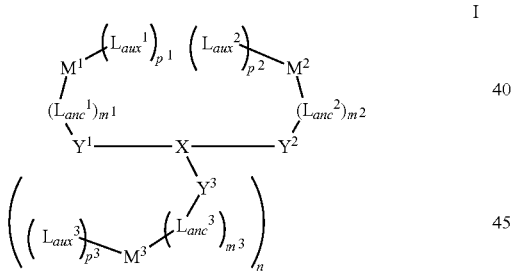

I wherein,
n is between 0 and 4;
m1, m2, and m3 are independently between 1 and 4;
p1, p2, and p3 are independently between 1 and 4;
X is the monocyclic or bicyclic aromatic moiety or the spirane moiety;
Y1, Y2, and Y3 independently comprise an aromatic, heteroaromatic, aliphatic, or heteroaliphatic ring;
$L_{anc}^1$, $L_{anc}^2$, and $L_{anc}^3$ are independently selected from a monodentate or a multidentate ligand;
$M^1$, $M^2$, and $M^3$ are metals; and
$L_{aux}^1$, $L_{aux}^2$, $L_{aux}^3$ are independently selected monodentate or a multidentate ligand.

2. The multi-metallic organometallic complex of claim 1, wherein the two or more exterior rings are each connected to the central ring through a single bond.

3. The multi-metallic organometallic complex of claim 1, wherein the central ring is a monocyclic or bicyclic heteroaromatic moiety or a heterospirane moiety and the two or more exterior rings independently comprise aromatic, heteroaromatic, aliphatic, or heteroaliphatic rings.

4. The multi-metallic organometallic complex of claim 1, wherein X has the formula II, III, IV, V, VI, VII, or VIII:

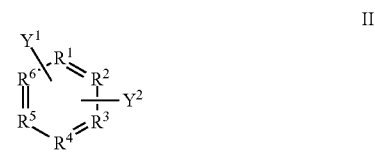

II

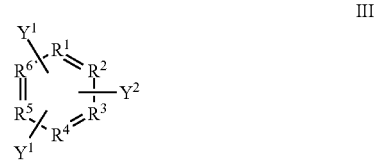

III

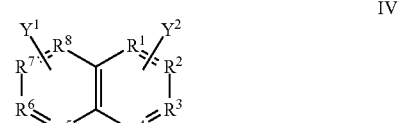

IV

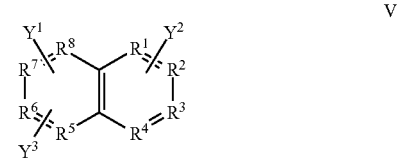

V

VI

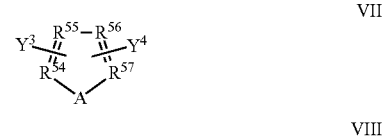

VII

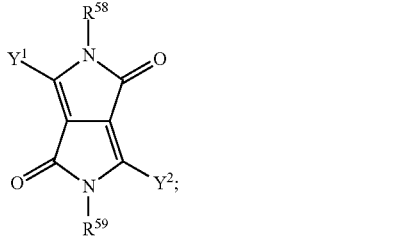

VIII wherein R1-R8 and R50-R57 are independently selected from the group consisting of N, C—H, C-alkyl, C-aryl, C-alkoxy, C-aryloxyl and a C attachment for Y1, Y2, Y3 or Y4; wherein at least one of R1-R8 and R50-57 in a corresponding ortho position with respect to Y1, and at least one of R1-R8 and R50-57 in a corresponding ortho position with respect to Y2 is not C—H, and at least one of R1-R8 and R50-57 in a corresponding ortho position with respect to Y3 is not C—H, and A is O, N—H, or S, and wherein R58 and R59 are independently selected from the group consisting of H, alkyl, aryl, alkoxy, and aryloxyl.

5. The multi-metallic organometallic complex of claim 1, wherein Y1, Y2, and Y3 have formula IX, X, XI, XII, or XIII:

wherein $L_{anc}{}^a$ has the formula XIV, XV, XVI, or XVII:

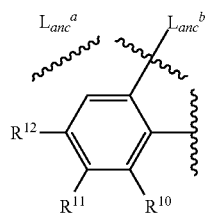

IX

XIV

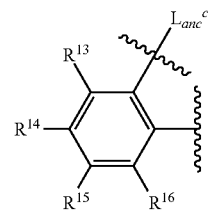

X

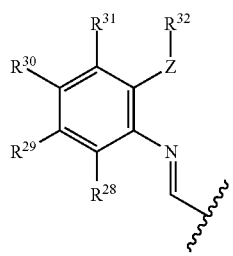

XV

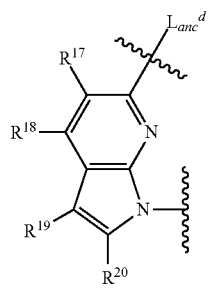

XI

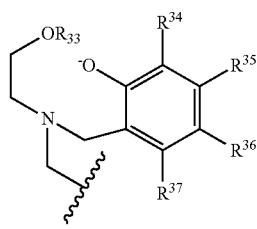

XVI

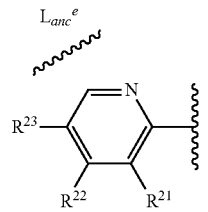

XII

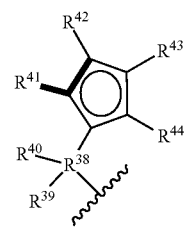

XVII

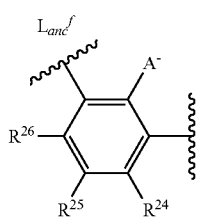

XIII wherein R27 is alkyl, aryl, heteroaryl, substituted aryl, R28-R37 and R39-44 are selected from the group consisting of H, linear $C_1$-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl; R38 is C or Si; Z=O, S, Se, or N;

$L_{anc}{}^b$ comprises an O, N, or C;

$L_{anc}{}^c$ comprises an O, N, or C; and $L_{anc}{}^d$, $L_{anc}{}^e$, and $L_{anc}{}^f$ are independently selected from the group consisting of:

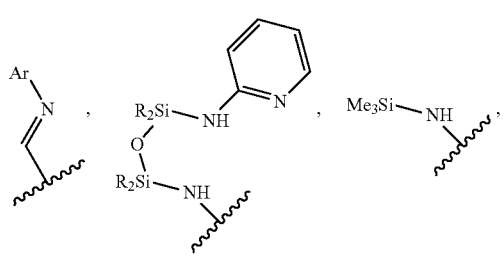

in which

R10 to R26 are independently selected from the group consisting of H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl;

wherein $L_{anc}{}^1$, $L_{anc}{}^2$, and $L_{anc}{}^3$ comprise one or more ancillary ligands, independently selected from $L_{anc}{}^a$, $L_{anc}{}^b$, $L_{anc}{}^b$, $L_{anc}{}^d$, $L_{anc}{}^e$, and $L_{anc}{}^f$;

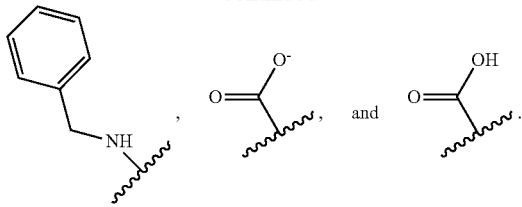

6. The multi-metallic organometallic complex of claim 1, wherein $L_{anc}^1$, $L_{anc}^2$, and $L_{anc}^3$ comprise one or more ancillary ligands, independently selected from $L_{anc}^a$, $L_{anc}^b$, $L_{anc}^c$, $L_{anc}^d$, $L_{anc}^e$, and $L_{anc}^f$, wherein $L_{anc}^a$ has the formula XIV, XV, XVI, or XVII:

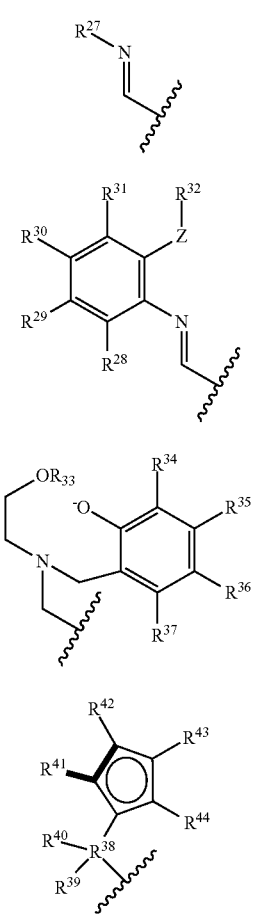

wherein R27 is alkyl, aryl, heteroaryl, substituted aryl, R28-R37 and R39-44 are selected from the group consisting of H, linear C1-C15 alkyl; branched linear C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl; R38 is C or Si; Z=O, S, Se, or N;

$L_{anc}^b$ comprises an O, N, or C;

$L_{anc}^c$ comprises an O N, or C; and $L_{anc}^d$, $L_{anc}^e$, and $L_{anc}^f$ are independently selected from the group consisting of:

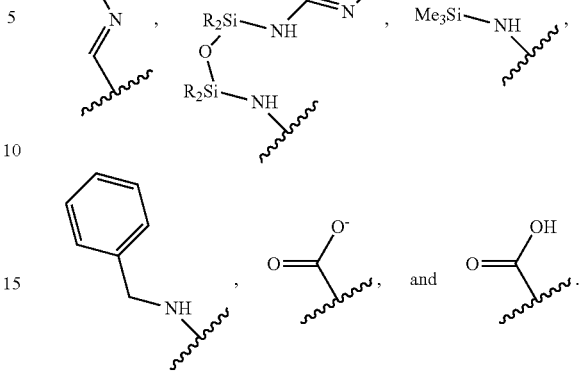

7. The multi-metallic organometallic complex of claim 1, wherein $L_{aux}^1$, $L_{aux}^2$, and $L_{aux}^3$ independently comprise an O, N, alkyl, aryl, amine, alkyloxide, aryloxide, or halogen.

8. The multi-metallic organometallic complex of claim 1, wherein $M^1$, $M^2$, and $M^3$ are independently selected from the group consisting of nickel, titanium, zirconium, yttrium, hafnium, cobalt, iron, palladium, aluminum, zinc, indium, gallium and a lanthanide metal.

9. A method for preparing a polyolefin, the method comprising contacting an olefin monomer with the multi-metallic organometallic complex of claim 1 for a time and under condition to allow polymerization to the olefin monomers.

10. The method of claim 9, wherein the olefin monomer is polar monomer.

11. The method according to claim 9, further comprising contacting the olefin monomer and the multi-metallic organometallic complex with a suitable activator or a phosphine scavenger.

12. The method according to claim 9 wherein the polyolefin is isotactic.

13. A polyolefin, obtainable by the method according to claim 9.

14. A method for preparing polyolefin copolymers, the method comprising contacting two or more olefin monomers with the multi-metallic organometallic complex of claim 1.

15. A method for preparing a polyolefin block copolymer, the method comprising sequentially contacting two or more olefin monomers, each of the two or more olefin monomers being structurally different from another, with the multi-metallic organometallic complex of claim 1 for a time and under condition to allow a first monomer to polymerize before a contacting with a subsequent monomer.

16. The method of claim 15, wherein the polyolefin block copolymers is a stereoblock copolymer.

17. The method of claim 16, wherein a tacticity is different between blocks of the stereoblock copolymer.

18. A method for preparing polyolefins, the method comprising contacting an olefin monomer with the organometallic complex of claim 1 with an olefin monomer wherein the multi-metallic organometallic complex comprises two or more modified multi-metallic organometallic complexes linked by a central ring and having restricted rotation of the monometallic complexes about the central ring.

19. A catalytic system for olefin polymerization, the system comprising the multi-metallic organometallic complex of claim 1 and an olefin monomer.

20. The catalytic system of claim 19, further comprising a suitable activator.

21. A method for preparing a multi-metallic organometallic complex of claim 1, the method comprising:
    selecting a central ring;
    selecting two or more exterior rings, the exterior rings;
    contacting the central ring with the two or more exterior rings to provide a rigid linker;
    selecting one or more ancillary ligands, one or more metals, and one or more auxiliary ligands;
    contacting the rigid linker with the one or more ancillary ligands to provide an organometallic complex precursor; and
    contacting the organometallic complex precursor with the one or more metals and auxiliary metals to provide the organometallic complex.

22. The method of claim 9, wherein the olefin monomer comprises one or more amine groups.

23. The method of claim 9, wherein the contacting of an olefin monomer with the multi-metallic organometallic complex is performed in the presence of polar additives.

24. The multi-metallic organometallic complex of claim 1 comprising:
    wherein the rigid base linker comprises a central with the external rings at 1,2-, 1,3-, 1,4-, or 1,3,5 positions around the central substituted benzene ring or a spirane-type moiety.

25. The multi-metallic organometallic complex of claim 1, wherein X has the formula II, III, IV, V, VI, VII, or VIII:

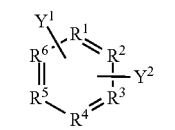

II

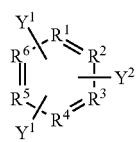

III

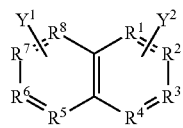

IV

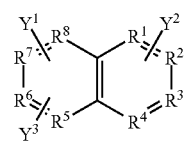

V

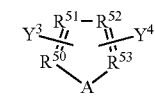

VI

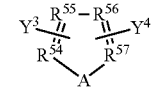

VII

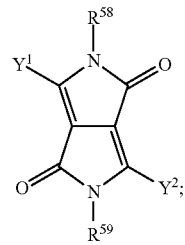

VIII wherein R1-R8 and R50-R57 is independently selected from the group consisting of N, C—H, C-alkyl, C-aryl, C-alkoxy, C-aryloxyl and a C attachment $Y_1$, Y2, Y3, or $Y_4$; wherein at least one of R1-R8 and in a corresponding ortho position with respect to Y1 is C—H, and at least one of R50-57 in a corresponding ortho position with respect to Y1, and at least one of R1-R8 and R50-57 in a corresponding ortho position with respect to Y2 is not C—H, and at least one of R1-R8 and R50-57 in a corresponding ortho position with respect to Y3 is not C—H, and A is O, N—H, or S,
wherein R58 and R59 are independently selected from the group consisting of H, alkyl, aryl, alkoxy, and aryloxyl.

26. The multi-metallic organometallic complex of claim 4, wherein each of R2, R3, R5 and R6 is independently C-alkyl.

27. The multi-metallic organometallic complex of claim 4, wherein each of R2, R4 and R6 is independently C-alkyl.

28. The multi-metallic organometallic complex of claim 26, wherein metals pertaining to different metal-presenting arms comprise at least two different metals.

29. The multi-metallic organometallic complex of claim 4, wherein
    n is 0
    X is formula II, wherein R1-R6 is independently selected from the group consisting of N, C—H, C-alkyl, C-aryl, C-alkoxy, C-aryloxyl and a C attachment for Y1 or Y2.

30. The multi-metallic organometallic complex of claim 29, wherein at least one of R1-R6 in a corresponding ortho position with respect to Y1 is C—H.

31. The multi-metallic organometallic complex of claim 1, wherein the monocyclic or bicyclic aromatic moiety is selected from the group comprising benzene and naphthalene moieties.

32. The multi-metallic organometallic complex of claim 1, wherein
    each substituted ring atom of the central ring is independently selected from the group consisting of N, C—H, C-alkyl, C-aryl, C-alkoxy, C-aryloxyl and a C attachment for Y1, Y2 or Y3;
    the each of the two or more exterior rings attaching a metal-presenting arm, independently comprises an aromatic, heteroaromatic, aliphatic, or heteroaliphatic ring and presenting $M^1$ or $M^2$ metals; and
    each metal-presenting arm of said two or more metal-presenting arms comprises one to four ancillary monodentate or multidentate ligands presenting $M^1$ or $M^2$ metals.

* * * * *